US011466260B2

(12) United States Patent
Maupin-Furlow et al.

(10) Patent No.: US 11,466,260 B2
(45) Date of Patent: Oct. 11, 2022

(54) THERMOSTABLE HALOARCHAEAL INORGANIC PYROPHOSPHATASE

(71) Applicant: UNIVERSITY OF FLORIDA RESEARCH FOUNDATION, INCORPORATED

(72) Inventors: Julie A. Maupin-Furlow, Gainesville, FL (US); Nathaniel L. Hepowit, Nashville, TN (US); Lana McMillan, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 405 days.

(21) Appl. No.: 15/766,447

(22) PCT Filed: Oct. 19, 2016

(86) PCT No.: PCT/US2016/057627
§ 371 (c)(1),
(2) Date: Apr. 6, 2018

(87) PCT Pub. No.: WO2017/070164
PCT Pub. Date: Apr. 27, 2017

(65) Prior Publication Data
US 2018/0371433 A1 Dec. 27, 2018

Related U.S. Application Data

(60) Provisional application No. 62/243,260, filed on Oct. 19, 2015.

(51) Int. Cl.
C12N 9/14 (2006.01)
C12Q 1/42 (2006.01)
C12N 9/16 (2006.01)

(52) U.S. Cl.
CPC .............. C12N 9/14 (2013.01); C12N 9/16 (2013.01); C12Q 1/42 (2013.01); C12Y 306/01001 (2013.01)

(58) Field of Classification Search
None
See application file for complete search history.

(56) References Cited

PUBLICATIONS

Andreeva et al., Inorganic Polyphosphates and Phosphohydrolases in Halobacterium salinarium, Microbiology; vol. 69, No. 4, 2000, pp. 411-416. Translated from Mikrobiologiya, vol. 69, No. 4, 2000, pp. 499-505 (Year: 2000).*
Oren et al., Taxonomy of the family Halobacteriaceae: a paradigm for changing concepts in prokaryote systematics, International Journal of Systematic and Evolutionary Microbiology (2012), 62, 263-271 (Year: 2012).*
CP001956, GenBank Entry, 2010 (Year: 2010).*
Timpson et al., A comparison of two novel alcohol dehydrogenase enzymes (ADH1 and ADH2) from the extreme halophile Haloferax volcanii, Appl Microbiol Biotechnol (2013) 97:195-203 (Year: 2013).*
Aravind et al., Phosphoesterase domains associated with DNA polymerases of diverse origins, p. 3746-3752 Nucleic Acids Research, 1998, vol. 26, No. 16 (Year: 1998).*
Behrens et al., Synthesis of pyrophosphate by chromatophores of RIzodospirihm rubrum in the light and by soluble yeast inorganic pyrophosphatase in water-organic solvent mixtures, Eur. J. Biochem. 152,221-227 (1985) (Year: 1985).*
Gomez-Puyou et al., Synthesis of Medium Pyrophosphate by Soluble Mitochondrial F1 through Dimethyl Sulfoxide-Water Transitions, JBC, vol. 270, No. 28, Issue of Jul. 2014, pp. 16820-16825, 1995 (Year: 1995).*
Cestari, I., Stuart, K., A spectrophotometric assay for quantitative measurement of aminoacyl-tRNA synthetase activity, J. Biomol. Screen. pp. 490-497, vol. 18, Issue 4 (2013).
Hartman, A., et al., The complete genome sequence of Haloferax volcanii DS2 a Model archaeon, "PLoS one" pp. 1-20, vol. 5, Issue 3 (2010).
Oxenrider, K., Kennelly, P., A protein-serine phosphatase from the halophilic archaeon haloferax volcanii, "Biochemical and biophysical research comm.", pp. 1330-1335, vol. 194. Issue 3 (1993).
T. Allers, H.P. Ngo, M. Mevarech, and R.G. Lloyd, Development of additional selectable markers for the halophilic archaeon Haloferax volcanii based on the leuB and tlpA genes. Appl Environ Microbiol 70 (2004) 943-53.
P. Arriagada-Strodthoff, S. Karboune, R.J. Neufeld, and S. Kermasha, Optimization of chlorophyllase-catalyzed hydrolysis of chlorophyll in monophasic organic solvent media. Appl Biochem Biotechnol 142 (2007) 263-75.
AM. Blinkovsky, B.D. Martin, and U.S. Dordick, Enzymology in monophasic organic media. Curr Opin Biotechnol 3 (1992) 124-9.
M.M. Bradford, A rapid and sensitive method for the quantitation of microgram quantities of protein utilizing the principle of protein-dye binding. Anal Biochem 72 (1976) 248-54.

(Continued)

Primary Examiner — Louise W Humphrey
Assistant Examiner — Srikanth Patury
(74) Attorney, Agent, or Firm — Timothy H. Van Dyke; Wolter, Van Dyke, Davis, PLLC

(57) ABSTRACT

The invention pertains to a PPA from a microorganism belonging to the family Halobacteriaceae (HPPA), for example, a PPA from *Haloferax volcanii*. The HPPA provided by the invention is soluble, thermostable and active at high concentrations of salt and/or organic solvent. An embodiment of the invention provides a method of increasing the rate of a reaction by adding an HPPA to the reaction mixture, wherein the reaction produces PPi, for example, an enzymatic reaction, and wherein the reaction is carried out at moderately high temperature and/or low water activity. Further embodiments of the invention provide an assay to detect the PPi released during a reaction which produces PPi by adding an HPPA to convert the PPi in to Pi and measuring the resultant Pi. The invention further pertains to an assay to monitor a reaction which produces PPi in the presence or the absence of an HPPA.

8 Claims, 11 Drawing Sheets
Specification includes a Sequence Listing.

(56) References Cited

PUBLICATIONS

R. De Castro, D. Ruiz, M. Gimenez, M. Silveyra, R. Paggi, and J. Maupin-Furlow, Gene cloning and heterologous synthesis of a haloalkaliphilic extracellular protease of Natrialba magadii (Nep). Extremophiles 12 (2008) 677-687.

J.S. Dordick, Non-aqueous enzymology. Curr Opin Biotechnol 2 (1991) 401-7.

M. Dyall-Smith, The Halohandbook: Protocols for Halobacterial Genetics, Version 7.2, Mar. 2009.

C.S. Francklyn, E.A. First, J.J. Perona, and Y.M. Hou, Methods for kinetic and thermodynamic analysis of aminoacyl-tRNA synthetases. Methods 44 (2008) 100-18.

T.P. Geladopoulos, T.G. Sotiroudis, and A.E. Evangelopoulos, A malachite green colorimetric assay for protein phosphatase activity. Anal Biochem 192 (1991) 112-6.

R. Grazinoli-Garrido, and M. Sola-Penna, Inactivation of yeast inorganic pyrophosphatase by organic solvents. An Acad Bras Cienc 76 (2004) 699-705.

T. Hansen, C. Urbanke, V.M. Leppanen, A Goldman, K. Brandenburg, and G. Schafer, The extreme thermostable pyrophosphatase from Sulfolobus acidocaldarius: enzymatic and comparative biophysical characterization. Arch Biochem Biophys 363 (1999) 135-47.

P. Heikinheimo, V. Tuominen, AK. Ahonen, A Teplyakov, B.S. Cooperman, A.A Baykov, R. Lahti, and A. Goldman, Toward a quantum-mechanical description of metal-assisted phosphoryl transfer in pyrophosphatase. Proc Natl Acad Sci U SA 98 (2001) 3121-6.

RC. Hughes, L. Coates, M.P. Blakeley, S.J. Tomanicek, P. Langan, A.Y. Kovalevsky, J.M. Garcia-Ruiz, and J.D. Ng, Inorganic pyrophosphatase crystals from Thermococcus thioreducens for X-ray and neutron diffraction. Acta Crystallogr Sect F Struct Biol Cryst Common 68 (2012) 1482-7.

K. Itaya, and M. Ui, A new micromethod for the colorimetric determination of inorganic phosphate. Clin Chim Acta 14 (1966) 361-6.

S.J. Jeon, and K. Ishikawa, Characterization of the Family I inorganic pyrophosphatase from Pyrococcus horikoshii OT3. Archaea 1 (2005) 385-9.

Y.L. Khmelnitsky, and J.O. Rich, Biocatalysis in nonaqueous solvents. Curr Opin Chem Biol 3 (1999) 47-53.

U.K. Laemmli, Cleavage of structural proteins during the assembly of the head of bacteriophage T4. Nature 227 (1970) 680-5.

R. Lahti, Microbial inorganic pyrophosphatases. Microbiol Rev 47 (1983) 169-78.

V.M. Leppanen, H. Nummelin, T. Hansen, R. Lahti, G. Schafer, and A Goldman, Sulfolobus acidocaldarius inorganic pyrophosphatase: structure, thermostability, and effect of metal ion in an archael pyrophosphatase. Protein Sci 8 ( 1999) 1218-31.

L. Li, Y. Liu, Y. Wan, Y. Li, X. Chen, W. Zhao, and P.G. Wang, Efficient enzymatic synthesis of guanosine 5'-diphosphate-sugars and derivatives. Org Lett 15 (2013) 5528-30.

X. Li, and H.Y. Yu, Characterization of an organic solvent-tolerant lipase from *Haloarcula* sp. G41 and its application for biodiesel production. Folia Microbiol (Praha) 59 (2014)455-63.

B. Liu, M. Bartlam, R. Gao, W. Zhou, H. Pang, Y. Liu, Y. Feng, and Z. Rao, Crystal structure of the hyperthermophilic inorganic pyrophosphatase from the archaeon Pyrococcus horikoshii. Biophys J 86 (2004) 420-7.

D.H. Lopes, J.R. Meyer-Fernandes, and M. Sola-Penna, Effects of trehalose and ethanol on yeast cytosolic pyrophosphatase. Z Naturforsch C 54 (1999) 186-90.

D.H. Lopes, and M. Sola-Penna, Urea increases tolerance of yeast inorganic pyrophosphatase activity to ethanol: the other side of urea interaction with proteins. Arch Biochem Biophys 394 (2001) 61-6.

D. Lu, G. Xie, and R. Gao, Cloning, purification, and characterization of inorganic pyrophosphatase from the hyperthermophilic archaea Pyrococcus horikoshii. Protein Expr Purif 99 (2014) 94-8.

A.T. Matheson, G.D. Sprott, I.J. McDonald, and H. Tessier, Some properties of an unidentified halophile: growth characteristics, internal salt concentration, and morphology. Can J Microbiol 22 (1976) 780-6.

B.J. Mengeling, and S.J. Turco, A high-yield, enzymatic synthesis of GDP-D-[3H]arabinose and GDP-L-[3H]fucose. Anal Biochem 267 (1999) 227-33.

W. Meyer, R. Moll, T. Kath, and G. Schafer, Purification, cloning, and sequencing of archaebacterial pyrophosphatase from the extreme thermoacidophile Sulfolobus acidocaldarius. Arch Biochem Biophys 319 (1995) 149-56.

H. Miranda, N. Nembhard, D. Su, N. Hepowit, D. Krause, J. Pritz, C. Phillips, D. Soil, and J. Maupin-Furlow, El- and ubiquitin-like proteins provide a direct link between protein conjugation and sulfur transfer in archaea. Proc Natl Acad Sci U S A 108 (2011)4417-22.

N. Munawar, and P.C. Engel, Prospects for robust biocatalysis: engineering of novel specificity in a halophilic amino acid dehydrogenase. Extremophiles 17 (2013) 43-51.

H.T. Nguyen, Y. Chong, D.K. Oh, Y.S. Heo, P.T. Viet, L.W. Kang, S.J. Jeon, and D.E. Kim, An efficient colorimetric assay for RNA synthesis by viral RNA-dependent RNA polymerases, using thermostable pyrophosphatase. Anal Biochem 434 (2013) 284-6.

T. Wakagi, C.H. Lee, and T. Oshima, An extremely stable inorganic pyrophosphatase purified from the cytosol of a thermoacidophilic archaebacterium, Sulfolobus acidocaldarius strain 7. Biochim Biophys Acta 1120 (1992) 289-96.

E. Oksanen, et al., A complete structural description of the catalytic cycle of yeast pyrophosphatase, "biochemistry", pp. 1228-1239, vol. 46 (2007).

S.Y. Park, B. Lee, K.S. Park, Y. Chong, M.Y. Yoon, S.J. Jeon, and D.E. Kim, Facilitation of polymerase chain reaction with thermostable inorganic pyrophosphatase from hyperthermophilic archaeon Pyrococcus horikoshii. Appl Microbiol Biotechnol 85 (2010) 807-12.

S.C. Peck, Analysis of protein phosphorylation: methods and strategies for studying kinases and substrates. Plant J 45 (2006) 512-22.

L. Prunetti, C.J. Reuter, N.L. Hepowit, Y. Wu, L. Barrueto, H.V. Miranda, K. Kelly, and J.A. Maupin-Furlow, Structural and biochemical properties of an extreme 'salt-loving' proteasome activating nucleotidase from the archaeon Haloferax volcanii. Extremophiles 18 (2014) 283-93.

C.J. Reed, H. Lewis, E. Trejo, V. Winston, and C. Evilia, Protein adaptations in archaeal extremophiles. Archaea 2013 (2013) 373275.

O.M. Richter, and G. Schafer, Purification and enzymic characterization of the cytoplasmic pyrophosphatase from the thermoacidophilic archaebacterium Thermoplasma acidophilum. Eur J Biochem 209 (1992) 343-9.

O.M. Richter, and G. Schafer, Cloning and sequencing of the gene for the cytoplasmic inorganic pyrophosphatase from the thermoacidophilic archaebacterium Thermoplasma acidophilum. Eur J Biochem 209 (1992) 351-5.

N. Saitou, and M. Nei, The neighbor-joining method: a new method for reconstructing phylogenetic trees. Mol Biol Evol 4 (1987) 406-25.

V.R. Samygina, V.M. Moiseev, E.V. Rodina, N.N. Vorobyeva, A.N. Popov, S.A. Kurilova, T.I. Nazarova, S.M. Avaeva, and H.D. Bartunik, Reversible inhibition of *Escherichia coli* inorganic pyrophosphatase by fluoride: trapped catalytic intermediates in cryo-crystallographic studies. J Mol Biol 366 (2007) 1305-17.

S. Tabor, and C.C. Richardson, DNA sequence analysis with a modified bacteriophage T7 DNA polymerase. Effect of pyrophosphorolysis and metal ions. J Biol Chem 265 (1990) 8322-8.

K. Tamura, G. Stecher, D. Peterson, A Filipski, and S. Kumar, MEGA6: Molecular Evolutionary Genetics Analysis version 6.0. Mol Biol Evol 30 (2013) 2725-9.

S. Uthandi, B. Saad, M. Humbard, and J. Maupin-Furlow, LccA, an archaeal laccase secreted as a highly stable glycoprotein into the extracellular medium by Haloferax volcanii. Appl Environ Microbiol 76 (2010) 733-743.

G.J. van Alebeek, J.T. Keltjens, and C. van der Drift, Purification and characterization of inorganic pyrophosphatase from

(56) References Cited

PUBLICATIONS

Methanobacterium thermoautotrophicum (strain delta H). Biochim Biophys Acta 1206 (1994) 231-9.

P.B. Vander Horn, M.C. Davis, J.J. Cunniff, C. Ruan, B.F. McArdle, S.B. Samols, J. Szasz, G. Hu, K.M. Hujer, S.T. Domke, S.R. Brummet, RB. Moffett, and C.W. Fuller, Thermo Sequenase DNA polymerase and T. acidophilum pyrophosphatase: new thermostable enzymes for DNA sequencing. Biotechniques 22 (1997) 758-62, 764-5.

T. Wakagi, T. Oshima, H. Imamura, and H. Matsuzawa, Cloning of the gene for inorganic pyrophosphatase from a thermoacidophilic archaeon, *Sulfolobus* sp. strain , and overproduction of the enzyme by coexpression of tRNA for arginine rare codon. Biosci Biotechnol Biochem 62 (1998) 2408-14.

D. Wendoloski, C. Ferrer, and M.L. Dyall-Smith, A new simvastatin (mevinolin)-resistance marker from Haloarcula hispanica and a new Haloferax volcanii strain cured of plasmid pHV2. Microbiology 147 (2001) 959-64.

H. Wilson, H. Aldrich, and J. Maupin-Furlow, Halophilic 20S proteasomes of the archaeon Haloferax volcanii Purification, characterization, and gene sequence analysis. J. Bacteriol. 181(1999)5814-5824.

M. Xiao, A. Phong, K.L. Lum, RA. Greene, P.R. Buzby, and P.Y. Kwok, Role of excess inorganic pyrophosphate in primer-extension genotyping assays. Genome Res 14 (2004) 1749-55.

G. Zhou, M. Kamahori, K. Okano, G. Chuan, K. Harada, and H. Kambara, Quantitative detection of single nucleotide polymorphisms for a pooled sample by a bioluminometric assay coupled with modified primer extension reactions (BAMPER). Nucleic Acids Res 29 (2001) E93.

G.H. Zhou, H. Shirakura, M. Kamahori, K. Okano, K. Nagai, and H. Kambara, A gelfree SNP genotyping method: bioluminometric assay coupled with modified primer extension reactions (BAMPER) directly from double-stranded PCR products. Hum Mutat 24 (2004) 155-63.

G. Zhou, D. Kowalczyk, M. Humbard, S. Rohatgi, and J. Maupin-Furlow, Proteasomal components required for cell growth and stress responses in the haloarchaeon Haloferax volcanii. J Bacteriol 190 (2008) 8096-8105.

\* cited by examiner

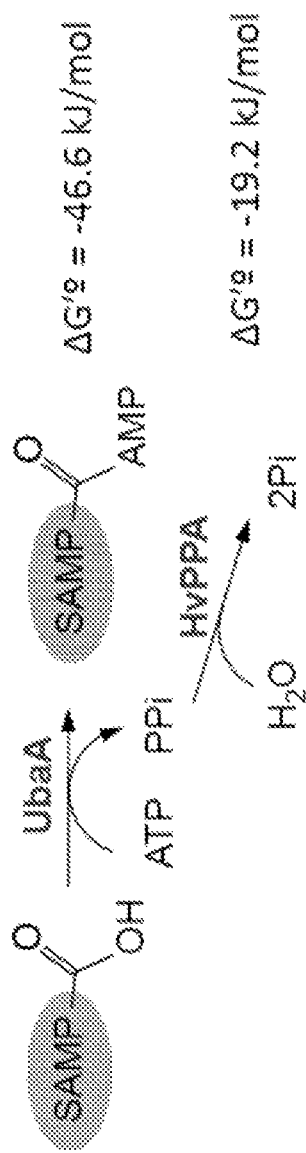
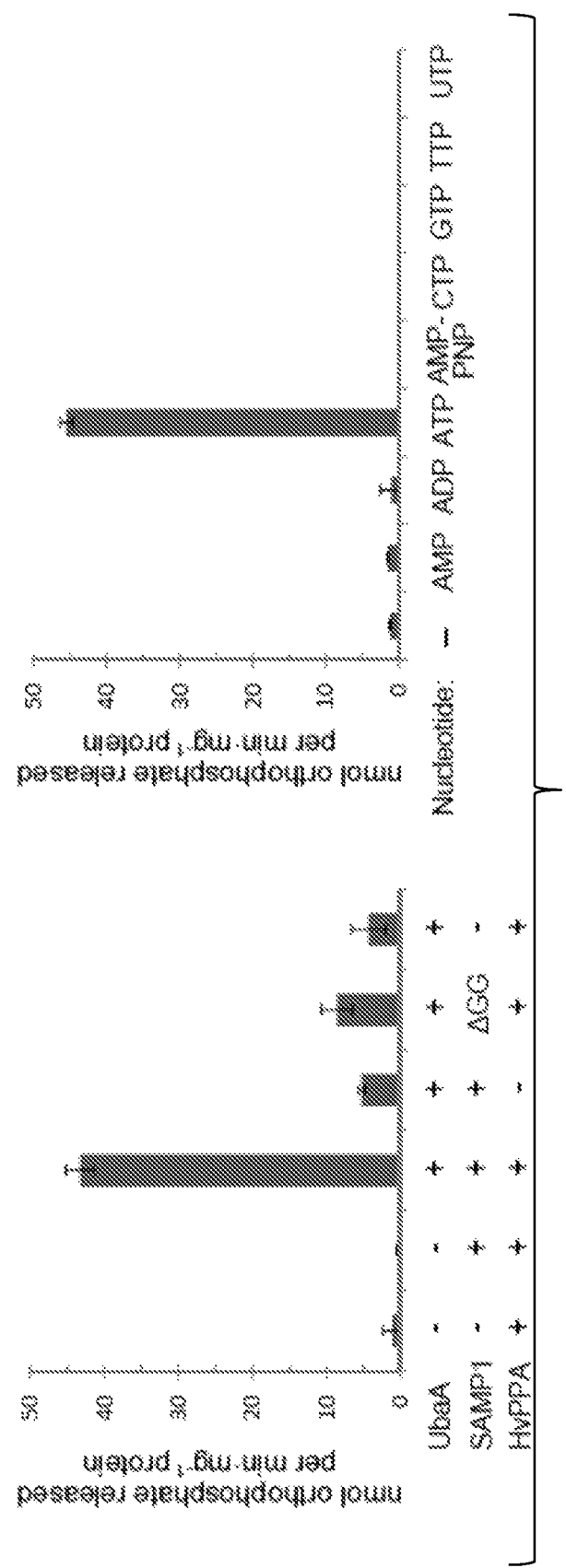
Figure 7A
Figure 7B

THERMOSTABLE HALOARCHAEAL INORGANIC PYROPHOSPHATASE

CROSS-REFERENCE TO RELATED APPLICATIONS

This application is the U.S. national stage application of International Patent Application No. PCT/US2016/057627, filed Oct. 19, 2016, which claims the benefit of U.S. Provisional Application Ser. No. 62/243,260, filed Oct. 19, 2015, the disclosures of which are hereby incorporated by reference in their entirety, including all figures, tables and amino acid or nucleic acid sequences.

The Sequence Listing for this application is labeled "Seq-List.txt" which was created on Oct. 19, 2016 and is 169 KB. The entire content of the sequence listing is incorporated herein by reference in its entirety.

This invention was made with government support under R01 GM057498 awarded by the National Institutes of Health and under DE-FG02-05ER15650 awarded by the Department of Energy. The government has certain rights in the invention.

BACKGROUND OF THE INVENTION

Inorganic pyrophosphatase (PPA) (EC 3.6.1.1) catalyzes the hydrolysis of the phosphoanhydride bond of inorganic pyrophosphate (PPi; $P_2O_7^{4-}$) to form two orthophosphates (Pi; $PO_4^{3-}$). PPi is a common by-product of biochemical reactions, for example, the biosynthesis of DNA, RNA, protein, peptidoglycan, lipids, cellulose, starch and other biopolymers as well as post-translational modification of proteins, for example, adenylation, uridylation and ubiquitylation of proteins.

The hydrolysis of PPi by PPA releases considerable amount of energy ($\Delta G'^\circ = -19.2$ kJ/mol) that can drive unfavorable biochemical transformations to completion. For example, during DNA polymerization, the 3'-hydroxyl group of the nucleotide that resides at the 3' end of the growing DNA strand serves as a nucleophile in the attack of the α phosphorus of the incoming deoxynucleoside 5'-triphosphate (dNTP), thus, releasing PPi. The reaction is endergonic ($\Delta G'^\circ = +2.1$ kJ/mol), and, under standard conditions, DNA polymerase alone would drive the conversion of DNA to dNTPs. Thus, the polymerization of DNA is highly dependent on PPA to hydrolyze the energy rich PPi to orthophosphate and drive the polymerization reaction.

Due to their ability to drive such reactions towards the production of PPi, PPAs are used in a wide variety of biotechnological applications. For example, PPAs prevent the accumulation of PPi during DNA sequencing and PCR reactions. PPAs are also used to remove contaminant PPi prior to single-base-extension to increase the yield of RNA synthesis by in vitro transcription and to enable the enzymatic synthesis of guanosine 5'-diphosphate (GDP)-sugars and derivatives. PPAs are also used to measure the kinetics of the reactions that release PPi as a by-product, such as SNP genotyping, RNA synthesis by viral RNA-dependent RNA polymerases and aminoacyl-tRNA synthetase activity. Typically, in these assays, PPA hydrolyzes PPi to 2Pi, which are readily detected by a colorimetric assay.

PPAs of the Class A type (IPR008162 family) are soluble, distributed in diverse organisms and include the thermostable PPAs of Archaea used to enhance the polymerization of DNA (i.e., PPAs of *Thermoplasma acidophilum*, *Pyrococcus horikoshii*, *Sulfolobus* sp., *Methanothermobacter thermautotrophicus* (*Methanobacterium thermoautotrophicum*), and *Thermococcus thioreducens*).

Currently used PPAs are inactivated in dose dependent manner by organic solvents, such as ethanol. Solvent tolerant PPAs allow novel synthetic chemistry, alter substrate specificity, ease product recovery, and reduce microbial contamination. Thus, there is a need to identify and produce solvent tolerant PPAs.

BRIEF SUMMARY OF THE INVENTION

The invention provides a PPA from a microorganism belonging to the halophilic archaea (haloarchaea), family Halobacteriaceae, hereinafter referred to as an HPPA. An embodiment of the invention provides an HPPA from *Haloferax volcanii*, hereinafter referred to as HvPPA. An embodiment of the invention provides a DNA construct comprising a nucleic acid encoding an HPPA, for example, HvPPA. Another embodiment of the invention provides a recombinant cell containing a nucleic acid encoding an HPPA. A further embodiment of the invention provides a method of expressing and purifying an HPPA.

Since the HPPA provided according to the invention is thermostable and active at moderately high temperature and/or low water activity, an embodiment of the invention provides a method of increasing the rate of a reaction which produces PPi, wherein the reaction is carried out at high temperature and/or low water activity, and wherein the method comprises adding an HPPA to the reaction mixture. Further embodiments of the invention provide an assay to detect PPi released during a reaction which produces PPi by adding an HPPA to the reaction mixture and measuring Pi produced from PPi. Certain embodiments of the invention also provide an assay to monitor the reaction which produces PPi. Even further embodiment of the invention provides an assay to monitor the reaction which produces PPi in the presence or the absence of an HPPA to determine the effect of HPPA on the reaction.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 7A-7B. on *Haloferax volcanii* inorganic phyrophosphatase (HvPPA) activity solvent and coupled adenylation assay at high temperature and low water activity. A) Schematic of the coupled assay. Adenylation of the ubiquitin-like SAMP by the E1-like enzyme (UbaA) was monitored by HvPPA mediated hydrolysis of the PPi ($P_2O_7^{4-}$) by-product to 2 Pi (2 moles $HPO_4^{2-}$) at 50° C. B) Generation of Pi correlated with the addition of ATP, UbaA, HvPPA and SAMP1 to the assay buffer. ΔGG, C-terminal diglycine residue deletion.

BRIEF DESCRIPTION OF SEQUENCES

Figure 1:
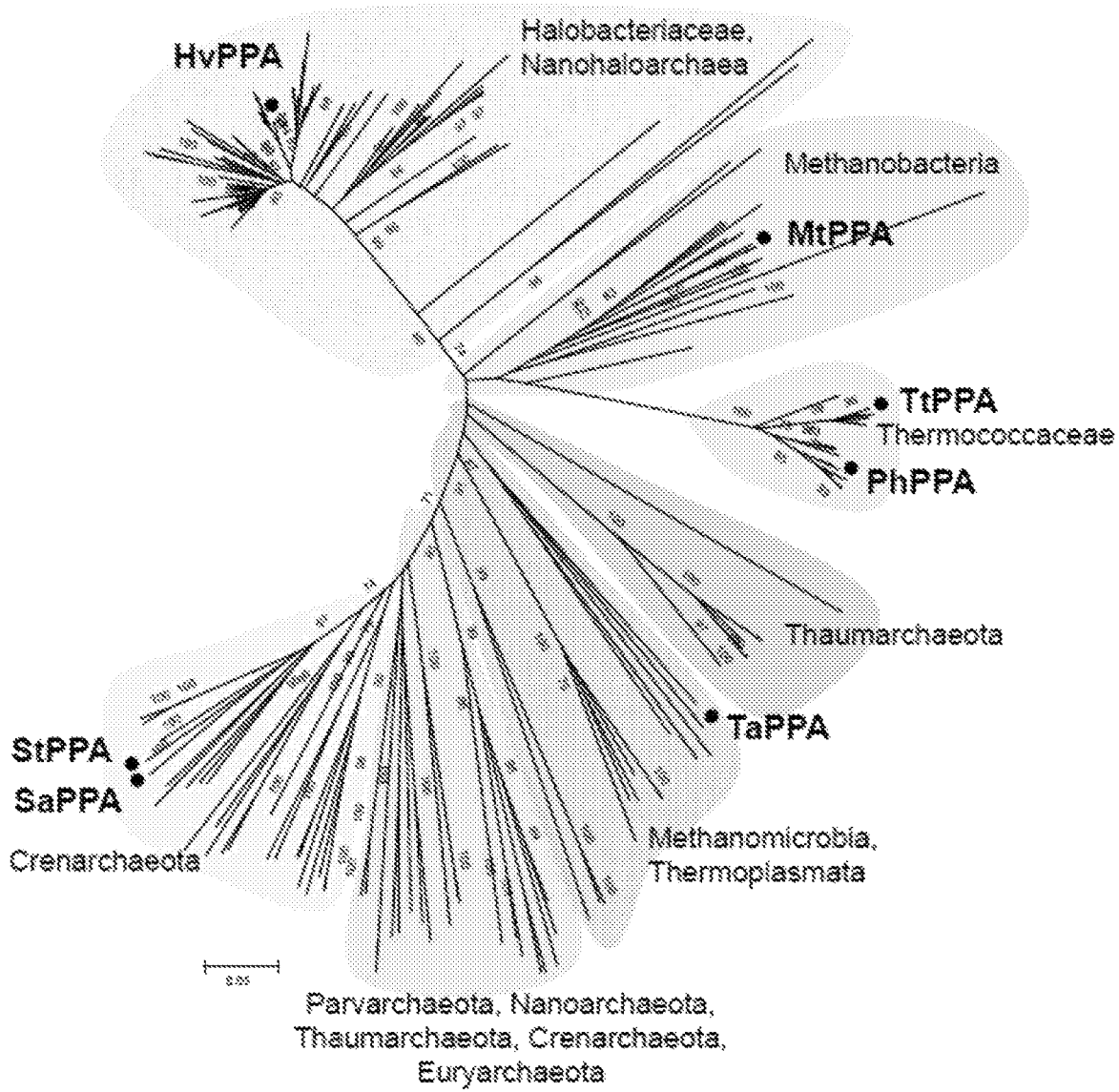
FIG. 1. Evolutionary relationships of archaeal PPA of the IPR008162 family. A phylogenetic tree of amino acid sequences was used to represent the evolutionary relationships of archaeal PPAs. Archaeal PPAs biochemically characterized are highlighted (●) including *Thermoplasma acidophilum* TaPPA (Ta0399), *Pyrococcus horikoshii* PhPPA (PH1907), *Sulfolobus* sp. StPPA (STK_05240) and SaPPA (Saci_0955), *Methanobacterium thermoautotrophicum* MtPPA (MTH_263), and *Thermococcus thioreducens* TtPPA (HOUSY5_9EURY) and *Hfx. volcanii* HvPPA (HVO_0729). The optimal tree with the sum of branch length of 15.65877199 is represented. The tree is drawn to scale, with branch lengths in the same units as those of the evolutionary distances used to infer the phylogenetic tree. See methods for details.

SEQ ID NO: 1: Nucleotide sequence encoding HvPPA.
SEQ ID NO: 2: Amino acid sequence of HvPPA.
SEQ ID NOs: 3 to 108: Amino acid sequences of various HPAA.
SEQ ID NO: 109: Amino acid sequence of FLAG-tag.
SEQ ID NO: 110: PPA NdeI forward.
SEQ ID NO: 111: PPA BlpI reverse.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

The invention demonstrates that a Class A type HPPA, for example, HvPPA, is thermostable and catalytically active in extreme conditions, for example, in the presence of 2-3 M salt (NaCl) and/or 25% (v/v) organic solvent (dimethylsulfoxide, N,N-dimethylformamide, ethanol or methanol). Accordingly, the invention provides an HPPA which is active in the conditions unfavorable to the activity of PPAs from other organisms. The invention also provides a method of facilitating a reaction which produces PPi, the method comprising adding an HPPA for example, HvPPA, in to the reaction mixture. Further, an embodiment of the invention provides an assay based on the HPPA mediated production of Pi from PPi to monitor and/or measure the kinetics of a reaction which produces PPi.

An embodiment of the invention provides HvPPA which is encoded by the sequence of SEQ ID NO: 1 and has the amino acid sequence of SEQ ID NO: 2.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). The present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

Nucleotide and proteins having the sequences that are at least 40%, 50%, 60%, 65%, 70%, generally at least 75%, 80%, 85%, 90%, 91%, 92%, 93%, 94%, to 95%, 96%, 97%, 98%, 99% or more sequence identity to the sequences described in the invention are also provided. The sequence identity can be determined by the sequence alignment programs that are well known in the art. Non-limiting examples of such sequence alignment program include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

In one embodiment, a nucleotide sequence has a sequence which is at least 40%, 50%, 60%, 65%, 70%, generally at least 75%, 80%, 85%, 90%, 91%, 92%, 93%, 94%, to 95%, 96%, 97%, 98%, 99% or more sequence identity to the sequence of SEQ ID NO: 1 is provided.

Similarly, a protein having the sequence which is at least 40%, 50%, 60%, 65%, 70%, generally at least 75%, 80%, 85%, 90%, 91%, 92%, 93%, 94%, to 95%, 96%, 97%, 98%, 99% or more sequence identity to the sequence of SEQ ID NO: 2 is also provided.

Further non-limiting examples an HPPA include proteins identified by UniProt entry numbers L5NDU6 (SEQ ID NO: 3), M0GG38 (SEQ ID NO: 4), M0I975 (SEQ ID NO: 5), M0FUM4 (SEQ ID NO: 6), M0FFB2 (SEQ ID NO: 7), M0FTS8 (SEQ ID NO: 8), M0GLF4 (SEQ ID NO: 9), M0HK17 (SEQ ID NO: 10), M0GRW8 (SEQ ID NO: 11), A0A0D6JT27 (SEQ ID NO: 12), M0HPW6 (SEQ ID NO: 13), M0IJ12 (SEQ ID NO: 14), M0J1D0 (SEQ ID NO: 15), M0I755 (SEQ ID NO: 16), M0FHY5 (SEQ ID NO: 17), M0DSG1 (SEQ ID NO: 18), I3R2F0 (SEQ ID NO: 19), A0A0F8AXZ4 (SEQ ID NO: 20), A0A063ZSK5 (SEQ ID NO: 21), V6DYW8 (SEQ ID NO: 22), M0AI50 (SEQ ID NO: 23), M0ACD9 (SEQ ID NO: 24), W0JSC4 (SEQ ID NO: 25), M0L713 (SEQ ID NO: 26), L9ZZ93 (SEQ ID NO: 27), M0B0N2 (SEQ ID NO: 28), L0JJS8 (SEQ ID NO: 29), M0CDJ7 (SEQ ID NO: 30), M0BJC3 (SEQ ID NO: 31), B9LS63 (SEQ ID NO: 32), M0E9P1 (SEQ ID NO: 33), D3SX83 (SEQ ID NO: 34), D2RW38 (SEQ ID NO: 35), M0C3G1 (SEQ ID NO: 36), M0JY31 (SEQ ID NO: 37), L9WPM3 (SEQ ID NO: 38), M0PRE6 (SEQ ID NO: 39), L9XRM4 (SEQ ID NO: 40), F8D7Q3 (SEQ ID NO: 41), M0NY18 (SEQ ID NO: 42), M0KHY3 (SEQ ID NO: 43), A0A0B5H0E2 (SEQ ID NO: 44), M0L599 (SEQ ID NO: 45), M0KLP2 (SEQ ID NO: 46), M0F4A3 (SEQ ID NO: 47), M0NU13 (SEQ ID NO: 48), M0ENH7 (SEQ ID NO: 49), M0IVY2 (SEQ ID NO: 50), M0DG34 (SEQ ID NO: 51), C7P1S8 (SEQ ID NO: 52), V5TIQ9 (SEQ ID NO: 53), G0HUD5 (SEQ ID NO: 54), M0EUQ2 (SEQ ID NO: 55), M0NWL5 (SEQ ID NO: 56), I7BTX4 (SEQ ID NO: 57), L9Z9R6 (SEQ ID NO: 58), L9Z019 (SEQ ID NO: 59), L9ZID4 (SEQ ID NO: 60), M0K9U1 (SEQ ID NO: 61), M0DQG4 (SEQ ID NO: 62), Q5UXJ0 (SEQ ID NO: 63), L0IDF8 (SEQ ID NO: 64), L9X8I7 (SEQ ID NO: 65), L0AKK7 (SEQ ID NO: 66), M0BBH8 (SEQ ID NO: 67), Q3IMH1 (SEQ ID NO: 68), L0K0M8 (SEQ ID NO: 69), M1XNP8 (SEQ ID NO: 70), E7QS08 (SEQ ID NO: 71), J3EYU6 (SEQ ID NO: 72), L9X0H4 (SEQ ID NO: 73), M0CLI0 (SEQ ID NO: 74), L9W889 (SEQ ID NO: 75), D8J8G3 (SEQ ID NO: 76), M0NAM6 (SEQ ID NO: 77), M0N5K4 (SEQ ID NO: 78), M0P5M8 (SEQ ID NO: 79), M0MFR0 (SEQ ID NO: 80), M0MGM0(SEQ ID NO: 81), W0K0R9 (SEQ ID NO: 82), E4NRZ6 (SEQ ID NO: 83), V4ZPA9 (SEQ ID NO: 84), U1QCV5 (SEQ ID NO: 85), V4Y944 (SEQ ID NO: 86), G2MJ96 (SEQ ID NO: 87), M0CVD7 (SEQ ID NO: 88), C7NMR7 (SEQ ID NO: 89), M0M2R7 (SEQ ID NO: 90), F7PQH1 (SEQ ID NO: 91), R4W5L5 (SEQ ID NO: 92), V4HJG7 (SEQ ID NO: 93), U1PEB6 (SEQ ID NO: 94), U1QT16 (SEQ ID NO: 95), A0A0F7PBR3 (SEQ ID NO: 96), Q18KT4 (SEQ ID NO: 97), G0LHI3 (SEQ ID NO: 98), B0R2Z8 (SEQ ID NO: 99), Q9HSF3 (SEQ ID NO: 100), U1PVH2 (SEQ ID NO: 101), U1NPX9 (SEQ ID NO: 102), U1NUP6 (SEQ ID NO: 103), V4YFB8 (SEQ ID NO: 104), U2YXF9 (SEQ ID NO: 105), U1PS97 (SEQ ID NO: 106), V4XHA0 (SEQ ID NO: 107) or U1P365 (SEQ ID NO: 108). Additional examples of an HPPA are well known to a person of ordinary skill in the art and such embodiments are within the scope of the invention.

Certain embodiment of the invention provide a DNA construct (sometimes referred to as nucleotide constructs or vectors) comprising a nucleotide encoding an HPPA. A typical vector contains an origin of replication, a promoter which drives the expression of an operably connected nucleotide and one or more selection markers. Vectors appropriate for use according to the instant invention are well known to a person of ordinary skill in the art and such embodiments are within the purview of the invention.

One embodiment of the invention provides a cell, for example, bacterial cell, archaeal cell, fungal cell, plant cell or animal cell, containing a nucleotide encoding an HPPA. The nucleotide encoding an HPPA can be in a vector or incorporated in to the genome of the cell. In one embodiment, the invention provides a cell, for example, bacterial cell, archaeal cell, fungal cell, plant cell or animal cell, containing a nucleotide encoding HvPPA, either in a plasmid or incorporated in to the genome of the cell.

A further embodiment of the invention provides a method of expressing an HPPA in a cell, for example, bacterial cell, archaeal cell, fungal cell, plant cell or animal cell, the method comprising transforming the cell with a nucleotide encoding an HPPA, culturing the cell under conditions which allows the expression of the HPPA, and optionally, purifying the HPPA from the culture. In one embodiment, the cell expressing an HPAA is *Escherichia coli*.

In one embodiment, the purification of an HPPA is facilitated by conjugating the HPPA with a protein or peptide tag. Non-limiting examples of a protein or peptide tag which facilitates the purification of the HPPA protein include 6× histidine ($His_6$), maltose binding protein, calmodulin binding peptide, covalent yet dissociable NorpD peptide, STREP-TAG™ (streptavidin binding peptide), FLAG-Tag (amino acid sequence: Asp-Tyr-Lys-Asp-Asp-Asp-Asp-Lys (SEQ ID NO: 109), heavy chain of protein C or Glutathione S-transferase. Additional examples of protein or peptide tags useful for purification of HPPA are well known to the person of ordinary skill in the art and such embodiments are within the purview of the invention.

Various methods of expressing and purifying a protein in a bacterial cell, archaeal cell, fungal cell, plant cell or animal cell are well known to a person of ordinary skill in the art and such embodiments are within the purview of the invention.

An embodiment of the invention further provides a method of driving a reaction which produces PPi towards the production of PPi. For the purpose of this invention, the phrase "driving a reaction towards the production of PPi" indicates increasing the rate of the reaction in the direction of the production of PPi. For example, if a reaction involving the production of PPi is reversible, the reaction can lead to the production of PPi or to the utilization of PPi. In such condition, "driving a reaction towards the production of PPi" indicates increasing the rate of the reaction in the direction which leads to the production of PPi.

The method of driving a reaction which produces PPi towards the production of PPi comprises adding an HPPA to the reaction mixture of a first reaction which produces PPi, wherein the added HPPA catalyzes the hydrolysis of PPi to Pi and the removal of PPi from the reaction mixture increases the rate of the first reaction in the direction to produce more PPi. In an embodiment, the first reaction which produces PPi is an enzymatic reaction. In a further embodiment, the first reaction which produces PPi takes place under the conditions of high temperature and/or low water activity.

For the purpose of this invention, the term "moderately high temperature" indicates that the temperature is typically favorable for thermophilic enzymes. Temperatures favorable for a thermophilic enzyme is about 40° C. to about 100° C., about 40° C. to about 80° C., about 40° C. to about 60° C., about 40° C. to about 50° C. or about 42° C.

For the purpose of the invention, the term "water activity" refers to the amount of water associated with an enzyme in a reaction mixture rather than the total amount of water in the reaction mixture. Therefore, the term "low water activity" refers to the conditions where the amount of water associated with an enzyme in a reaction mixture is low compared to the total amount of water in the reaction mixture. The conditions which affect water activity include, but are not limited to, salt concentration and/or the presence/absence and the concentration of organic solvents. Typically, water activity is inversely proportional to the concentrations of salts and/or organic solvents. Therefore, a reaction mixture containing higher concentrations of salts and/or organic solvents has lower water activity and vice versa.

For the purpose of this invention, the phrase "high salt concentration" refers to salt concentration which is typically unfavorable for non-halophilic enzymes. Halophilic enzymes are the enzymes that are active in the presence of high salt concentration, for example, about 1M to about 5M. Accordingly, "high salt concentration" refers to a salt concentration of about 1M to about 5M, about 1.5 M to about 4M, about 2M to about 3M, or about 2.5 M.

For the purpose of this invention, the phrase "high organic solvent concentration" refers to organic solvent concentration of about 10% to about 50%, about 15% to about 40%, about 20% to about 30%, or about 25%. The organic solvents typically used in a reaction mixture include dimethylsulfoxide (DMSO), N,N-dimethylformamide (DMF), ethanol or methanol. Additional examples of organic solvents used in a reaction are well known to a person of ordinary skill in the art and such embodiments are within the purview of the current invention. Accordingly, "the conditions of low water activity" refer to a salt concentration of about 1M to about 5M, about 1.5 M to about 4M, about 2M to about 3M, or about 2.5 M and/or an organic solvent concentration of about 10% to about 50%, about 15% to about 40%, about 20% to about 30%, or about 25%. In certain embodiments, the reaction which produces PPi is performed at moderately high temperature, for example, about 40° C. to about 100° C., about 40° C. to about 80° C., about 40° C. to about 60° C., about 40° C. to about 50° C. or about 42° C. In a further embodiment, the reaction which produces PPi is performed under low water activity. In an even further embodiment, the reaction which produces PPi is performed under moderately high temperature and/or low water activity.

An HPPA, for example, HvPPA, is active under conditions of low water activity, thermostable at high temperatures (such as about 50° C. to about 100° C., about 60° C. to about 90° C., about 70° C. to about 80° C., or about 75° C.) and enzymatically active at moderately high temperatures (temperatures of about 40° C. to about 100° C., about 40° C. to about 80° C., about 40° C. to about 60° C., about 40° C. to about 50° C. or about 42° C.). Accordingly, the invention provides a method of driving a reaction which produces PPi in the direction of the production of PPi, the method comprising adding an HPPA to the reaction mixture for the reaction which produces PPi, wherein the reaction which produces PPi is carried out under the conditions of low water activity, moderately high temperatures and/or after enzyme exposure to high temperatures.

In an embodiment, the HPPA is HvPPA having the amino acid sequence of SEQ ID NO: 2. In another embodiment, the HPPA has the amino acid sequence selected from SEQ ID NOs: 3 to 108.

In one embodiment, the enzymatic reaction which produces PPi is the biosynthesis of DNA, RNA, protein, peptidoglycan, lipids, cellulose, starch and other biopolymers, post-translational modification of proteins including adenylation, uridylation and ubiquitylation, SNP genotyping, RNA synthesis by viral RNA-dependent RNA polymerases and aminoacyl-tRNA synthetase activity. Typically, any enzymatic reaction which produces PPi comprises hydrolysis of nucleoside triphosphate, for example, adenosine triphosphate (ATP), guanosine triphosphate (GTP), cytidine triphosphate (CTP), 5-methyluridine triphosphate ($m^5$UTP), and uridine triphosphate (UTP). A non-limiting list of enzymatic reactions that produce PPi are provided in Jukka K. Heinonen, Biological Role of Inorganic Pyrophosphate, New York, Spring Science+Business media, 2001, particularly, in Chapter 1, Tables 1.1 and 1.2 on pages 1-9, the contents of which are herein incorporated by reference in their entirety. Additional examples of reactions which produce PPi, particularly, enzymatic reactions which produce PPi, are well known to a person of ordinary skill in the art and such embodiments are within the purview of the invention. The reactions will be conducted, typically, under conditions that include moderately high temperatures (such as temperatures of about 40° C. to about 100° C., about 40° C. to about 80° C., about 40° C. to about 60° C., about 40° C. to about 50° C. or about 42° C.).

A further embodiment of the invention provides a composition comprising a reaction mixture for the reaction which produces PPi, the composition further comprising an HPPA. In an embodiment, the reaction which produces PPi is an enzymatic reaction.

In certain embodiments, the enzymatic reaction mixture for the enzymatic reaction which produces PPi comprises one or more substrates, an enzyme which catalyzes the production of PPi and/or one or more co-factors for the enzyme. Non-limiting examples of substrates include proteins, single stranded polynucleotide, double stranded polynucleotide, carbohydrates, lipids, ATP, GTP, CTP, UTP or m5UTP. Non-limiting examples of cofactors include $Mg^{2+}$, $Mn^{2-}$, $Zn^{2+}$ and $Co^{2+}$. Additional examples of substrates and co-factors are well known to a person of ordinary skill in the art and such embodiments are within the purview of the invention.

In one embodiment, the invention provides a composition comprising a reaction mixture for a reaction which produces PPi and HvPPA which has the amino acid sequence of SEQ ID NO: 2. In another embodiment, the invention provides a composition comprising a reaction mixture for the reaction which produces PPi and an HPPA having the amino acid sequence selected from SEQ ID NOs: 3 to 108.

A further embodiment of the invention provides an assay of determining the reaction kinetics for a reaction which produces PPi, the method comprising the steps of:

a. conducting the reaction which produces PPi,
b. periodically separating an aliquot of the reaction mixture from the enzymatic reaction which produces PPi and immediately subjecting the aliquots to a condition which stops the reaction which produces PPi to obtain a plurality of aliquots corresponding to various time points for the reaction which produces PPi,
c. introducing sufficient amount of an HPPA to each of the plurality of the aliquots,
d. incubating the HPPA with each of the plurality of aliquots under suitable conditions and for sufficient amount of time to allow the HPPA to convert all of the PPi present in the aliquot in to Pi,
e. determining the amount of Pi present in each of the plurality of aliquots, and
f. determining the reaction kinetics of the reaction which produces PPi based on the amount of Pi in each of the plurality of aliquots. The reaction that produces PPi is conducted, typically, under moderately high temperatures (temperatures of about 40° C. to about 100° C., about 40° C. to about 80° C., about 40° C. to about 60° C., about 40° C. to about 50° C. or about 42° C.).

In one embodiment, the HPPA is HvPPA having the amino acid sequence of SEQ ID NO: 2. In another embodiment the HPPA has the amino acid sequence selected from SEQ ID NOs: 3 to 108.

In certain embodiments, the condition which stops the reaction which produces PPi includes exposure to a temperature at which the enzyme producing PPi is inactivated (temperatures such as about 50° C. to about 100° C., about 60° C. to about 90° C., about 70° C. to about 80° C., or about 75° C. or about 100° C. for a period of 2 to 24 hours), addition of an inhibitor of the enzyme producing PPi or addition of a reagent which stops the reaction producing PPi. Additional methods of stopping a reaction are well known in the art and such embodiments are within the purview of the current invention.

In a certain embodiment, the assay used to detect the concentration of Pi present in each of the plurality of aliquots is a colorimetric assay, for example, malachite green based assay for detecting Pi. Additional examples of assays to detect the concentration of Pi are well known to a person of ordinary skill in the art and such embodiments are within the purview of the current invention.

A further embodiment of the invention provides an assay for monitoring the reaction and/or determining the reaction kinetics for a reaction which produces PPi in the presence and/or the absence of an HPPA, the method comprising the steps of:

a. conducting the reaction which produces PPi in the presence of the HPPA at moderately high temperatures,
b. conducting the reaction which produces PPi in the absence of the HPPA at moderately high temperatures,
c. periodically separating aliquots from the reaction mixtures in the presence or the absence of the HPPA and immediately subjecting the aliquots to a condition which stops the reaction which produces PPi to obtain a plurality of aliquots corresponding to various time points for the reactions which produces PPi in the presence or the absence of the HPPA,
d. determining the amount of Pi present in each of the plurality of aliquots, and
e. based on the amount of Pi present in each of the plurality of aliquots, determining the reaction kinetics for the reaction which produces PPi in the presence or the absence of the HPPA, and
f. determining the effect of the presence of the HPPA on the reaction producing PPi.

In one embodiment, the HPPA is HvPPA having the amino acid sequence of SEQ ID NO: 2. In another embodiment the HPPA has the amino acid sequence selected from SEQ ID NOs: 3 to 108.

In certain embodiments, the condition which stops the reaction which produces PPi includes exposure to the temperature at which the enzyme producing PPi is inactivated (temperatures such as about 50° C. to about 100° C., about 60° C. to about 90° C., about 70° C. to about 80° C., or about 75° C. or about 100° C. for a period of 2 to 24 hours), addition of an inhibitor of the enzyme producing PPi or addition of a reagent which stops the reaction producing PPi. Additional methods of stopping a reaction are well known in the art and such embodiments are within the purview of the current invention.

In a certain embodiment, the amount of Pi present in each of the plurality of aliquots is determined using a colorimetric assay, for example, malachite green based assay. Additional examples of determining the amount of Pi are well known to a person of ordinary skill in the art and such embodiments are within the purview of the current invention.

Materials and Methods

Materials

Chemicals were purchased from Sigma-Aldrich (St. Louis, Mo.) or Fisher Scientific (Atlanta, Ga.). Phusion and Taq DNA polymerases, restriction endonucleases and T4 DNA ligase were purchased from New England Biolabs (Ipswich, Mass.). Desalted oligonucleotides were purchased from Integrated DNA Technologies (Coralville, Iowa). Agarose used for routine analysis of DNA was purchased from Bio-Rad Laboratories (Hercules, Calif.).

Strains and Media

Strains used in this study are listed in Table 1. *E. coli* TOP10 was used for routine recombinant DNA analysis. *E. coli* GM2163 was used for preparation of plasmid DNA prior to transformation of *Hfx. volcanii* H26 by standard methods. *E. coli* strains were grown at 37° C. in Luria-Bertani (LB) medium supplemented with ampicillin (Amp at 0.1 mg/ml) as needed. *Hfx. volcanii* strains were grown at 42° C. in ATCC 974 medium supplemented with novobiocin (+Nv, 0.1 µg/ml$^{-1}$) as needed. Cells were grown in liquid cultures with rotary shaking at 200 rpm and on solid medium (1.5% [w/v] agar plates). Growth was monitored by measuring $OD_{600}$ [where 1 $OD_{600}$ unit equals approximately $1 \times 10^9$ colony forming units (CFU)/ml$^{-1}$].

TABLE 1

Purification of HvPPA from *Hfx. volcanii* (H26-pJAM2920).

| Fraction | Total Protein (mg) | Total Activity (U ± SD) | SP act U · Mg$^{-1}$ ± SD) | Yield (%) | Purification (fold enrichment) |
|---|---|---|---|---|---|
| Lysate | 1680 | 356 ± 30 | 0.21 ± 0.02 | 100 | 1 |
| HisTrap HP | 22.5 | 180 ± 14 | 7.98 ± 0.61 | 51 | 38 |
| Superdes 200 | 0.56 | 42 ± 0.26 | 75.3 ± 0.47 | 12 | 357 |

PPA activity monitored in Tris-salt buffer at 37° C. and pH 8.5 with 0.1 mM PPi for 10 min. U, units defined as µmol product/min. SD, standard deviation of three experiments.

DNA Manipulations

Plasmids and primers used in this study are listed in Table 2. Primers 1 and 2 were used for PCR-based amplification of the HvPPA gene with *Hfx. volcanii* H26 genomic DNA as template. The 0.55 kb PCR product was ligated into the NdeI to BlpI sites of pJAM503 to generate plasmid pJAM2920 for expression of HvPPA with an N-terminal poly-histidine tag (His$_6$-HvPPA) linked with a thrombin-cleavage site. Plasmid DNA was isolated by QIAprep Spin Miniprep kit (Qiagen, Valencia, Calif.). PCRs were according to standard methods using an iCycler (BioRad Laboratories). Genomic DNA was extracted from *Hfx. volcanii* cells by boiling colonies resuspended in ddH$_2$O or by DNA spooling. Phusion DNA polymerase was used for high-fidelity PCR-based cloning. Taq DNA polymerase was used for colony screening. DNA fragments were separated by 0.8-2% (w/v) agarose gel electrophoresis (90 V, 30-45 min) in TAE buffer [40 mM Tris, 20 mM acetic acid, 1 mM ethylenediaminetetraacetic acid (EDTA), pH 8.0]. Gels were stained with ethidium bromide at 0.25 µg/ml and visualized with a Mini visionary imaging system (FOTODYNE, Hartland, Wis.). Hi-Lo DNA molecular weight markers (Minnesota Molecular, Minneapolis, Minn.) were used for comparison. DNA fragments were isolated directly from PCR by MinElute PCR purification (Qiagen) or from 0.8% (w/v) SeaKem GTG agarose (FMC Bioproducts, Rockland, Me.) gels in TAE buffer at pH 8.0 using the QIAquick gel extraction kit (Qiagen) as needed. The fidelity of DNA plasmid constructs was verified by DNA Sequencing.

TABLE 2

Strains, plasmids and primers used in this study[a].

| Strain, plasmid or primer | Description | Source or reference |
|---|---|---|
| *E. coli* TOP10 | F$^-$ recA1 endA1 hsdR17(rK$^-$ mK$^+$) supE44 thi-1 gyrA relA1 | Invitrogen |
| *E. coli* GM2163 | F$^-$ ara-14 leuB6 fhuA31 lacY1 tsx78 glnV44 galK2 galT22 mcrA dcm-6 hisG4 rfbD1 rpsL136 dam13::Tn9 xylA5 mtl-1 thi-1 mcrB1 hsdR2 | New England Biolabs |
| *Hfx. volcanii* DS70 | wild-type isolate DS2 cured of plasmid pHV2 | [60] |
| *Hfx. volcanii* H26 | DS70 ΔpyrE2 | [61] |
| Plasmid pJAM503 | Ap$^r$; NV$^r$; *Hfx. volcanii-E. coli* shuttle vector with coding sequence for N-terminal His$_6$ tag | [38] |
| Plasmid pJAM292 | Ap$^r$; Nv$^r$; pJAM503-derived, His$_6$-HvPPA | This study |
| Primer 1: PPA NdeI FW | 5'-taCATATGGTGAACCTCTGGGAAGATATGGAG-3' (SEQ ID NO: 110) | This study |
| Primer 2: PPA BlpI RV | 5'-CTACGAAGAGAACTTCGCGTAAgcgaGCTGAGCta-3' (SEQ ID NO: 111) | This study |

[a]Ap$^r$, ampicillin resistance; Nv$^r$, novobiocin resistance.

Purification of HvPPA

HvPPA (HVO_0729, UniProt: D4GT97) was expressed with an N-terminal poly-histidine tag (His$_6$) in *Hfx. volcanii* H26-pJAM2920 (Table 1). *Hfx. volcanii* cells were grown to stationary phase (OD$_{600}$ of 3-3.5) (4×1-liter cultures in 2.8-liter Fernbach flasks) and harvested by centrifugation (10-15 min at 9,200× g and 25° C.). Cell pellets were resuspended at 5 ml per g wet weight cells in Tris-salt buffer (20 mM Tris-HCl, pH 7.5, 2 M NaCl and 2.5 mM MgCl$_2$) supplemented with 40 mM imidazole and 1 mini-tablet protease inhibitor cocktail (Roche product no. 05892791001) per 10 ml buffer. Cells were lysed by passing through a French Press (three times at 20,000 psi). Whole cell lysate was clarified by centrifugation (twice for 30 min at 9,200× g and 4° C.) and sequential filtration using 0.8 µm and 0.2 µm cellulose acetate filters (Thermo Scientific Nalgene). Clarified cell lysate was applied to a HisTrap HP column (5 ml, 17-5248-01, GE Healthcare) pre-equilibrated and washed in 100 ml of Tris-salt buffer with 40 mM imidazole. Fractions containing HvPPA were eluted in Tris-salt buffer with a 25 ml gradient from 40 mM to 500 mM imidazole. Fractions were tested for activity and dialyzed overnight with a buffer change after four hours against Tris-salt buffer containing 2.5 mM MgCl$_2$ and 1 mM DTT, and concentrated by centrifugal filtration using an Amicon Ultra-x mL 10K device (EMD Millipore). HvPPA was further purified by size exclusion chromatography (SEC) in which protein (500 µl at 14.5 mg/ml) was applied at a flow rate of 0.3 ml/min to a Superdex 200 10/300 GL column (GE Healthcare) equilibrated in Tris-salt buffer supplemented with fresh 1 mM DTT. HvPPA fractions eluting at 14.8 ml (hexamer) and 15.9 ml (trimer) were further purified using a similar SEC strategy. Purity of HvPPA was assessed by Coomassie Blue stained SDS-PAGE gels and PPi activity assay. Molecular mass standards used for analytic SEC were blue dextran (for void volume), β-amylase, cytochrome C, bovine serum albumin, and alcohol dehydrogenase (Sigma Aldrich, #MWGF200-1KT). HvPPA fractions were pooled and stored at 4° C.

PPi Assay

HvPPA-mediated hydrolysis of PPi to Pi was determined spectrophotometrically. Reagents were in nanopure water (Barnstead/Thermolyne Nanopure lab water system). Sodium pyrophosphate tetrabasic decahydrate (Sigma Aldrich) was used as a substrate. For kinetic measurements, reaction mixtures (500 µl total) contained 0.5-1 µg HvPPA and 1 mM PPi in high-salt buffer (3 M NaCl and 20 mM Tris-HCl, pH 8.5). Reactions were incubated at 42° C. for 1-3 min. Orthophosphate levels were determined by malachite green assay. Briefly, 2.5 ml of 14% (w/v) (NH$_4$)$_2$MoO$_4$ and 0.2 ml of 11% (v/v) TWEEN 20 ® (Polyoxyethylene sorbitan monolaurate) were added into a 10-ml color reagent I (containing 1.67 ml conc. sulfuric acid, 8.33 ml nanopure H$_2$O, and 12.22 mg malachite green). In triplicate, 50 µl of the color reagent was mixed with 200 µl of the reaction mixture and incubated at room temperature for 10 min. The formation of (MG$^+$)(H$_2$PMo$_{12}$O$_{40}$) (where MG$^+$ represents ionized malachite green) was monitored at A$_{630}$. A less sensitive malachite green assay was also used in which reaction aliquots (50 µl) were mixed with 250 µl color reagent II and 10 µl 1.5% (v/v) TWEEN 20 ® (Polyoxyethylene sorbitan monolaurate) in triplicate; product formation was immediately monitored at A$_{650}$. Color reagent II was generated by mixing 1 volume of 4.2% (w/v) (NH$_4$)$_2$MoO$_4$ in 5 N HCl with 3 volumes of 0.2% (w/v) malachite green; after 30 minutes, the solution was filtered with a 0.45 µm filter and stored at room temperature. Freeze-dried KH$_2$PO$_4$ was used as the standard. Assay mixtures with PPi minus HvPPA were used for individual background subtraction. All proteins used in this assay were buffer-exchanged with Tris-high-salt buffer in nanopure H$_2$O prior to use. All experiments were performed in triplicate and the mean±standard deviation (S.D.) was calculated.

Coupled Assay of Ubiquitin-Like Protein Adenylation

UbaA-mediated hydrolysis of ATP to AMP and PPi in the presence of the ubiquitin-like SAMP1 was monitored by coupled assay with HvPPA. Proteins were buffer-exchanged with HEPES-salt buffer in Nanopure H$_2$O prior to use. Reaction mixtures (500 µl total) containing 20 µM UbaA, 20 µM SAMP1, 0.5 µM HvPPA, 2.5 mM nucleotide, 2.5 mM MgCl$_2$, 50 µM ZnCl$_2$ in high-salt buffer (2 M NaCl and 50 mM HEPES in Nanopure H$_2$O, pH 7.5) were incubated at 37-42° C. for 1 h. Nucleotides were ATP, AMP, ADP, AMP-PNP, CTP, GTP, TTP and UTP. Proteins were removed by Ultracel-3 centrifugal filtration prior to determining orthophosphate levels by malachite green assay modified as described above. Assay mixtures with nucleotide alone were used for individual background subtraction.

Protein Concentration Assay

The molar protein concentration was calculated using absorption at 280 nm and extinction coefficient 26,025/M·cm (with the assumption that all cysteines were cystines). These values were comparable to protein concentration calculated by the Bradford method using bovine serum albumin (BSA; ThermoScientific) as the standard.

SDS-PAGE and Immunoblotting

Proteins were separated by reducing SDS-PAGE according to the Laemmli system. His-tagged HvPPA was analyzed by immunoblotting using a monoclonal unconjugated α-his IgG$_2$ antibody from mouse (27-4710-01 GE Healthcare) and alkaline phosphatase-linked goat anti-mouse IgG antibody (A5153 Sigma Aldrich). Immunoreactive antigens were detected by chemiluminescence using CDP-Star (Applied Biosystems), as the alkaline phosphatase substrate, and X-ray film (Research Products Intl. Corp.).

Dendrogram Analysis

Evolutionary analyses were conducted in MEGA6. The evolutionary history of archaeal PPAs was inferred using the Neighbor-Joining method. The evolutionary distances were computed using the p-distance method and were in the units of the number of amino acid differences per site. The analysis involved 225 amino acid sequences. All ambiguous positions were removed for each sequence pair. There were a total of 263 positions in the final dataset.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. Percentages are by total activity, by amino acid sequence and/or by weight. All solvent mixture proportions are by volume unless otherwise noted.

EXAMPLE 1

Haloarchaeal PPA Homologs are Distinct from Other PPA

The evolutionary relationships of archaeal PPAs of the Class A type (IPR008162 family) were analyzed by hierarchical clustering to identify new PPAs with distinct features in amino acid sequence that may correlate with novel biochemical properties. In contrast to PPAs of other families/domains (i.e., IPR004131, IPR022934, IPR004097 and IPR023733), the Class A type PPAs are soluble and the most widespread among extreme organisms such as Archaea. By this approach, haloarchaeal PPA homologs of the Class A type were found to cluster to a single node suggesting a close evolutionarily relationship among these proteins that was distinct from other PPAs (FIG. 1). Included in the tight cluster of haloarchaeal PPA homologs was HvPPA.

Figure 2A:
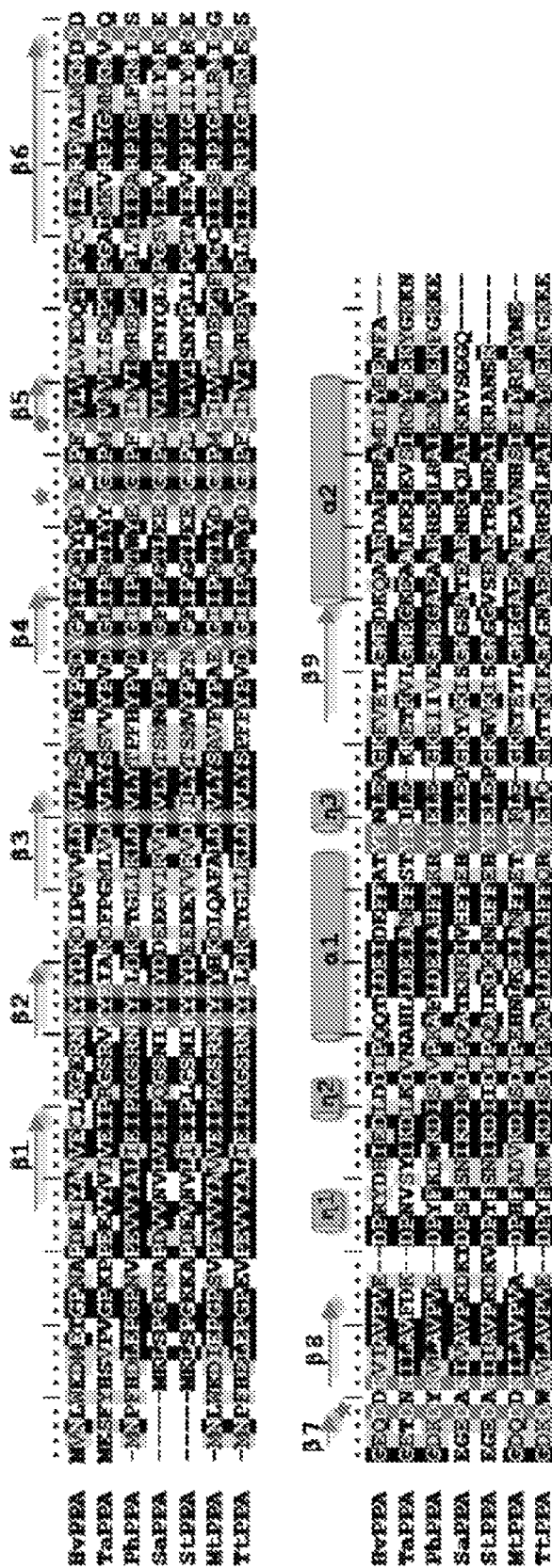
FIGS. 2A-2C. Structural comparison of Class A type PPA. A) Multiple amino acid sequence alignment of PPAs. Highlighted are identical (black), functionally similar (grey), Cys-$X_{63}$-Cys motif (blue) and conserved active site (red) residues. Predicted α-helix and β-sheet structures and Asp residues (*) coordinating $Mg^{2-}/Mn^{2+}$ are indicated above the alignment. Abbreviations are as in FIG. 1. B) 3D-structural comparison of PPAs. 3D-structural model of HvPPA (blue ribbon) compared to the X-ray crystal structures of PhPPA (PDB:1UDE) (tan ribbon), SaPPA (PDB:1QEZ), TtPPA (PDB:3R5U) and *Saccharomyces cerevisiae* ScPPA (PDB:1E9G). $Mn^{2+}$ ions (purple ball), phosphate ions (orange and red stick), and water (red ball) ligands are overlaid onto the 3D model. C-terminal (Ct) and N-terminal (Nt) residues are indicated. HvC24 and HvC85 are cysteine residues conserved in all haloarchaeal PPAs. Conserved active site residues analogous to ScPPA include: HvK31 (ScK56), HvE33 (ScE58), HvR45 (ScR78), HvY57 (ScY93), HvD67 (ScD115), HvD69 (ScD117), HvD72 (ScD120), HvD99 (ScD147), HvD104 (ScD152), HvK106 (ScK154), HvY141 (ScY192) and HvK142 (ScK193). HvD67, HvD72 and HvD104 are predicted to coordinate the $Mg^{2+}$ and $Mn^{2+}$ ions. HvPPA 3D-structure was modeled by Phyre2 intensive-mode at a confidence of >90% accuracy for 175 out of 177 residues (99%). C) Comparison of electrostatic potential of PPAs. Electrostatic potential as represented by Coulombic Surface Coloring with the unit of the potential colored in a range of values −10 (red), 0 (white), and 10 (blue) kcal/mol*e using Chimera v 1.7.
Figure 2B:
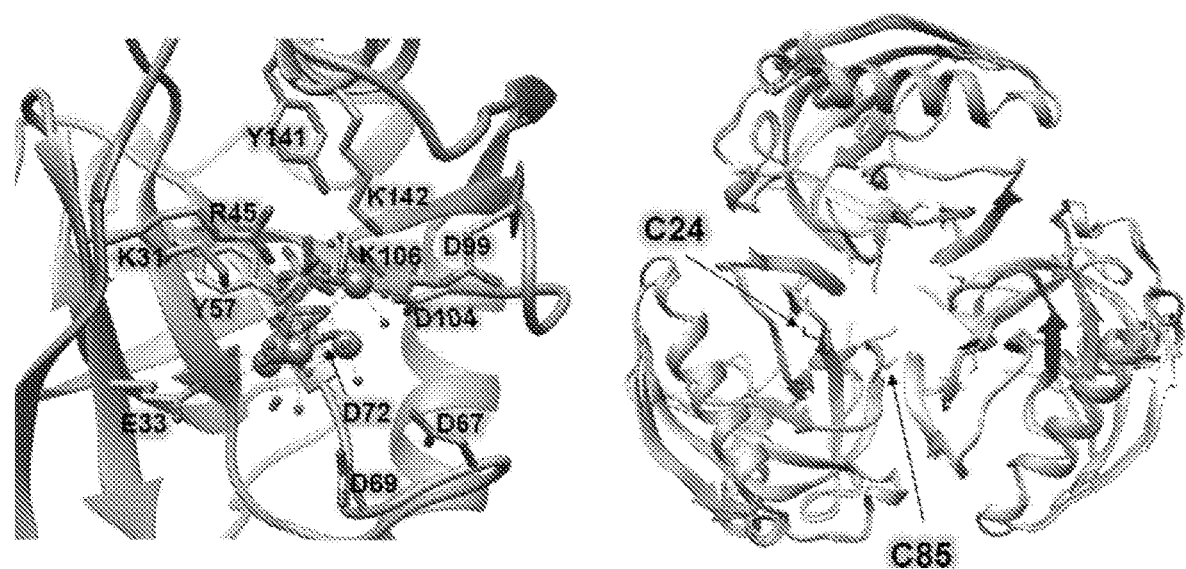
Figure 2C:
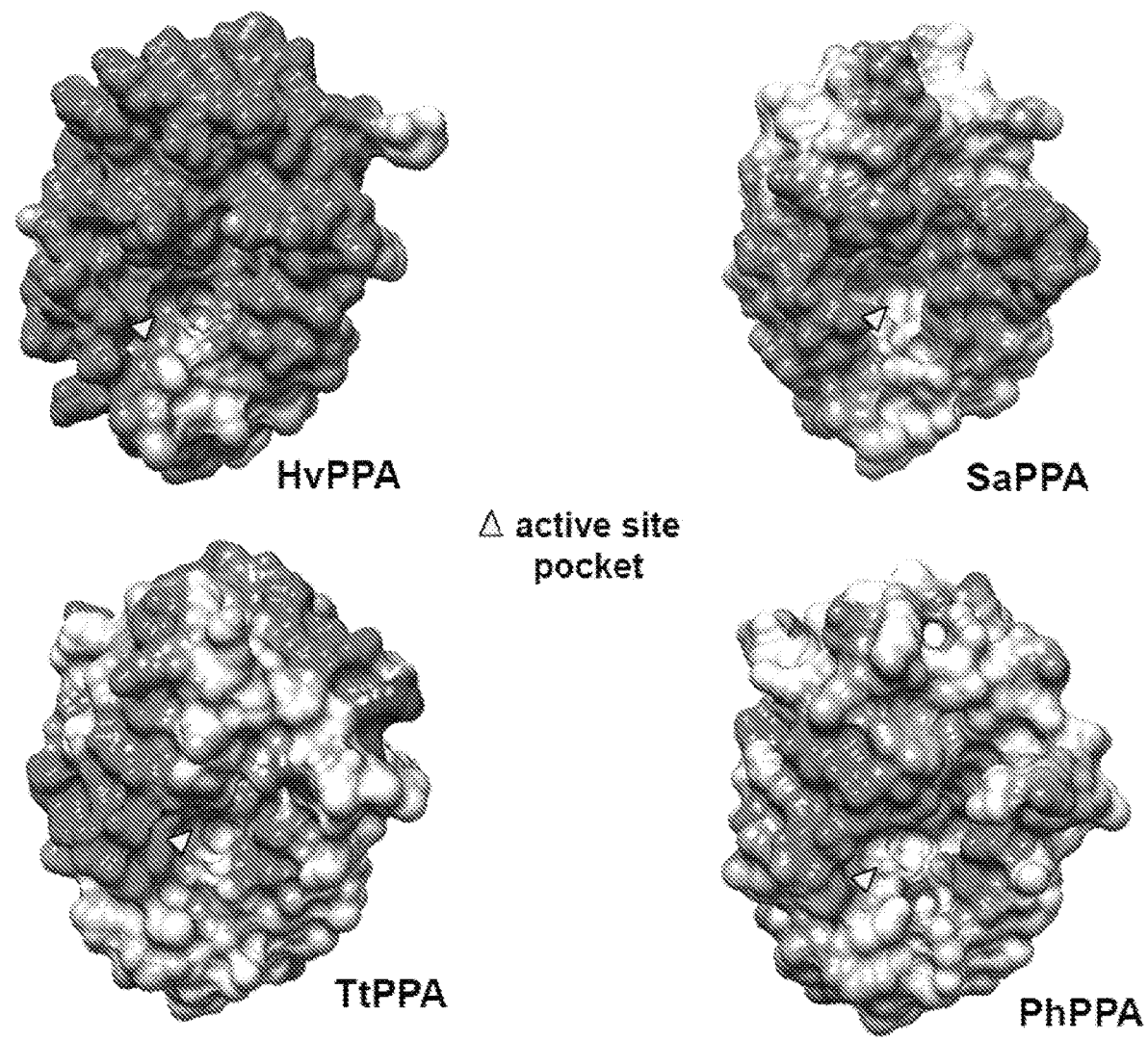

HvPPA was further analyzed by multiple amino acid sequence alignment and Phyre2-based homology modeling. By this analysis, HvPPA was found to have 42-55% identity and 60-71% similarity in amino acid sequence to biochemically characterized archaeal PPAs of the Class A type (IPR008162 family) (FIG. 2A). HvPPA was predicted to have an OB-fold with a central β-barrel structure and α-helices in a $\beta_{1-8}$-$\alpha_1$-$\beta_9$-$\alpha_2$ topology (FIG. 2A) that was analogous to related archaeal PPAs and compatible with their quaternary structure, i.e., dimer of trimers and trimer) (FIG. 2B). The active site residues of *Saccharomyces cerevisiae* ScPPA, including those that bind substrate and product were found conserved in HvPPA (FIG. 2B). In particular, HvPPA D69 was found analogous to ScPPA D117, a key residue in pyrophosphate hydrolysis in which the nucleophile is generated by coordinating a water molecule to two metal ions and further strengthened by donating a hydrogen bond to D117. Interestingly, HvPPA had two cysteine residues (C24 at the C-terminus of the β1 strain and C85 at the N-terminus of the (36 strain) in a Cys-$X_{63}$-Cys motif highly conserved among haloarchaeal PPAs, yet unusual for this group of enzymes (FIG. 2A-B). These conserved cysteine residues were at a significant distance from the predicted active site, with C85 residing notably near the intrasubunit interfaces suggesting redox status could play a role in quaternary structure configuration. HvPPA was also found to have a highly negative surface charge compared to other PPAs that have been characterized (FIG. 2C).

Based on the hierarchical clustering and 3D-structural modeling described above, the HPPAs were found to be phylogentically distinct members of the Class A type (IPR008162 family) with unique features in primary amino acid sequence and 3D-structure. Thus, PPAs of the haloarchaea were provided for identifying new enzymes with novel biochemical properties.

EXAMPLE 2

HvPPA Purified to Homogeneity as a Trimer and Hexamer

Figure 3A:
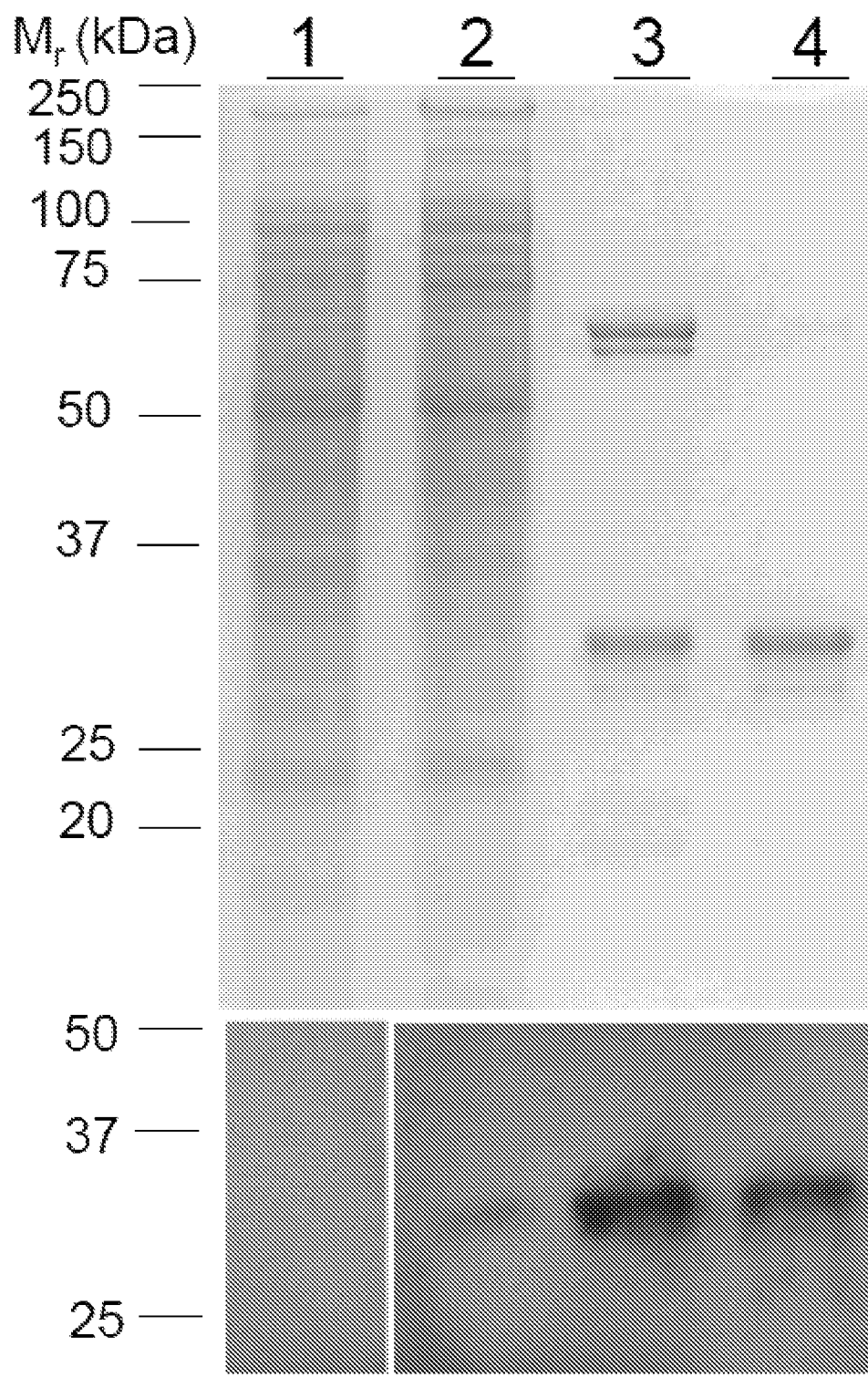
FIGS. 3A-3B. Class A type inorganic pyrophosphatase purified from *Haloferax volcanii* by tandem affinity and size exclusion chromatography. A) HvPPA fractions analyzed by SDS-PAGE. *Hfx. volcanii* H26 (lane 1) and H26-pJAM2920 expressing $His_6$-HvPPA (lane 2) applied at $OD_{600}$ of 0.065 cells per lane. $Ni^{2+}$-Sepharose (lane 3) and Superdex 200 GL10/300 (lane 4) chromatography fractions of HvPPA applied at 1 μg protein per lane. Protein was separated by reducing 10% SDS-PAGE and analyzed by Coomassie Blue R-250 staining (upper) and anti-His6 immunoblotting (lower). B) HvPPA analyzed by Superdex 200 30/100 GL size exclusion chromatography. Column fractions are represented by a semi-log plot of molecular weight (Mr in kDa) verses Kay with molecular mass standards (●) and HvPPA hexamer (□) and trimer (○) indicated.
Figure 3B:
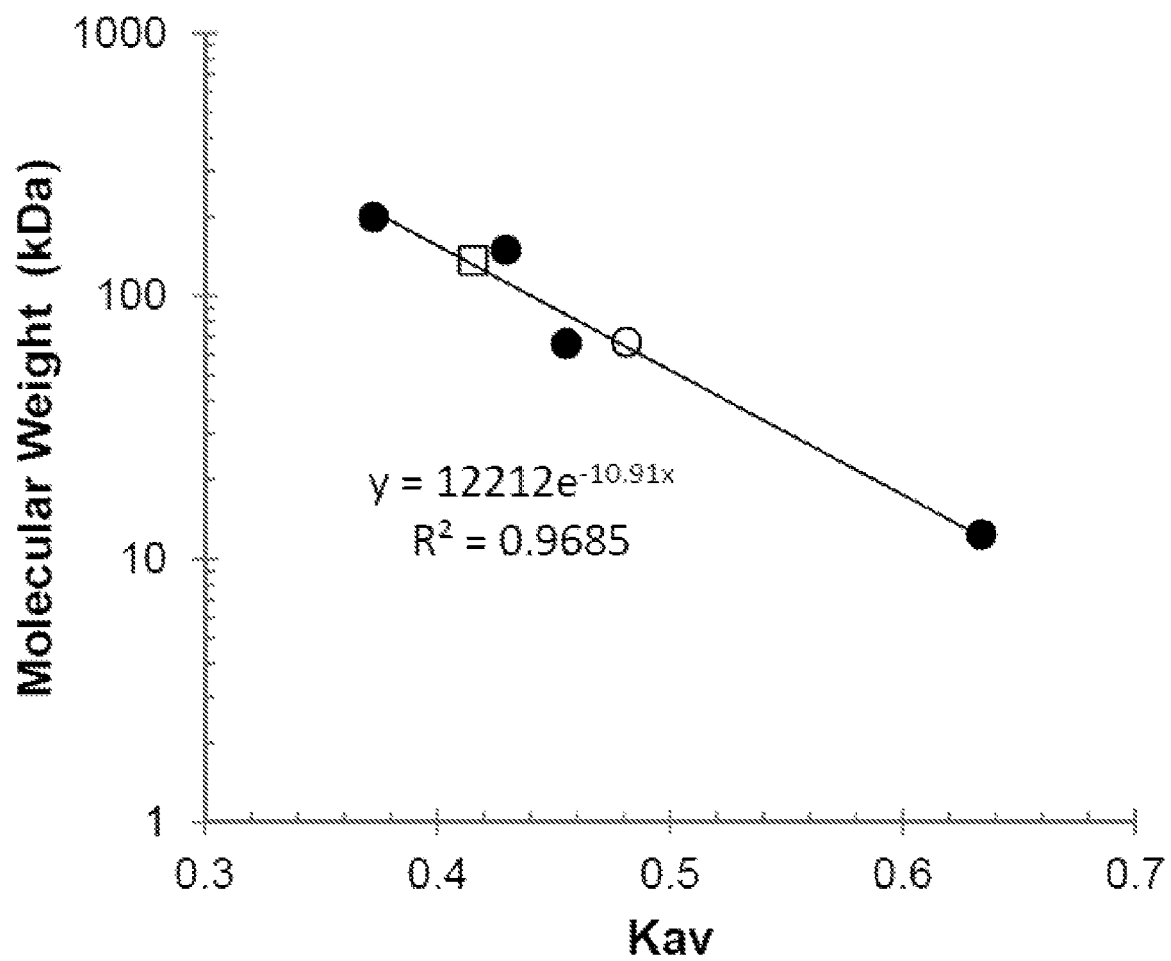

HvPPA was chosen as a representative of the haloarchaeal PPAs for purification and biochemical characterization. To accomplish this, HvPPA was constitutively expressed from an rRNA P2 promoter and purified to homogeneity at high yield from an engineered strain of *Hfx. volcanii* (H26-pJAM2920) that expressed HvPPA with an N-terminal $His_6$-tag in trans. Thus, HvPPA was purified 357-fold by a tandem approach that relied upon $Ni^{2+}$-based immobilized metal ion affinity chromatography (IMAC) and size exclusion chromatography (SEC) (Table 1; FIG. 3A). Based on SEC, HvPPA was purified as two distinct homooligomeric fractions including hexamers of ~134 kDa and trimers of ~64 kDa (FIG. 3B). The HvPPA trimers were only 78% as active as the hexamer and, thus, were not further pursued for biochemical characterization. The hexameric HvPPA consisted of $His_6$-HvPPA as well as minor fraction of genome-encoded HvPPA (FIG. 3A). The gel-based estimations for the wild type and $His_6$-HvPPA of 25.6 and 36.6 kDa that were observed by SDS-PAGE were found to be 5-8 kDa larger than the theoretical $M_r$ of 20.4 and 22.5 kDa, respectively. This finding is explained by the prediction that HvPPA has a pI of 3.98 (with the pI of $His_6$-HvPPA also low at 4.28). This overall negative charge would likely alter the SDS-coating and retard the migration of HvPPA in SDS-PAGE gels, as is commonly observed for proteins with highly acidic regions. The finding that HvPPA associates as a homo-trimer and homo-hexamer is consistent with the configuration of Class A type PPAs of thermophilic and hyperthermophilic archaea (Table 3). Thus, HvPPA is a dimer of trimers as has been observed in x-ray crystal structures of PPAs (e.g., PDB: 1QEZ and 3I98).

TABLE 3

Archaeal inorganic pyrophosphatases (PPAs) [E.C. 3.6.1.1] of the Class A type (IPR008162 family).[1]

| Organism | *Thermoplasma acidophilum* | *Pyrococcus horikoshii* | *Sulfolobus* sp. | *Methanothermobacter thermautotrophicus* | *Thermococcus thioreducens* | *Haloferax volcanii* |
|---|---|---|---|---|---|---|
| Gene locus_tag | Ta0399 | PH1907 | STK_05240 Saci_0955 | MTH_263 (presumed) | H0USY5_9EURY | HVO_0729 |
| Amino acid number (aa) | 179 aa | 178 aa | 172-173 aa | 176 aa | 178 aa | 177 aa |
| pI (theoretical) | 5.33 | 4.97 | 4.83-4.92 (4.8 obs) | 4.69 | 4.76 | 3.98 |
| $M_r$ (theoretical) | 20.5 kDa | 20.8 kDa | 19.4 kDa | 20.1 kDa | 20.9 kDa | 20.4 kDa |
| $M_r$ (observed) | 6 × 22 kDa | 6 × 24.5 kDa | 4-6 × 17-21 kDa | 2-4 × 25 kDa | — | 3-6 × 27 kDa |
| Cation-dependence | $Mg^{2+}$ | $Mg^{2+}$; $Co^{2+}$, $Zn^{2+}$, $Mn^{2+}$ (partial) | $Mg^{2+}$; $Co^{2+}$, $Zn^{2+}$, $Mn^{2+}$ (partial) | $Mg^{2+}$; $Co^{2+}$ (partial) | — | $Mg^{2+}$, $Mn^{2+}$ |
| Inhibitors | $Ca^{2+}$, phenylgloyxal | NaF | NaF, $Ca^{2+}$, phenylgloyxal | NaF | — | NaF |
| Substrate(s) hydrolyzed | PPi | PPi [$P_3$ (2.7%); ATP (5.9%); ADP (2.9%)] | PPi [pNP, PEP (1-2%); ATP, $P_3$, ADP (3-6%); TTP, ITP (10%)] | PPi | — | PPi |
| Km | 7 μM PPi 1.7 mM $Mg^{2+}$ | 14-11 μM PPi 0.3 mM $Mg^{2+}$ | 5 μM PPi 0.9 mM $Mg^{2+}$ | 0.16 mM PPi 4.9 mM $Mg^{2+}$ | — | 0.55 mM PPi (42° C.) 0.26 mM PPi (25° C.) 13.4 mM $Mg^{2+}$(25° C.) |

Table 3-continued

Archaeal inorganic pyrophosphatases (PPAs) [E.C. 3.6.1.1] of the Class A type (IPR008162 family).[1]

| Organism | Thermoplasma acidophilum | Pyrococcus horikoshii | Sulfolobus sp. | Methanothermobacter thermautotrophicus | Thermococcus thioreducens | Haloferax volcanii |
|---|---|---|---|---|---|---|
| Vmax | 1100 U · mg$^{-1}$ (56° C.) | 930 U · mg$^{-1}$ (60° C.) | 860 U · mg$^{-1}$ (75° C.) | 570 U · mg$^{-1}$ | — | 465 U · mg$^{-1}$ (42° C.) 53 U · mg$^{-1}$ (25° C.) |
| kcat | 2200 s$^{-1}$ | 744-3436 s$^{-1}$ | 1700 s$^{-1}$ | — | — | 1050 s$^{-1}$ |
| Hill coefficient(s) | 1.8 (Mg$^{2+}$) | Cooperative binding | 1.9 (Mg$^{2+}$) | 3.3 (PPi), 2.0 (Mg$^{2+}$) | — | 2.1 (PPi, 42° C.) 1.4 (PPi, 25° C.) 2.6 (Mg$^{2+}$, 25° C.) |
| Temp., optimum | 85° C. | 70-88° C. | 75° C. | 70° C. | — | 42° C. |
| pH, optimum | | pH 7.5-10 | pH 6.5-7.0 | pH 7.7 (60° C.) | — | pH 8.5 (25° C.) |
| Thermal inactivation (half-life) | | 50 min (105° C.) | 2.5 h (95° C.) >24 h (75° C.) | — | — | 2 h (65° C.) |
| Soluble, cytoplasmic | Yes | Yes | Yes | Yes | — | Yes |
| Heterologous system | E. coli | E. coli | E. coli | — | E. coli | — |
| Crystal structure (PDB number) | — | 1UDE | 1QEZ | — | 3Q4W, 3I98, 3R5U, 3R5V, 3R6E, 3Q9M | — |
| Example of Coupled assay | DNA polymerase (PCR, sequencing) | DNA polymerase (PCR) | — | — | — | Ub/Ubl adenylation |
| Ref. | [4; 18; 19] | [5; 20; 21; 22] | [23; 24; 25; 26; 27] | [28] | [29], unpublished | This study |

[1]Abbreviations: U/mg is µmol PPi hydrolyzed per min (mg protein)$^{-1}$; —, not reported. HVO_0729 (sp: D4GT97); PH1907 (sp: O59570); MJ0608 (sp: Q58025); Ta0399 (sp: P37981); MTH_263 (sp: O26363); STK_05240 (sp: Q974Y8); Saci_0955 (sp: P50308); H0USY5_9EURY (sp: H0USY5); Sulfolobus sp. (S. acidocaldarius ATCC 33909 and S. tokodaii str. 7); Vmax is highest reported.

EXAMPLE 3

Catalytic Activity of HvPPA

Figure 4A:
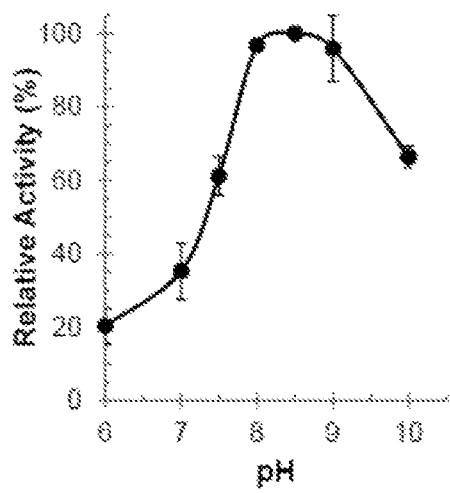
FIGS. 4A-4D. Effect of pH, temperature, salt and divalent cations on *Haloferax volcanii* inorganic phyrophosphatase (HvPPA) activity. A-C) HvPPA was equilibrated for 10 min at the pH, temperature, and NaCl concentrations indicated prior to the addition of PPi substrate (100 μM). $MgCl_2$ (10 mM) was included in the activity assays. For pH optimum, assays were supplemented with 3 M NaCl and included 20 mM buffers of sodium acetate at pH 4-5, MES at pH 6-6.5, Tris-Cl at pH 7-9 and CAPS at pH 10. For temperature optimum assays, reactions were in 20 mM Tris-Cl pH 8 supplemented with 3 M NaCl. For salt optimum, HvPPA was diluted from 20 mM Tris-Cl pH 8 containing 3 m NaCl into the same buffer with NaCl concentrations as indicated. D) To test the influence of cations, HvPPA was dialyzed sequentially against 500 ml of buffer (20 mM Tris-Cl pH 8, 2 M NaCl and 1 μM EDTA) (4 h at 4° C.) and the same buffer with EDTA omitted (4 h at 4° C.). Reactions for panel D contained HvPPA (0.93 μg), 20 mM Tris-Cl pH 8, 2 M NaCl and divalent metal at the concentration indicated. Metals used were: $CaCl_2 \cdot 2H_2O$, $ZnCl_2$, $CoCl_2 \cdot 6H_2O$, $MnCl_2 \cdot 4H_2O$, $NiCl_2 \cdot 6H_2O$ and $MgCl_2 \cdot 6H_2O$. Reactions were monitored for 10 min at RT unless otherwise indicated.
Figure 4B:
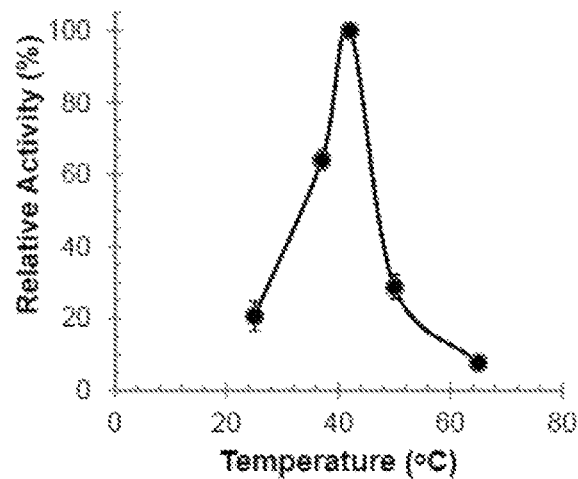
Figure 4C:
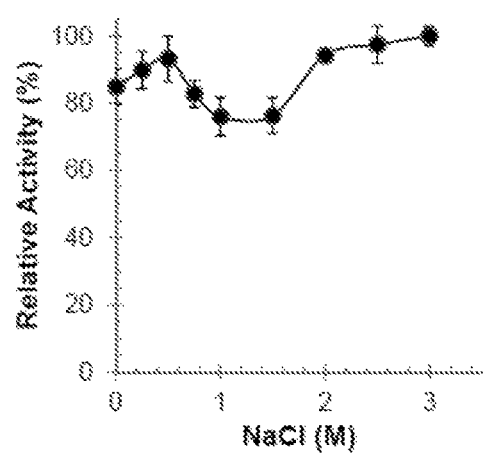
Figure 4D:
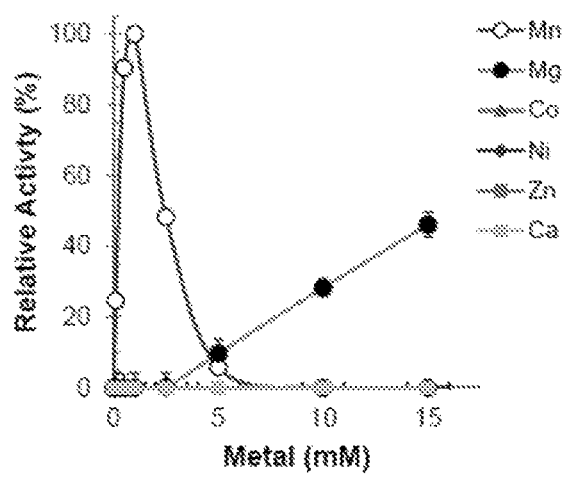

HvPPA hexamers readily hydrolyzed PPi to orthophosphate with optimal activity detected at 42° C. and basic pH (pH 8-9) (FIGS. 4A-B). Supplementation of reactions with NaCl (within a 120-fold range of 0.025 to 3 M NaCl) had little, if any, effect on the relative activity of HvPPA (FIG. 4C). HvPPA was inactivated when divalent cations were removed from the reaction by dialysis against the metal chelator EDTA. The PPi hydrolyzing activity of the EDTA-treated HvPPA could be partially restored by supplementation of the enzyme with Mn$^{2+}$ or Mg$^{2+}$ ions, but not by addition of Zn$^{2+}$, Ca$^{2+}$, Co$^{2+}$ or Ni$^{2+}$ (FIG. 4D) (with the restored enzyme at only half the activity of the untreated control when similarly assayed at 2.5 mM MgCl$_2$). HvPPA was found to be significantly stimulated by addition of Mg$^{2+}$ to the reaction buffer with optimal PPi hydrolyzing activity at 20-40 mM Mg$^{2+}$ (FIG. 4E). Addition of other divalent cations such as Mn$^{2+}$ did not stimulate the activity of HvPPA, when it was not treated with EDTA. Thus, HvPPA is most likely coordinated to Mg$^{2+}$ (and not Mn$^{2+}$) ions upon purification from Hfx. volcanii and requires relatively high concentrations of Mg$^{2+}$ for full activity. Intracellular Mg$^{2+}$ ions are quite high in the haloarchaea with the intracellular concentration of Mg$^{2+}$ reported at 120 mM for Halobacterium salinarum.

Figure 5A:
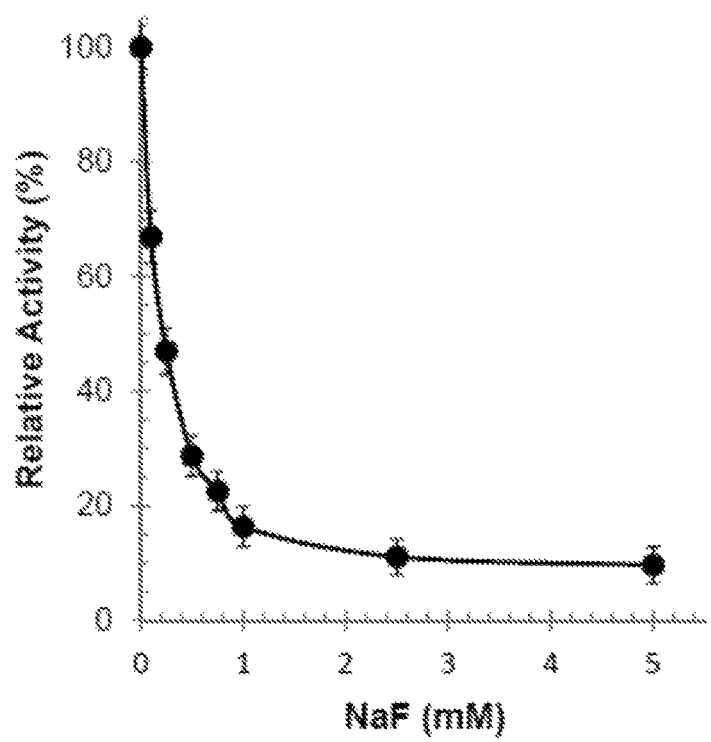
FIGS. 5A-5B. Sodium fluoride-based inhibition of *Haloferax volcanii* inorganic phyrophosphatase (HvPPA). A) HvPPA (1.3 μg) was assayed in 1 ml reaction volume containing 1 mM PPi, 10 mM $MgCl_2$, 3 M NaCl and 20 mM Tris-Cl buffer pH 7.5 supplemented with NaF as indicated. Reactions were monitored for 15 min at RT. B) Amino acid residues of HvPPA predicted to interact with $F^-$, PPi, $H_2O$ and $Mg^{2-}$ bound molecules as determined by modeling compared to the x-ray crystal structure of *E. coli* PPA (PDB: 2AUU).
Figure 5B:
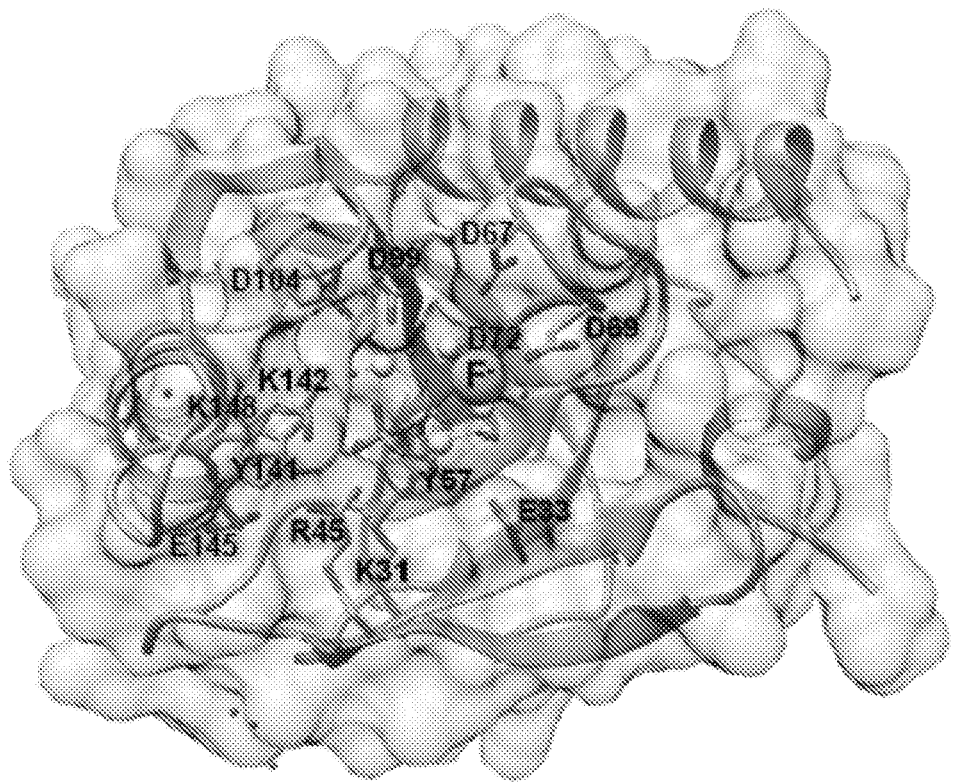

Similar to the other Class A type PPAs, HvPPA was inhibited by sodium fluoride (NaF) with K$_i$ values of 1.8 mM NaF at pH 8.5 and 0.2 mM NaF at pH 7.5 (FIG. 5A). Increased sensitivity to fluoride inhibition at more neutral pH is commonly observed for Class A type PPAs and other enzymes including catalases and peroxidases. Consistent with the NaF inhibition of HvPPA, amino acid residues interacting with the F$^-$, PPi, H$_2$O and Mg$^{2+}$ bound molecules in the X-ray crystal structure of E. coli PPA (PDB: 2AUU) are conserved in the haloarchaeal enzyme (FIG. 5B). F$^-$ ions inhibit the activity of Class A type PPAs by substituting the attacking nucleophile in the PPi hydrolysis reaction.

HvPPA displayed non-Michaelis-Menten kinetics for PPi hydrolysis. When assayed at 42° C., HvPPA has the V$_{max}$ of 465 U/mg and K$_m$ of 0.55 mM for the PPi substrate. In contrast, HvPPA had the reduced V$_{max}$ of 53 U/mg and K$_{max}$ of 0.26 mM for PPi at 25° C. Sigmoidal kinetic profiles indicative of positive cooperative binding were detected for Mg$^{2+}$ with the degree of cooperativity represented by a Hill coefficient of 2.62 at 25° C. (a K$_m$ of 13 mM was also determined for Mg$^{2+}$ at these conditions). HvPPA did not hydrolyze detectable levels of nucleoside triphosphate (ATP, TTP, GTP or CTP) or nucleoside diphosphate (ADP) hydrolysis, a property useful for coupling PPAs with nucleotide-dependent enzymes in assays. Based on these results, HvPPA catalyzes the hydrolysis of PPi with kinetic properties that are most closely related to M. thermautotrophicus PPA among the HPPAs of thermophilic and hyperthermophilic archaea (Table 3). The low affinity of HvPPA for Mg$^{2+}$ and PPi based on K$_m$ values is consistent with the unusually high levels of these types of ions within the cytosol of haloarchaea.

EXAMPLE 4

HvPPA Tolerance to High Temperature and Organic Solvents

Figure 6A:
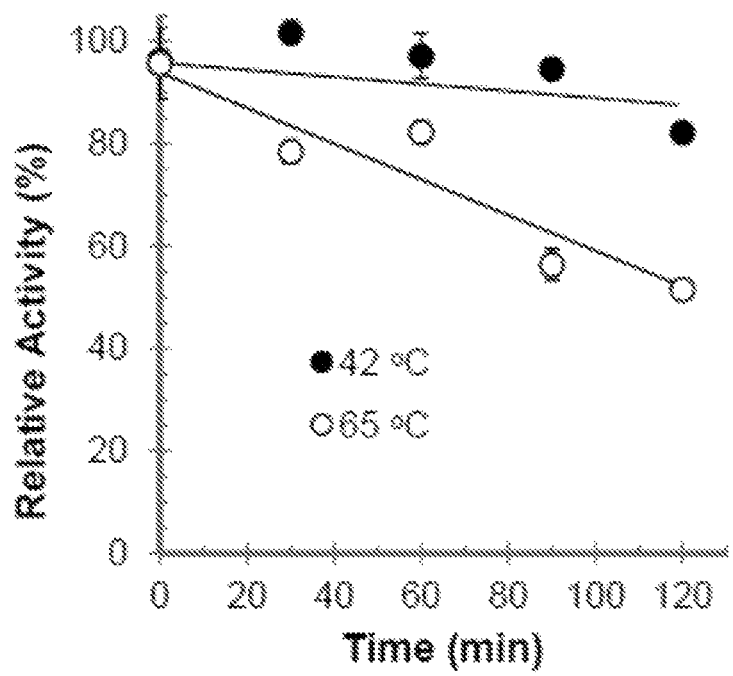
FIGS. 6A-6D. Effect of salt, solvent and temperature on *Haloferax volcanii* inorganic phyrophosphatase (HvPPA). A) HvPPA thermostability. HvPPA was incubated at 42° C. and 65° C. as indicated with enzyme at 0.093 mg/ml of buffer (20 mM Tris-Cl pH 8, 2.5 mM $MgCl_2$ and 3 M NaCl). HvPPA was diluted to 0.28 μg per 100 μl buffer (with $MgCl_2$ increased to 10 mM) and assayed by addition of 1 mM PPi substrate (10 min, RT). Activity is % relative to samples incubated on ice. B) HvPPA stability in 50% (v/v) solvent. HvPPA was incubated for 2 h (on ice) at 0.47 mg/ml buffer (20 mM Tris-Cl pH 8 and 2 M NaCl) supplemented with solvent as indicated. HvPPA was diluted to 2.4 μg per 100 μl buffer (20 mM Tris-Cl pH 8, 2.5 mM $MgCl_2$ and 2 M NaCl) and assayed by addition of 50 μM PPi substrate (10 min, RT). Activity is % relative to samples incubated with no solvent. C) HvPPA activity in 25% (v/v) solvent. Reactions were 500 μl with 2.8 μg HvPPA, 1.5 M NaCl, 1.5 mM PPi, 10 mM $MgCl_2$. Reaction occurred at 10 minutes at RT. D) HvPPA stability in salt. HvPPA was incubated for 2 h (on ice) at 0.3 mg per ml of buffer (20 mM Tris-Cl pH 8) supplemented with NaCl at the concentrations indicated. HvPPA was diluted to 0.87 μg per 100 μl reaction buffer as in FIG. 6B. Activity is % relative to samples incubated in buffer supplemented with 3M NaCl.
Figure 6B:
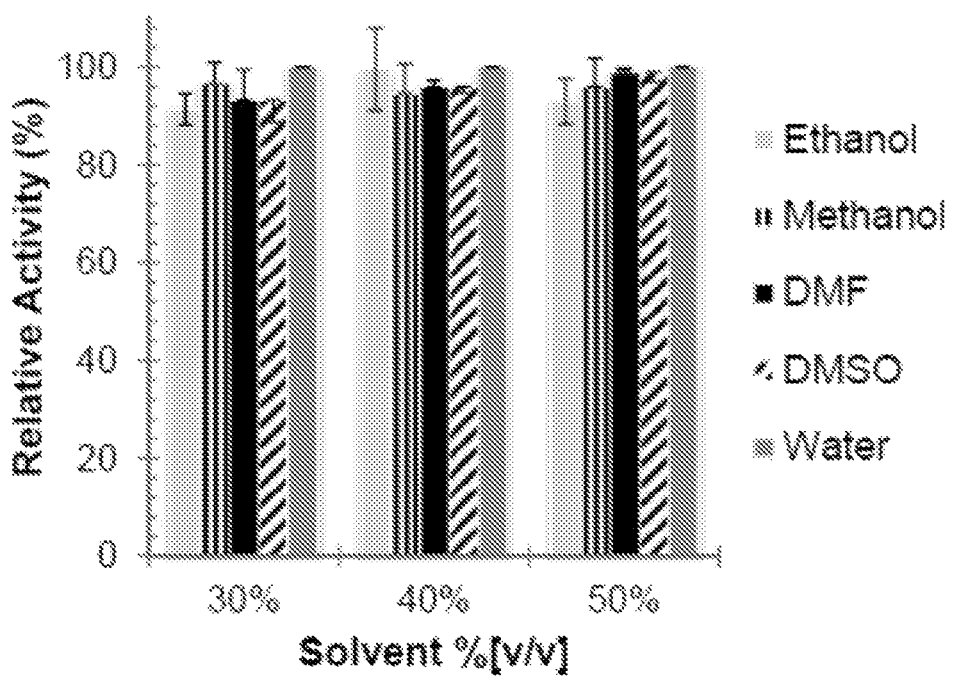
Figure 6C:
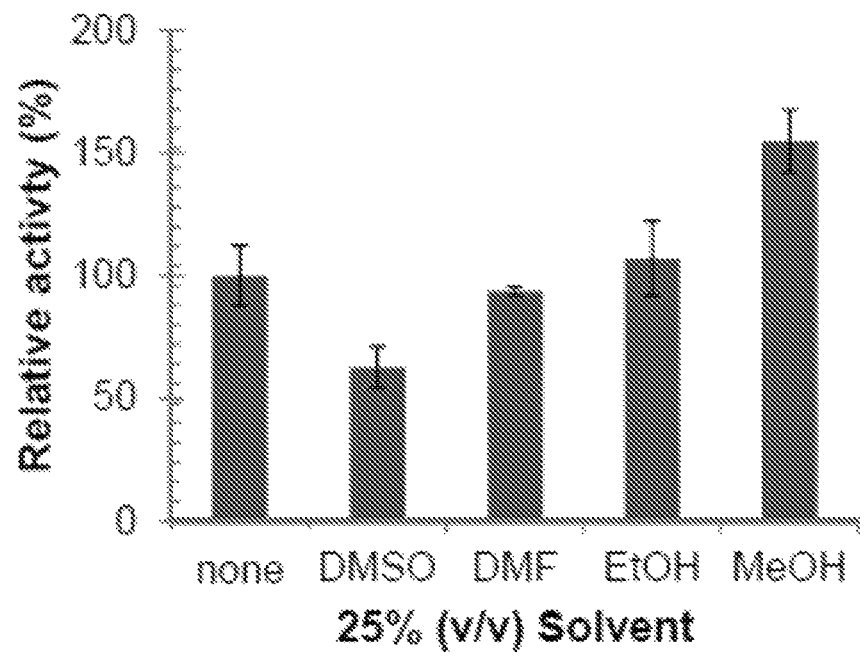
Figure 6D:
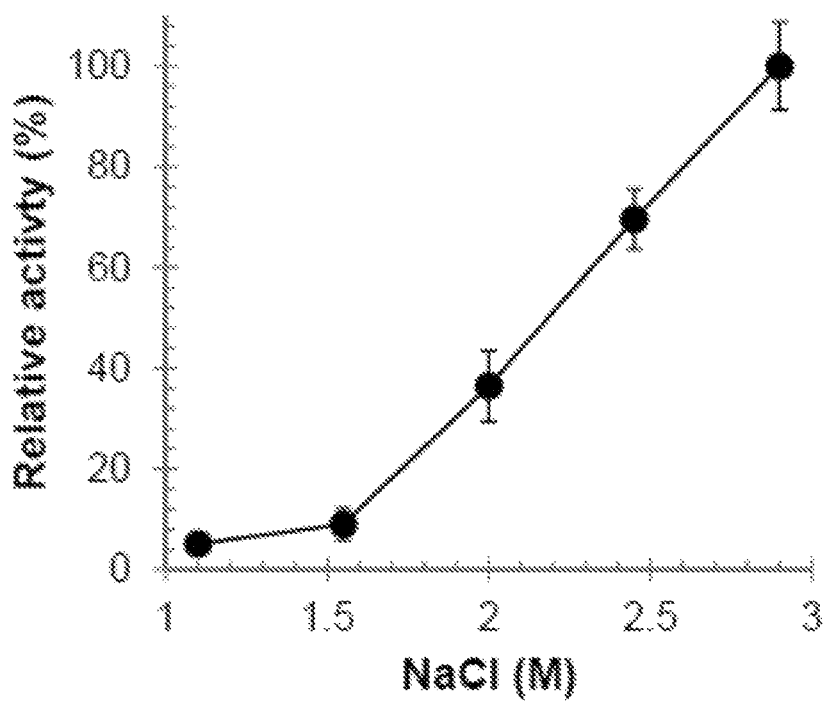

HvPPA is thermostable with a thermal inactivation half-life of 2 h at 65° C.; 82% activity remained after 2 h at 42° C. (FIG. 6A). HvPPA is not only thermostable but also stable in organic solvent with little if any inactivation of enzyme after 2 h incubation in buffer supplemented with 50% [v/v] DMSO, DMF, ethanol or methanol (FIG. 6B). HvPPA-mediated hydrolysis of PPi was also found to be robust in organic solvents, with the enzyme displaying 110-150% activity in buffers supplemented with 25% (v/v) methanol or ethanol and 63-94% activity in buffers with 25% (v/v) DMSO or DMF, compared to no solvent controls (FIG. 6C). HvPPA is more stable when stored in buffers supplemented with 2-3 M NaCl compared to 1.5 M NaCl or less (FIG. 6D). However, the enzyme was fully active over a wide range of salts (as noted earlier in FIG. 4C).

EXAMPLE 5

HvPPA for Detection of PPI By-Product in Coupled Assay at Low Water Activity

PPAs are not yet available for use in conditions of high salt or organic solvent to drive the activity of enzymes that generate PPi as a by-product. The use of HvPPA with a PPi-generating enzyme that functions in low water activity (high salt) by coupled assay is provided. In particular, HvPPA was used to monitor the PPi by-product of the 'salt loving' enzyme UbaA of *Hfx. volcanii* at 42° C. in a buffer system with 2 M NaCl. UbaA has a NAD/FAD-binding fold domain common to ubiquitin activating E1 family enzymes and is required for the formation of ubiquitin-like bonds in archaea. UbaA is presumed to adenylate the C-terminal α-carboxylate group of ubiquitin-like proteins (named SAMPs in archaea) and release PPi as a by-product (FIG. 7A). To monitor this activity, HvPPA was used in a coupled assay to drive UbaA-mediated adenylation of SAMP1 and hydrolyze the PPi by-product to 2 Pi for detection by colorimetric assay. Significant levels of Pi were detected when UbaA and HvPPA were coupled with ATP and SAMP1 in the reaction (FIG. 7B). Pi was not detected when ATP, UbaA, HvPPA or SAMP1 were omitted from the adenylation assay (FIG. 7B). Deletion of the C-terminal diglycine residues of SAMP1 (ΔGG) were found to significantly reduce the level of Pi detected by this assay. Likewise, the reaction was found highly specific for ATP, with little if any Pi generated enzymatically when ATP was replaced by other nucleotides (AMP, ADP, AMP-PNP, CTP, GTP, TTP and UTP) (FIG. 7B). Based on these results, HvPPA is useful for hydrolysis of PPi in coupled assays that require conditions of low water activity, moderately high temperatures and HvPPA can withstand high temperature pretreatments.

EXAMPLE 6

HvPPA is Evolutionarily, Structurally and Biochemically Distinct

PPAs are inactivated in dose dependent manner by organic solvents. In contrast, HvPPA provided in the instant invention displays thermostable and solvent tolerant properties and catalytic activities. HvPPA is useful for coupled assay with enzymes that generate PPi as a by-product and can perform this activity in conditions of high temperature and low water activity. In contrast, HvPPA opens new possibilities for the hydrolysis of PPi and related compounds in high salt and organic solvent systems to increase the solubility of hydrophobic substrates (such as lipids, phospholipids and fatty acids), and allows for novel synthetic chemistry, altering substrate specificity, easy of product recovery, and reducing microbial contamination.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

[1] R. Lahti, Microbial inorganic pyrophosphatases. Microbiol Rev 47 (1983) 169-78.
[2] D. L. Nelson, A. L. Lehninger, and M. M. Cox, Lehninger principles of biochemistry, W.H. Freeman, New York, 2013.
[3] S. Tabor, and C. C. Richardson, DNA sequence analysis with a modified bacteriophage T7 DNA polymerase. Effect of pyrophosphorolysis and metal ions. J Biol Chem 265 (1990) 8322-8.
[4] P. B. Vander Horn, M. C. Davis, J. J. Cunniff, C. Ruan, B. F. McArdle, S. B. Samols, J. Szasz, G. Hu, K. M. Hujer, S. T. Domke, S. R. Brummet, R. B. Moffett, and C. W. Fuller, Thermo Sequenase DNA polymerase and *T. acidophilum* pyrophosphatase: new thermostable enzymes for DNA sequencing. Biotechniques 22 (1997) 758-62, 764-5.
[5] S. Y. Park, B. Lee, K. S. Park, Y. Chong, M. Y. Yoon, S. J. Jeon, and D. E. Kim, Facilitation of polymerase chain reaction with thermostable inorganic pyrophosphatase from hyperthermophilic archaeon *Pyrococcus horikoshii*. Appl Microbiol Biotechnol 85 (2010) 807-12.
[6] M. Xiao, A. Phong, K. L. Lum, R. A. Greene, P. R. Buzby, and P. Y. Kwok, Role of excess inorganic pyrophosphate in primer-extension genotyping assays. Genome Res 14 (2004) 1749-55.
[7] P. R. Cunningham, and J. Ofengand, Use of inorganic pyrophosphatase to improve the yield of in vitro transcription reactions catalyzed by T7 RNA polymerase. Biotechniques 9 (1990) 713-4.
[8] B. J. Mengeling, and S. J. Turco, A high-yield, enzymatic synthesis of GDP-D-[3H]arabinose and GDP-L-[3H]fucose. Anal Biochem 267 (1999) 227-33.
[9] L. Li, Y. Liu, Y. Wan, Y. Li, X. Chen, W. Zhao, and P. G. Wang, Efficient enzymatic synthesis of guanosine 5'-diphosphate-sugars and derivatives. Org Lett 15 (2013) 5528-30.
[10] G. H. Zhou, H. Shirakura, M. Kamahori, K. Okano, K. Nagai, and H. Kambara, A gel-free SNP genotyping method: bioluminometric assay coupled with modified primer extension reactions (BAMPER) directly from double-stranded PCR products. Hum Mutat 24 (2004) 155-63.
[11] G. Zhou, M. Kamahori, K. Okano, G. Chuan, K. Harada, and H. Kambara, Quantitative detection of single nucleotide polymorphisms for a pooled sample by a bioluminometric assay coupled with modified primer extension reactions (BAMPER). Nucleic Acids Res 29 (2001) E93.
[12] C. Ha, and P. Y. Kwok, The template-directed dye-incorporation assay with fluorescence polarization detection (FP-TDI). CSH Protoc 2007 (2007) pdb.prot4844.
[13] H. T. Nguyen, Y. Chong, D. K. Oh, Y. S. Heo, P. T. Viet, L. W. Kang, S. J. Jeon, and D. E. Kim, An efficient colorimetric assay for RNA synthesis by viral RNA-dependent RNA polymerases, using thermostable pyrophosphatase. Anal Biochem 434 (2013) 284-6.

[14] I. Cestari, and K. Stuart, A spectrophotometric assay for quantitative measurement of aminoacyl-tRNA synthetase activity. J Biomol Screen 18 (2013) 490-7.

[15] C. S. Francklyn, E. A. First, J. J. Perona, and Y. M. Hou, Methods for kinetic and thermodynamic analysis of aminoacyl-tRNA synthetases. Methods 44 (2008) 100-18.

[16] T. P. Geladopoulos, T. G. Sotiroudis, and A. E. Evangelopoulos, A malachite green colorimetric assay for protein phosphatase activity. Anal Biochem 192 (1991) 112-6.

[17] K. Itaya, and M. Ui, A new micromethod for the colorimetric determination of inorganic phosphate. Clin Chim Acta 14 (1966) 361-6.

[18] O. M. Richter, and G. Schäfer, Purification and enzymic characterization of the cytoplasmic pyrophosphatase from the thermoacidophilic archaebacterium *Thermoplasma acidophilum*. Eur J Biochem 209 (1992) 343-9.

[19] O. M. Richter, and G. Schäfer, Cloning and sequencing of the gene for the cytoplasmic inorganic pyrophosphatase from the thermoacidophilic archaebacterium *Thermoplasma acidophilum*. Eur J Biochem 209 (1992) 351-5.

[20] S. J. Jeon, and K. Ishikawa, Characterization of the Family I inorganic pyrophosphatase from *Pyrococcus horikoshii* OT3. Archaea 1 (2005) 385-9.

[21] B. Liu, M. Bartlam, R. Gao, W. Zhou, H. Pang, Y. Liu, Y. Feng, and Z. Rao, Crystal structure of the hyperthermophilic inorganic pyrophosphatase from the archaeon *Pyrococcus horikoshii*. Biophys J 86 (2004) 420-7.

[22] D. Lu, G. Xie, and R. Gao, Cloning, purification, and characterization of inorganic pyrophosphatase from the hyperthermophilic archaea *Pyrococcus horikoshii*. Protein Expr Purif 99 (2014) 94-8.

[23] T. Wakagi, C. H. Lee, and T. Oshima, An extremely stable inorganic pyrophosphatase purified from the cytosol of a thermoacidophilic archaebacterium, *Sulfolobus acidocaldarius* strain 7. Biochim Biophys Acta 1120 (1992) 289-96.

[24] W. Meyer, R. Moll, T. Kath, and G. Schäfer, Purification, cloning, and sequencing of archaebacterial pyrophosphatase from the extreme thermoacidophile *Sulfolobus acidocaldarius*. Arch Biochem Biophys 319 (1995) 149-56.

[25] V. M. Leppänen, H. Nummelin, T. Hansen, R. Lahti, G. Schäfer, and A. Goldman, *Sulfolobus acidocaldarius* inorganic pyrophosphatase: structure, thermostability, and effect of metal ion in an archael pyrophosphatase. Protein Sci 8 (1999) 1218-31.

[26] T. Hansen, C. Urbanke, V. M. Leppänen, A. Goldman, K. Brandenburg, and G. Schäfer, The extreme thermostable pyrophosphatase from *Sulfolobus acidocaldarius*: enzymatic and comparative biophysical characterization. Arch Biochem Biophys 363 (1999) 135-47.

[27] T. Wakagi, T. Oshima, H. Imamura, and H. Matsuzawa, Cloning of the gene for inorganic pyrophosphatase from a thermoacidophilic archaeon, *Sulfolobus* sp. strain 7, and overproduction of the enzyme by coexpression of tRNA for arginine rare codon. Biosci Biotechnol Biochem 62 (1998) 2408-14.

[28] G. J. van Alebeek, J. T. Keltjens, and C. van der Drift, Purification and characterization of inorganic pyrophosphatase from *Methanobacterium thermoautotrophicum* (strain delta H). Biochim Biophys Acta 1206 (1994) 231-9.

[29] R. C. Hughes, L. Coates, M. P. Blakeley, S. J. Tomanicek, P. Langan, A. Y. Kovalevsky, J. M. García-Ruiz, and J. D. Ng, Inorganic pyrophosphatase crystals from *Thermococcus thioreducens* for X-ray and neutron diffraction. Acta Crystallogr Sect F Struct Biol Cryst Commun 68 (2012) 1482-7.

[30] P. Arriagada-Strodthoff, S. Karboune, R. J. Neufeld, and S. Kermasha, Optimization of chlorophyllase-catalyzed hydrolysis of chlorophyll in monophasic organic solvent media. Appl Biochem Biotechnol 142 (2007) 263-75.

[31] A. M. Blinkovsky, B. D. Martin, and J. S. Dordick, Enzymology in monophasic organic media. Curr Opin Biotechnol 3 (1992) 124-9.

[32] J. S. Dordick, Non-aqueous enzymology. Curr Opin Biotechnol 2 (1991) 401-7.

[33] Y. L. Khmelnitsky, and J. O. Rich, Biocatalysis in nonaqueous solvents. Curr Opin Chem Biol 3 (1999) 47-53.

[34] R. Grazinoli-Garrido, and M. Sola-Penna, Inactivation of yeast inorganic pyrophosphatase by organic solvents. An Acad Bras Cienc 76 (2004) 699-705.

[35] D. H. Lopes, J. R. Meyer-Fernandes, and M. Sola-Penna, Effects of trehalose and ethanol on yeast cytosolic pyrophosphatase. Z Naturforsch C 54 (1999) 186-90.

[36] D. H. Lopes, and M. Sola-Penna, Urea increases tolerance of yeast inorganic pyrophosphatase activity to ethanol: the other side of urea interaction with proteins. Arch Biochem Biophys 394 (2001) 61-6.

[37] M. Dyall-Smith, The Halohandbook: Protocols for Halobacterial Genetics, Version 7.2, March 2009.

[38] G. Zhou, D. Kowalczyk, M. Humbard, S. Rohatgi, and J. Maupin-Furlow, Proteasomal components required for cell growth and stress responses in the haloarchaeon *Haloferax volcanii*. J Bacteriol 190 (2008) 8096-8105.

[39] M. M. Bradford, A rapid and sensitive method for the quantitation of microgram quantities of protein utilizing the principle of protein-dye binding. Anal Biochem 72 (1976) 248-54.

[40] U. K. Laemmli, Cleavage of structural proteins during the assembly of the head of bacteriophage T4. Nature 227 (1970) 680-5.

[41] K. Tamura, G. Stecher, D. Peterson, A. Filipski, and S. Kumar, MEGA6: Molecular Evolutionary Genetics Analysis version 6.0. Mol Biol Evol 30 (2013) 2725-9.

[42] N. Saitou, and M. Nei, The neighbor-joining method: a new method for reconstructing phylogenetic trees. Mol Biol Evol 4 (1987) 406-25.

[43] M. Nei, and S. Kumar, Molecular Evolution and Phylogenetics, Oxford University Press, New York, 2000.

[44] P. Heikinheimo, V. Tuominen, A. K. Ahonen, A. Teplyakov, B. S. Cooperman, A. A. Baykov, R. Lahti, and A. Goldman, Toward a quantum-mechanical description of metal-assisted phosphoryl transfer in pyrophosphatase. Proc Natl Acad Sci USA 98 (2001) 3121-6.

[45] E. Oksanen, A. K. Ahonen, H. Tuominen, V. Tuominen, R. Lahti, A. Goldman, and P. Heikinheimo, A complete structural description of the catalytic cycle of yeast pyrophosphatase. Biochemistry 46 (2007) 1228-39.

[46] S. C. Peck, Analysis of protein phosphorylation: methods and strategies for studying kinases and substrates. Plant J 45 (2006) 512-22.

[47] C. J. Reed, H. Lewis, E. Trejo, V. Winston, and C. Evilia, Protein adaptations in archaeal extremophiles. Archaea 2013 (2013) 373275.

[48] V. R. Samygina, V. M. Moiseev, E. V. Rodina, N. N. Vorobyeva, A. N. Popov, S. A. Kurilova, T. I. Nazarova, S. M. Avaeva, and H. D. Bartunik, Reversible inhibition of *Escherichia coli* inorganic pyrophosphatase by fluoride: trapped catalytic intermediates in cryo-crystallographic studies. J Mol Biol 366 (2007) 1305-17.

[49] E. A. Thibodeau, and T. F. Keefe, pH-dependent fluoride inhibition of catalase activity. Oral Microbiol Immunol 5 (1990) 328-31.

[50] E. A. Thibodeau, W. H. Bowen, and R. E. Marquis, pH-dependent fluoride inhibition of peroxidase activity. J Dent Res 64 (1985) 1211-3.

[51] A. Oren, Intracellular salt concentrations and ion metabolism in halophilic microorganisms, Halophilic Microorganisms and their Environments, Kluwer Academic Publishers, The Netherlands, 2002, pp. 207-231.

[52] A. T. Matheson, G. D. Sprott, I. J. McDonald, and H. Tessier, Some properties of an unidentified halophile: growth characteristics, internal salt concentration, and morphology. Can J Microbiol 22 (1976) 780-6.

[53] N. Munawar, and P. C. Engel, Prospects for robust biocatalysis: engineering of novel specificity in a halophilic amino acid dehydrogenase. Extremophiles 17 (2013) 43-51.

[54] X. Li, and H. Y. Yu, Characterization of an organic solvent-tolerant lipase from *Haloarcula* sp. G41 and its application for biodiesel production. Folia Microbiol (Praha) 59 (2014) 455-63.

[55] S. Uthandi, B. Saad, M. Humbard, and J. Maupin-Furlow, LccA, an archaeal laccase secreted as a highly stable glycoprotein into the extracellular medium by *Haloferax volcanii*. Appl Environ Microbiol 76 (2010) 733-743.

[56] R. De Castro, D. Ruiz, M. Gimenez, M. Silveyra, R. Paggi, and J. Maupin-Furlow, Gene cloning and heterologous synthesis of a haloalkaliphilic extracellular protease of *Natrialba magadii* (Nep). Extremophiles 12 (2008) 677-687.

[57] H. Wilson, H. Aldrich, and J. Maupin-Furlow, Halophilic 20S proteasomes of the archaeon *Haloferax volcanii*: Purification, characterization, and gene sequence analysis. J. Bacteriol. 181 (1999) 5814-5824.

[58] L. Prunetti, C. J. Reuter, N. L. Hepowit, Y. Wu, L. Barrueto, H. V. Miranda, K. Kelly, and J. A. Maupin-Furlow, Structural and biochemical properties of an extreme 'salt-loving' proteasome activating nucleotidase from the archaeon *Haloferax volcanii*. Extremophiles 18 (2014) 283-93.

[59] H. Miranda, N. Nembhard, D. Su, N. Hepowit, D. Krause, J. Pritz, C. Phillips, D. Söll, and J. Maupin-Furlow, E1- and ubiquitin-like proteins provide a direct link between protein conjugation and sulfur transfer in archaea. Proc Natl Acad Sci USA 108 (2011) 4417-22.

[60] D. Wendoloski, C. Ferrer, and M. L. Dyall-Smith, A new simvastatin (mevinolin)-resistance marker from *Haloarcula hispanica* and a new *Haloferax volcanii* strain cured of plasmid pHV2. Microbiology 147 (2001) 959-64.

[61] T. Allers, H. P. Ngo, M. Mevarech, and R. G. Lloyd, Development of additional selectable markers for the halophilic archaeon *Haloferax volcanii* based on the leuB and trpA genes. Appl Environ Microbiol 70 (2004) 943-53.

We claim:

1. A method comprising:
   conducting a first reaction to produce inorganic pyrophosphates (PPi) in a reaction mixture comprising: 10% to 50% v/v of one or more of dimethyl sulfoxide (DMSO), dimethylformamide (DMF), methanol or ethanol; and
   adding an inorganic pyrophosphatase from a microorganism belonging to family Halobacteriaceae (HPPA) comprising SEQ ID NO:2, or an amino acid sequence having at least 95% sequence identity to SEQ ID NO:2, to the reaction mixture to catalyze hydrolysis of PPi to form inorganic phosphates (Pi),
   wherein the HPPA catalyzes the hydrolysis of PPi and removal of PPi from the reaction mixture and drives the first reaction in a direction toward PPi production.

2. The method of claim 1, wherein the first reaction is an enzymatic reaction.

3. The method of claim 2, wherein the enzymatic reaction is performed under high temperature from about 50° C. to about 100° C.

4. The method of claim 2, wherein the enzymatic reaction is performed under low water activity, wherein low water activity comprises high salt concentration.

5. The method of claim 2, wherein the enzymatic reaction is performed under moderately high temperature from about 40° C. to about 50° C.

6. The method of claim 4, wherein the high salt concentration comprises the concentration of about 1M to about 5M.

7. The method of claim 3, wherein the HPPA is thermostable at high temperature of about 50° C. to about 100° C.

8. A composition comprising a reaction mixture that removes inorganic pyrophosphates (PPi) from a prior reaction and produces inorganic phosphates (Pi), the reaction mixture comprising (1) an inorganic pyrophosphatase from a microorganism belonging to family Halobacteriaceae (HPPA) of SEQ ID NO: 2 or an amino acid sequence having at least 95% sequence identity to SEQ ID NO: 2, and (2) 10 to 50% v/v of one or more of DMSO, DMF, methanol or ethanol, wherein the inorganic pyrophosphatase catalyzes the hydrolysis of PPi to Pi.

* * * * *

SEQUENCE LISTING

```
<160> NUMBER OF SEQ ID NOS: 111

<210> SEQ ID NO 1
<211> LENGTH: 534
<212> TYPE: DNA
<213> ORGANISM: Haloferax volcanii

<400> SEQUENCE: 1
atggtgaacc tctgggaaga tatggagacc ggcccgaacg cgccggacga aatctacgca      60
gtcgtcgagt gcctcaaagg cgagcgcaac aagtacgagt acgacaagga catccccggc     120
gtcgtcctcg accgcgtgct ccactccaac gtccactacc cgtcggacta cggcttcatc     180
ccgcagacgt actacgacga cgaggacccc ttcgacgtgc tcgtcctcgt cgaggaccag     240
acgttccccg gctgcgtcat cgaggcgcgc ccggtcgcgc tcatgaagat ggacgacgac     300
ggcgagcagg acgacaaggt catcgccgtc cccgtcgagg accccgcta cgaccacatc     360 gaggacctcg acgacatccc gcagcagacg ctcgacgaga ttgacgagtt cttcgcgacc     420
tacaagaacc tcgaagccgg taaggaagtc gagacgctgg gctgggagga caaacaggcc     480
gccaaggacg ccatcgaaca cgcgatggat ctctacgaag agaacttcgc gtaa            534

<210> SEQ ID NO 2
<211> LENGTH: 177
<212> TYPE: PRT
<213> ORGANISM: Haloferax volcanii

<400> SEQUENCE: 2

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30
```

```
Glu Tyr Asp Lys Asp Ile Pro Gly Val Val Leu Asp Arg Val Leu His
         35                  40                  45

Ser Asn Val His Tyr Pro Ser Asp Tyr Gly Phe Ile Pro Gln Thr Tyr
 50                  55                  60

Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                 85                  90                  95

Met Asp Asp Asp Gly Glu Gln Asp Asp Lys Val Ile Ala Val Pro Val
            100                 105                 110

Glu Asp Pro Arg Tyr Asp His Ile Glu Asp Leu Asp Asp Ile Pro Gln
            115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 3
<211> LENGTH: 177
<212> TYPE: PRT
<213> ORGANISM: Haloferax sp.

<400> SEQUENCE: 3

Met Val Asn Leu Trp Glu Asp Met Glu Thr Gly Pro Asn Ala Pro Asp
 1               5                  10                  15

Glu Ile Tyr Ala Val Val Glu Cys Leu Lys Gly Glu Arg Asn Lys Tyr
                 20                  25                  30

Glu Tyr Asp Lys Asp Ile Pro Gly Val Val Leu Asp Arg Val Leu His
         35                  40                  45

Ser Asn Val His Tyr Pro Ser Asp Tyr Gly Phe Ile Pro Gln Thr Tyr
 50                  55                  60

Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                 85                  90                  95

Met Asp Asp Asp Gly Glu Gln Asp Asp Lys Val Ile Ala Val Pro Val
            100                 105                 110

Glu Asp Pro Arg Tyr Asp His Ile Glu Asp Leu Asp Asp Ile Pro Gln
            115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 4
<211> LENGTH: 177
<212> TYPE: PRT
<213> ORGANISM: Haloferax lucentense

<400> SEQUENCE: 4
```

```
Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Ile Pro Gln Thr Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Val
                100                 105                 110

Glu Asp Pro Arg Tyr Asp His Ile Glu Asp Leu Asp Asp Ile Pro Gln
            115                 120                 125

Gln Thr Leu Asp Glu Ile Asp Glu Phe Phe Ala Thr Tyr Lys Asn Leu
        130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 5
<211> LENGTH: 175
<212> TYPE: PRT
<213> ORGANISM: Haloferax alexandrines

<400> SEQUENCE: 5

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Ile Pro Gln Thr Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Val
                100                 105                 110

Glu Asp Pro Arg Tyr Asp His Ile Glu Asp Leu Asp Asp Ile Pro Gln
            115                 120                 125

Gln Thr Leu Asp Glu Ile Asp Glu Phe Phe Ala Thr Tyr Lys Asn Leu
        130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn
                165                 170                 175

<210> SEQ ID NO 6
```

```
<211> LENGTH: 177
<212> TYPE: PRT
<213> ORGANISM: Haloferax sp.

<400> SEQUENCE: 6

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Ile Pro Gln Thr Tyr
50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Val
            100                 105                 110

Glu Asp Pro Arg Tyr Asp His Ile Glu Asp Leu Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Gln Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 7
<211> LENGTH: 177
<212> TYPE: PRT
<213> ORGANISM: Haloferax sp.

<400> SEQUENCE: 7

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Ile Pro Gln Thr Tyr
50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Val
            100                 105                 110

Glu Asp Pro Arg Tyr Asp His Ile Glu Asp Leu Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Gln Gly Trp Glu Asp Lys Gln Ala
145                 150                 155                 160
```

```
Ala Lys Asp Ala Ile Glu His Ala Met Asp Leu Tyr Glu Glu Asn Phe
            165                 170                 175

Ala

<210> SEQ ID NO 8
<211> LENGTH: 177
<212> TYPE: PRT
<213> ORGANISM: Haloferax sp.

<400> SEQUENCE: 8

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Ile Pro Gln Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Val
            100                 105                 110

Glu Asp Pro Arg Tyr Asp His Ile Glu Asp Leu Asp Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Gln Gly Trp Glu Asp Lys Gln Ala
145                 150                 155                 160

Ala Lys Asp Ala Ile Glu His Ala Met Asp Leu Tyr Glu Glu Asn Phe
            165                 170                 175

Ala

<210> SEQ ID NO 9
<211> LENGTH: 177
<212> TYPE: PRT
<213> ORGANISM: Haloferax prahovense

<400> SEQUENCE: 9

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Ile Pro Gln Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ile
            100                 105                 110

Glu Asp Pro Arg Tyr Asp His Ile Glu Asp Leu Glu Asp Ile Pro Gln
        115                 120                 125
```

Gln Thr Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
            165                 170                 175

Ala

<210> SEQ ID NO 10
<211> LENGTH: 177
<212> TYPE: PRT
<213> ORGANISM: Haloferax gibbonsii

<400> SEQUENCE: 10

Met Val Asn Leu Trp Glu Asp Met Glu Thr Gly Pro Asp Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Ile Pro Gln Thr Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ile
            100                 105                 110

Glu Asp Pro Arg Tyr Asp His Ile Glu Asp Leu Glu Asp Ile Pro Gln
        115                 120                 125

Gln Thr Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
            165                 170                 175

Ala

<210> SEQ ID NO 11
<211> LENGTH: 177
<212> TYPE: PRT
<213> ORGANISM: Haloferax larsenii

<400> SEQUENCE: 11

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Met Pro Arg Thr Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys

```
                    85                  90                  95
Met Asp Asp Asp Gly Glu Gln Asp Lys Val Ile Ala Val Pro Ile
            100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 12
<211> LENGTH: 177
<212> TYPE: PRT
<213> ORGANISM: Haloferax sp.

<400> SEQUENCE: 12

Met Val Asn Leu Trp Glu Asp Met Glu Thr Gly Pro Asp Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Met Pro Gln Thr Tyr
50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ile
            100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 13
<211> LENGTH: 177
<212> TYPE: PRT
<213> ORGANISM: Haloferax elongans

<400> SEQUENCE: 13

Met Val Asn Leu Trp Glu Asp Met Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45
```

-continued

Ser Asn Val His Tyr Pro Ser Asp Tyr Gly Phe Met Pro Arg Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
            100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 14
<211> LENGTH: 177
<212> TYPE: PRT
<213> ORGANISM: Haloferax sulfurifontis

<400> SEQUENCE: 14

Met Val Asn Leu Trp Glu Asp Met Glu Thr Gly Pro Asp Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Gln Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ile
            100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ser Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala

<210> SEQ ID NO 15
<211> LENGTH: 177
<212> TYPE: PRT
<213> ORGANISM: Haloferax denitrificans

<400> SEQUENCE: 15

Met Val Asn Leu Trp Glu Asp Met Glu Thr Gly Pro Asp Ala Pro Asp
1               5                   10                  15

```
Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Gln Thr Tyr
 50                  55                  60

Tyr Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ile
                100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ser Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Asn Phe
                165                 170                 175

Ala
```

<210> SEQ ID NO 16
<211> LENGTH: 177
<212> TYPE: PRT
<213> ORGANISM: Haloferax mucosum

<400> SEQUENCE: 16

```
Met Ala Asn Leu Trp Glu Asp Met Glu Thr Gly Pro Asp Ala Pro Asp
 1               5                  10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Arg Thr Tyr
 50                  55                  60

Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Tyr Asp His Ile Glu Asp Leu Glu Asp Ile Pro Gln
            115                 120                 125

Gln Arg Leu Asp Glu Ile Asp Glu Phe Phe Ser Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu Tyr Phe
                165                 170                 175

Ala
```

<210> SEQ ID NO 17
<211> LENGTH: 177

<212> TYPE: PRT
<213> ORGANISM: Halorubrum hochstenium

<400> SEQUENCE: 17

Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Asp Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Gln Val
                165                 170                 175

Ala

<210> SEQ ID NO 18
<211> LENGTH: 177
<212> TYPE: PRT
<213> ORGANISM: Halorubrum tebenquichense

<400> SEQUENCE: 18

Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Asp Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Gln Val

Ala

```
<210> SEQ ID NO 19
<211> LENGTH: 177
<212> TYPE: PRT
<213> ORGANISM: Haloferax mediterranei

<400> SEQUENCE: 19
```

Met Val Asn Leu Trp Glu Asp Met Glu Thr Gly Pro Asp Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Arg Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Tyr Asp His Ile Glu Asp Leu Glu Asp Ile Pro Lys
        115                 120                 125

Gln Leu Arg Asp Glu Ile Asp Glu Phe Phe Ser Thr Tyr Lys Asn Leu
    130                 135                 140

Glu Glu Gly Lys Glu Val Glu Thr Leu Gly Trp Glu Asp Lys Gln Ala
145                 150                 155                 160

Ala Lys Asp Ala Ile Glu His Ala Met Asp Leu Tyr Glu Glu His Phe
                165                 170                 175

Ala

```
<210> SEQ ID NO 20
<211> LENGTH: 177
<212> TYPE: PRT
<213> ORGANISM: Halorubrum saccharovorum

<400> SEQUENCE: 20
```

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Asp Asp Ile Pro Gln
        115                 120                 125

```
Gln Thr Leu Asp Glu Ile Asp Glu Phe Phe Ser Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Phe
                165                 170                 175

Gln

<210> SEQ ID NO 21
<211> LENGTH: 177
<212> TYPE: PRT
<213> ORGANISM: Halostagnicola sp.

<400> SEQUENCE: 21

Met Val Asn Leu Trp Glu Asp Ile Glu Thr Gly Pro Asn Ala Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Lys Val Ile Ala Val Pro Ser
            100                 105                 110

Glu Asp Pro Arg Tyr Asp His Ile Glu Asp Leu Glu Asp Ile Pro Gln
        115                 120                 125

Gln Gln Leu Asp Glu Ile Asp Glu Phe Phe Ala Thr Tyr Lys Asn Leu
    130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Glu Glu Asn Phe
                165                 170                 175

Ala

<210> SEQ ID NO 22
<211> LENGTH: 177
<212> TYPE: PRT
<213> ORGANISM: Halorubrum sp.

<400> SEQUENCE: 22

Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Leu Met Lys
                85                  90                  95
```

```
Met Asp Asp Asp Gly Glu Gln Asp Lys Val Ile Ala Val Pro Thr
            100                 105                 110

Glu Asp Pro Arg Phe Asp His Ile Glu Asp Leu Glu Asp Ile Pro Gln
        115                 120                 125

Gln Ile Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Gln Val
                165                 170                 175

Ala

<210> SEQ ID NO 23
<211> LENGTH: 177
<212> TYPE: PRT
<213> ORGANISM: Natrialba chahannaoensis

<400> SEQUENCE: 23

Met Val Asn Leu Trp Glu Asp Ile Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
            100                 105                 110

Glu Asp Pro Arg Tyr Asp His Ile Glu Asp Leu Glu Asp Ile Pro Gln
        115                 120                 125

Gln Gln Leu Asp Glu Ile Asp Glu Phe Phe Ala Thr Tyr Lys Asn Leu
    130                 135                 140

Glu Ala Asp Lys Glu Val Glu Thr Leu Gly Trp Glu Asp Lys Gln Ala
145                 150                 155                 160

Ala Tyr Asp Ala Ile Glu His Ala Gln Asp Leu Tyr Glu Glu Asn Phe
                165                 170                 175

Glu

<210> SEQ ID NO 24
<211> LENGTH: 177
<212> TYPE: PRT
<213> ORGANISM: Natrialba hulunbeirensis

<400> SEQUENCE: 24

Met Val Asn Leu Trp Glu Asp Ile Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
```

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Tyr Asp His Ile Glu Asp Leu Glu Asp Ile Pro Gln
        115                 120                 125

Gln Gln Leu Asp Glu Ile Asp Glu Phe Phe Ala Thr Tyr Lys Asn Leu
    130                 135                 140

Glu Glu Gly Lys Glu Val Glu Thr Leu Gly Trp Glu Asp Arg Gln Ala
145                 150                 155                 160

Ala Tyr Asp Ala Ile Glu His Ala Gln Asp Leu Tyr Glu Glu Asn Phe
                165                 170                 175

Glu

<210> SEQ ID NO 25
<211> LENGTH: 177
<212> TYPE: PRT
<213> ORGANISM: Halostagnicola larsenii

<400> SEQUENCE: 25

Met Val Asn Leu Trp Glu Asp Ile Glu Thr Gly Pro Asn Ala Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Glu Asp Ile Pro Gln
        115                 120                 125

Gln Gln Leu Asp Glu Ile Asp Glu Phe Phe Lys Thr Tyr Lys Asn Leu
    130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Glu Glu Asn Phe
                165                 170                 175

Ala

<210> SEQ ID NO 26
<211> LENGTH: 177
<212> TYPE: PRT
<213> ORGANISM: Halobiforma lacisalsi

<400> SEQUENCE: 26

Met Val Asn Leu Trp Glu Asp Leu Glu Thr Gly Pro Asn Pro Pro Glu
1               5                   10                  15

```
Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Tyr Asp His Ile Glu Asp Leu Glu Asp Ile Pro Gln
            115                 120                 125

Gln Thr Leu Asp Glu Ile Asp Glu Phe Phe Ala Thr Tyr Lys Asn Leu
    130                 135                 140

Glu Glu Gly Lys Glu Val Glu Thr Leu Gly Trp Glu Asp Arg Glu Ala
145                 150                 155                 160

Ala Tyr Asp Ala Ile Glu His Ala Gln Asp Leu Tyr Glu Glu His Phe
                165                 170                 175

Glu

<210> SEQ ID NO 27
<211> LENGTH: 177
<212> TYPE: PRT
<213> ORGANISM: Natrialba taiwanensis

<400> SEQUENCE: 27

Met Val Asn Leu Trp Glu Asp Val Glu Thr Gly Pro Asn Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Tyr Asp His Ile Glu Asp Leu Asp Ile Pro Gln
            115                 120                 125

Gln Gln Leu Asp Glu Ile Asp Glu Phe Phe Ser Thr Tyr Lys Asn Leu
    130                 135                 140

Glu Ala Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Glu Glu His Phe
                165                 170                 175

Glu

<210> SEQ ID NO 28
<211> LENGTH: 177
<212> TYPE: PRT
```

<213> ORGANISM: Natrialba aegyptia

<400> SEQUENCE: 28

Met Val Asn Leu Trp Glu Asp Val Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Tyr Asp His Ile Glu Asp Leu Asp Asp Ile Pro Gln
        115                 120                 125

Gln Gln Leu Asp Glu Ile Asp Glu Phe Phe Ser Thr Tyr Lys Asn Leu
    130                 135                 140

Glu Ala Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Glu Glu His Phe
                165                 170                 175

Glu

<210> SEQ ID NO 29
<211> LENGTH: 176
<212> TYPE: PRT
<213> ORGANISM: Natrinema pellirubrum

<400> SEQUENCE: 29

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Asp Asp Ile Pro Gln
        115                 120                 125

Gln Gln Leu Asp Glu Ile Asp Glu Phe Phe Ala Thr Tyr Lys Asn Leu
    130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Asp Glu Asn Phe
                165                 170                 175

<210> SEQ ID NO 30
<211> LENGTH: 177
<212> TYPE: PRT
<213> ORGANISM: Haloterrigena limicola

<400> SEQUENCE: 30

```
Met Val Asn Leu Trp Glu Asp Leu Glu Thr Gly Pro Asn Ala Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Gln Asp Leu Asp Asp Ile Pro Gln
        115                 120                 125

Gln Gln Leu Asp Glu Ile Asp Glu Phe Phe Glu Thr Tyr Lys Asn Leu
    130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Glu Glu Asn Phe
                165                 170                 175

Gln
```

<210> SEQ ID NO 31
<211> LENGTH: 176
<212> TYPE: PRT
<213> ORGANISM: Haloterrigena thermotolerans

<400> SEQUENCE: 31

```
Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Asp Asp Ile Pro Gln
        115                 120                 125

Gln Gln Leu Asp Glu Ile Asp Glu Phe Phe Ala Thr Tyr Lys Asn Leu
    130                 135                 140
```

```
Glu Glu Gly Lys Glu Val Glu Thr Gln Gly Trp Glu Asp Lys Gln Ala
145                 150                 155                 160

Ala Tyr Asp Ala Ile Glu His Ala Gln Asp Leu Tyr Asp Glu Asn Phe
                165                 170                 175

<210> SEQ ID NO 32
<211> LENGTH: 177
<212> TYPE: PRT
<213> ORGANISM: Halorubrum lacusprofundi

<400> SEQUENCE: 32

Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Ser Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
                100                 105                 110

Glu Asp Pro Arg Phe Asp His Ile Glu Asp Leu Ser Asp Leu Pro Gln
            115                 120                 125

Gln Thr Leu Asp Glu Ile Asp Glu Phe Phe Ser Thr Tyr Lys Asn Leu
        130                 135                 140

Glu Ala Gly Lys Glu Val Glu Thr Leu Gly Trp Glu Asp Lys Gln Ala
145                 150                 155                 160

Ala Arg Asp Ala Ile Glu His Ala Gln Asp Leu Tyr Asp Glu Glu Phe
                165                 170                 175

Gln

<210> SEQ ID NO 33
<211> LENGTH: 177
<212> TYPE: PRT
<213> ORGANISM: Halorubrum californiensis

<400> SEQUENCE: 33

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Met Met Lys
                85                  90                  95

Met Asp Asp Asp Gly Glu Gln Asp Asp Lys Val Ile Ala Val Pro Thr
                100                 105                 110

Glu Asp Pro Arg Phe Asp His Ile Glu Asp Leu Asp Asp Ile Pro Gln
```

```
                115                 120                 125
Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Ala Ala
145                 150                 155                 160

Ala Lys Glu Ala Ile Glu His Ala Gln Asp Leu Tyr Asp Glu Gln Val
                165                 170                 175

Ala

<210> SEQ ID NO 34
<211> LENGTH: 177
<212> TYPE: PRT
<213> ORGANISM: Natrialba magadii

<400> SEQUENCE: 34

Met Val Asn Leu Trp Glu Asp Ile Glu Thr Gly Pro Asn Pro Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Glu Asp Ile Pro Gln
        115                 120                 125

Gln Gln Arg Asp Glu Ile Asp Glu Phe Phe Ala Thr Tyr Lys Asn Leu
    130                 135                 140

Glu Glu Gly Lys Glu Val Glu Thr Leu Gly Trp Glu Asp Lys Gln Ala
145                 150                 155                 160

Ala Tyr Asp Ala Ile Glu His Ala Gln Asp Leu Tyr Glu Glu Asn Phe
                165                 170                 175

Glu

<210> SEQ ID NO 35
<211> LENGTH: 176
<212> TYPE: PRT
<213> ORGANISM: Haloterrigena turkmenica

<400> SEQUENCE: 35

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
                20                  25                  30

Glu Tyr Glu Lys Asp Ile Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80
```

```
Thr Phe Pro Gly Cys Val Ile Glu Ala Arg Pro Val Ala Leu Met Lys
                85                  90                  95
Met Asp Asp Gly Glu Gln Asp Lys Val Ile Ala Val Pro Ser
            100                 105                 110
Glu Asp Pro Arg Tyr Asp His Ile Glu Asp Leu Asp Asp Ile Pro Gln
            115                 120                 125
Gln Gln Leu Asp Glu Ile Asp Glu Phe Phe Ala Thr Tyr Lys Asn Leu
        130                 135                 140
Glu Glu Gly Lys Glu Val Glu Thr Gln Gly Trp Glu Asp Lys Gln Ala
145                 150                 155                 160
Ala Tyr Asp Ala Ile Glu His Ala Gln Glu Leu Tyr Glu Glu Asn Phe
                165                 170                 175
```

<210> SEQ ID NO 36
<211> LENGTH: 176
<212> TYPE: PRT
<213> ORGANISM: Haloterrigena salina

<400> SEQUENCE: 36

```
Met Val Asn Leu Trp Glu Asp Leu Glu Thr Gly Pro Asn Pro Glu
1               5                   10                  15
Glu Ile Tyr Ala Val Val Glu Cys Leu Lys Gly Glu Arg Asn Lys Tyr
                20                  25                  30
Glu Tyr Glu Lys Asp Ile Pro Gly Val Val Leu Asp Arg Val Leu His
            35                  40                  45
Ser Asn Val His Tyr Pro Ser Asp Tyr Gly Phe Ile Pro Gln Ser Tyr
        50                  55                  60
Tyr Asp Asp Glu Asp Pro Phe Asp Val Leu Val Leu Val Glu Asp Gln
65                  70                  75                  80
Thr Phe Pro Gly Cys Val Ile Glu Ala Arg Pro Val Ala Leu Met Lys
                85                  90                  95
Met Asp Asp Asp Gly Glu Gln Asp Lys Val Ile Ala Val Pro Ser
            100                 105                 110
Glu Asp Pro Arg Tyr Asp His Ile Glu Asp Leu Asp Asp Ile Pro Gln
            115                 120                 125
Gln Gln Leu Asp Glu Ile Asp Glu Phe Phe Ala Thr Tyr Lys Asn Leu
        130                 135                 140
Glu Glu Gly Lys Glu Val Glu Thr Gln Gly Trp Glu Asp Lys Gln Ala
145                 150                 155                 160
Ala Tyr Asp Ala Ile Glu His Ala Gln Glu Leu Tyr Glu Glu Asn Phe
                165                 170                 175
```

<210> SEQ ID NO 37
<211> LENGTH: 177
<212> TYPE: PRT
<213> ORGANISM: Haloarcula sinaiiensis

<400> SEQUENCE: 37

```
Met Thr Asn Leu Trp Glu Asp Leu Glu Thr Gly Pro Asn Pro Glu
1               5                   10                  15
Glu Ile Tyr Ala Val Val Glu Cys Leu Lys Gly Glu Arg Asn Lys Tyr
                20                  25                  30
Glu Tyr Glu Lys Asp Ile Pro Gly Val Val Leu Asp Arg Val Leu His
            35                  40                  45
Ser Asn Val His Tyr Pro Ser Asp Tyr Gly Phe Ile Pro Gln Ser Tyr
        50                  55                  60
```

```
Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                 85                  90                  95

Met Asp Asp Gly Glu Gln Asp Lys Val Ile Ala Val Pro Thr
            100                 105                 110

Glu Asp Pro Arg Tyr Asp His Ile Glu Asp Leu Asp Ile Pro Gln
            115                 120                 125

Gln Thr Leu Asp Glu Ile Asp Glu Phe Phe Ser Thr Tyr Lys Asn Leu
            130                 135                 140

Glu Ala Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Phe
                165                 170                 175

Asn

<210> SEQ ID NO 38
<211> LENGTH: 177
<212> TYPE: PRT
<213> ORGANISM: Natronolimnobius innermongolicus

<400> SEQUENCE: 38

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
                20                  25                  30

Glu Tyr Glu Lys Asp Ile Pro Gly Val Val Leu Asp Arg Val Leu His
            35                  40                  45

Ser Asn Val His Tyr Pro Ser Asp Tyr Gly Phe Ile Pro Gln Ser Tyr
 50                  55                  60

Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                 85                  90                  95

Met Asp Asp Gly Glu Gln Asp Lys Val Ile Ala Val Pro Ser
            100                 105                 110

Glu Asp Pro Arg Tyr Asp His Ile Glu Asp Leu Asp Ile Pro Gln
            115                 120                 125

Gln Gln Leu Asp Glu Ile Asp Glu Phe Phe Ala Thr Tyr Lys Asn Leu
            130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Glu Glu Asn Phe
                165                 170                 175

Gln

<210> SEQ ID NO 39
<211> LENGTH: 177
<212> TYPE: PRT
<213> ORGANISM: Halorubrum arcis

<400> SEQUENCE: 39

Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30
```

```
Glu Tyr Asp Lys Asp Ile Pro Gly Val Val Leu Asp Arg Val Leu His
            35                  40                  45

Ser Asn Val His Tyr Pro Asp Tyr Gly Phe Ile Pro Gln Ser Tyr
 50                  55                  60

Tyr Asp Asp Glu Asp Pro Phe Asp Val Met Val Leu Val Glu Asp Gln
 65                  70                  75                  80

Thr Phe Pro Gly Cys Val Val Glu Ala Arg Pro Val Ala Met Met Lys
                 85                  90                  95

Met Asp Asp Asp Gly Glu Gln Asp Lys Val Ile Ala Val Pro Thr
                100                 105                 110

Glu Asp Pro Arg Phe Asp His Ile Glu Asp Leu Glu Asp Ile Pro Gln
                115                 120                 125

Gln Thr Leu Asp Glu Ile Asp Glu Phe Phe Ser Thr Tyr Lys Asn Leu
            130                 135                 140

Glu Glu Gly Lys Glu Val Glu Thr Leu Gly Trp Glu Asp Lys Gln Ala
145                 150                 155                 160

Ala Lys Glu Ala Ile Glu His Ala Gln Asp Leu Tyr Asp Glu Gln Val
                165                 170                 175

Ala

<210> SEQ ID NO 40
<211> LENGTH: 176
<212> TYPE: PRT
<213> ORGANISM: Natrinema versiforme

<400> SEQUENCE: 40

Met Val Asn Leu Trp Glu Asp Leu Glu Thr Gly Pro Asn Pro Glu
 1               5                  10                  15

Glu Ile Tyr Ala Val Val Glu Cys Leu Lys Gly Glu Arg Asn Lys Tyr
                 20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
 50                  55                  60

Tyr Asp Asp Glu Asp Pro Phe Asp Val Leu Val Leu Val Glu Asp Gln
 65                  70                  75                  80

Thr Phe Pro Gly Cys Val Ile Glu Ala Arg Pro Val Ala Leu Met Lys
                 85                  90                  95

Met Asp Asp Asp Gly Glu Gln Asp Lys Val Ile Ala Val Pro Ser
                100                 105                 110

Glu Asp Pro Arg Tyr Asp His Ile Glu Asp Leu Glu Asp Ile Pro Gln
                115                 120                 125

Gln Glu Leu Asp Glu Ile Asp Glu Phe Phe Ser Ser Tyr Lys Asn Leu
            130                 135                 140

Glu Glu Gly Lys Glu Val Glu Thr Leu Gly Trp Glu Asp Lys Gln Ala
145                 150                 155                 160

Ala Tyr Asp Ala Ile Glu His Ala Gln Asp Leu Tyr Asp Glu Asn Phe
                165                 170                 175

<210> SEQ ID NO 41
<211> LENGTH: 177
<212> TYPE: PRT
<213> ORGANISM: Halopiger xanaduensis

<400> SEQUENCE: 41
```

```
Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ser
                100                 105                 110

Glu Asp Pro Arg Tyr Asp His Ile Glu Asp Leu Glu Asp Ile Pro Gln
            115                 120                 125

Gln Gln Leu Asp Glu Ile Asp Glu Phe Phe Ala Thr Tyr Lys Asn Leu
    130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Glu Glu Asn Phe
                165                 170                 175

Gln
```

<210> SEQ ID NO 42
<211> LENGTH: 177
<212> TYPE: PRT
<213> ORGANISM: Halorubrum lipolyticum

<400> SEQUENCE: 42

```
Met Val Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Leu Met Lys
                85                  90                  95

Met Asp Asp Asp Gly Glu Gln Asp Asp Lys Val Ile Ala Val Pro Thr
                100                 105                 110

Glu Asp Pro Arg Phe Asp His Ile Asp Asp Leu Glu Asp Ile Pro Gln
            115                 120                 125

Gln Ile Arg Asp Glu Ile Asp Glu Phe Phe Ser Thr Tyr Lys Asn Leu
    130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Glu Phe
                165                 170                 175

Gln
```

```
<210> SEQ ID NO 43
<211> LENGTH: 177
<212> TYPE: PRT
<213> ORGANISM: Haloarcula amylolytica

<400> SEQUENCE: 43

Met Thr Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Glu Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Val
            100                 105                 110

Glu Asp Pro Arg Tyr Asp His Ile Glu Asp Leu Asp Asp Ile Pro Gln
        115                 120                 125

Gln Thr Leu Asp Glu Ile Asp Glu Phe Phe Ser Thr Tyr Lys Asn Leu
    130                 135                 140

Glu Glu Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Glu Phe
                165                 170                 175

Asn

<210> SEQ ID NO 44
<211> LENGTH: 177
<212> TYPE: PRT
<213> ORGANISM: Haloarcula sp.

<400> SEQUENCE: 44

Met Thr Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Glu Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ile
            100                 105                 110

Glu Asp Pro Arg Tyr Asp His Ile Glu Asp Leu Asp Asp Ile Pro Gln
        115                 120                 125

Gln Thr Leu Asp Glu Ile Asp Glu Phe Phe Ser Thr Tyr Lys Asn Leu
    130                 135                 140

Glu Glu Gly Lys Glu Val Glu Thr Leu Gly Trp Glu Asp Lys Glu Ala
145                 150                 155                 160
```

Ala Lys Asp Ala Ile Val His Ala Gln Glu Leu Tyr Asp Glu Glu Phe
            165                 170                 175

Asn

<210> SEQ ID NO 45
<211> LENGTH: 177
<212> TYPE: PRT
<213> ORGANISM: Haloarcula japonica

<400> SEQUENCE: 45

Met Thr Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Glu Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ile
            100                 105                 110

Glu Asp Pro Arg Tyr Asp His Ile Glu Asp Leu Asp Asp Ile Pro Gln
        115                 120                 125

Gln Thr Leu Asp Glu Ile Asp Glu Phe Phe Ser Thr Tyr Lys Asn Leu
    130                 135                 140

Glu Glu Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Glu Phe
            165                 170                 175

Asn

<210> SEQ ID NO 46
<211> LENGTH: 177
<212> TYPE: PRT
<213> ORGANISM: Haloarcula argentinensis

<400> SEQUENCE: 46

Met Thr Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Glu Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ile
            100                 105                 110

Glu Asp Pro Arg Tyr Asp His Ile Glu Asp Leu Asp Asp Ile Pro Gln

```
            115                 120                 125
Gln Thr Leu Asp Glu Ile Asp Glu Phe Phe Ser Thr Tyr Lys Asn Leu
    130                 135                 140
Glu Glu Gly Lys Glu Val Glu Thr Leu Gly Trp Glu Asp Lys Glu Ala
145                 150                 155                 160
Ala Lys Asp Ala Ile Val His Ala Gln Glu Leu Tyr Asp Glu Glu Phe
                165                 170                 175
Asn

<210> SEQ ID NO 47
<211> LENGTH: 177
<212> TYPE: PRT
<213> ORGANISM: Halorubrum distributum

<400> SEQUENCE: 47

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80

Thr Phe Pro Gly Cys Val Val Glu Ala Arg Pro Val Ala Met Met Lys
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Glu Asp Ile Pro Gln
        115                 120                 125

Gln Thr Leu Asp Glu Ile Asp Glu Phe Phe Ala Thr Tyr Lys Asn Leu
    130                 135                 140

Glu Ala Gly Lys Glu Val Glu Thr Leu Gly Trp Glu Asp Lys Ala Ala
145                 150                 155                 160

Ala Lys Glu Ala Ile Glu His Ala Gln Asp Leu Tyr Asp Glu Gln Val
                165                 170                 175

Ala

<210> SEQ ID NO 48
<211> LENGTH: 177
<212> TYPE: PRT
<213> ORGANISM: Halorubrum litoreum

<400> SEQUENCE: 48

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Val Leu Val Glu Asp Gln
65                  70                  75                  80
```

```
Thr Phe Pro Gly Cys Val Val Glu Ala Arg Pro Val Ala Met Met Lys
                85                  90                  95
Met Asp Asp Asp Gly Glu Gln Asp Lys Val Ile Ala Val Pro Thr
            100                 105                 110
Glu Asp Pro Arg Phe Asp His Ile Glu Asp Leu Glu Asp Ile Pro Gln
        115                 120                 125
Gln Thr Leu Asp Glu Ile Asp Glu Phe Phe Ala Thr Tyr Lys Asn Leu
    130                 135                 140
Glu Ala Gly Lys Glu Val Glu Thr Leu Gly Trp Glu Asp Lys Ala Ala
145                 150                 155                 160
Ala Lys Glu Ala Ile Glu His Ala Gln Asp Leu Tyr Asp Glu Gln Val
                165                 170                 175

Ala

<210> SEQ ID NO 49
<211> LENGTH: 177
<212> TYPE: PRT
<213> ORGANISM: Halorubrum distributum

<400> SEQUENCE: 49

Met Ala Asn Leu Trp Glu Asp Leu Glu Thr Gly Pro Asn Ala Pro Asp
1               5                   10                  15
Glu Ile Tyr Ala Val Val Glu Cys Leu Lys Gly Glu Arg Asn Lys Tyr
            20                  25                  30
Glu Tyr Asp Lys Asp Ile Pro Gly Val Val Leu Asp Arg Val Leu His
        35                  40                  45
Ser Asn Val His Tyr Pro Tyr Asp Tyr Gly Phe Ile Pro Gln Ser Tyr
    50                  55                  60
Tyr Asp Asp Glu Asp Pro Phe Asp Val Met Val Leu Val Glu Asp Gln
65                  70                  75                  80
Thr Phe Pro Gly Cys Val Val Glu Ala Arg Pro Val Ala Met Met Lys
                85                  90                  95
Met Asp Asp Asp Gly Glu Gln Asp Lys Val Ile Ala Val Pro Thr
            100                 105                 110
Glu Asp Pro Arg Phe Asp His Ile Glu Asp Leu Glu Asp Ile Pro Gln
        115                 120                 125
Gln Thr Leu Asp Glu Ile Asp Glu Phe Phe Ala Thr Tyr Lys Asn Leu
    130                 135                 140
Glu Ala Gly Lys Glu Val Glu Thr Leu Gly Trp Glu Asp Lys Ala Ala
145                 150                 155                 160
Ala Lys Glu Ala Ile Glu His Ala Gln Asp Leu Tyr Asp Glu Gln Val
                165                 170                 175

Ala

<210> SEQ ID NO 50
<211> LENGTH: 177
<212> TYPE: PRT
<213> ORGANISM: Haloarcula vallismortis

<400> SEQUENCE: 50

Met Thr Asn Leu Trp Glu Asp Leu Glu Thr Gly Pro Asn Pro Pro Glu
1               5                   10                  15
Glu Ile Tyr Ala Val Val Glu Cys Leu Lys Gly Glu Arg Asn Lys Tyr
            20                  25                  30
Glu Tyr Glu Lys Asp Ile Pro Gly Val Val Leu Asp Arg Val Leu His
        35                  40                  45
```

```
Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Tyr Asp His Ile Glu Asp Leu Asp Ile Pro Gln
            115                 120                 125

Gln Thr Leu Asp Glu Ile Asp Glu Phe Phe Ala Thr Tyr Lys Asn Leu
            130                 135                 140

Glu Glu Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Phe
                165                 170                 175

Asn
```

<210> SEQ ID NO 51
<211> LENGTH: 177
<212> TYPE: PRT
<213> ORGANISM: Halorubrum terrestre

<400> SEQUENCE: 51

```
Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Leu Val Glu Asp Gln
65                  70                  75                  80

Thr Phe Pro Gly Cys Val Val Glu Ala Arg Pro Val Ala Met Met Lys
                85                  90                  95

Met Asp Asp Asp Gly Glu Gln Asp Lys Val Ile Ala Val Pro Thr
                100                 105                 110

Glu Asp Pro Arg Phe Asp His Ile Glu Asp Leu Glu Asp Ile Pro Gln
            115                 120                 125

Gln Thr Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Ala Ala
145                 150                 155                 160

Ala Lys Glu Ala Ile Glu His Ala Gln Asp Leu Tyr Asp Glu Gln Val
                165                 170                 175

Ala
```

<210> SEQ ID NO 52
<211> LENGTH: 178
<212> TYPE: PRT
<213> ORGANISM: Halomicrobium mukohataei

<400> SEQUENCE: 52

Met Met Thr Asn Leu Trp Glu Asp Leu Glu Thr Gly Pro Asn Pro Pro

```
            1               5                  10                 15
          Glu Glu Ile Tyr Ala Val Val Glu Cys Leu Lys Gly Glu Arg Asn Lys
                          20                  25                 30
          Tyr Glu Tyr Asp Lys Asp Val Pro Gly Val Val Leu Asp Arg Val Leu
                          35                  40                 45
          His Ser Asn Val His Tyr Pro Ser Asp Tyr Gly Phe Ile Pro Gln Ser
                          50                  55                 60
          Tyr Tyr Asp Asp Glu Asp Pro Phe Asp Val Leu Val Leu Val Glu Asp
           65                  70                  75                 80
          Gln Thr Phe Pro Gly Cys Ile Ile Glu Ala Arg Pro Val Ala Leu Met
                          85                  90                 95
          Lys Met Asp Asp Asp Gly Glu Gln Asp Lys Val Ile Ala Val Pro
                          100                 105                110
          Ser Glu Asp Pro Arg Tyr Asp His Ile Glu Asp Leu Asp Ile Pro
                          115                 120                125
          Gln Gln Gln Leu Asp Glu Ile Asp Glu Phe Phe Ala Thr Tyr Lys Asn
                          130                 135                140
          Leu Glu Ala Gly Lys Glu Val Glu Thr Leu Gly Trp Glu Asp Lys Gln
           145                 150                 155                160
          Ala Ala Tyr Asp Ala Ile Glu His Ala Gln Glu Leu Tyr Asp Glu Gln
                          165                 170                175
          Ile Ala

<210> SEQ ID NO 53
<211> LENGTH: 193
<212> TYPE: PRT
<213> ORGANISM: Haloarcula hispanica

<400> SEQUENCE: 53

Met Ala Ile Thr Lys Gly Phe Phe Asp Gly Val Ala Gln Ser Pro Val
           1               5                  10                 15
          Met Thr Asn Leu Trp Glu Asp Leu Glu Thr Gly Pro Asn Pro Pro Glu
                          20                  25                 30
          Glu Ile Tyr Ala Val Val Glu Cys Leu Lys Gly Glu Arg Asn Lys Tyr
                          35                  40                 45
          Glu Tyr Glu Lys Asp Ile Pro Gly Val Val Leu Asp Arg Val Leu His
                          50                  55                 60
          Ser Asn Val His Tyr Pro Ser Asp Tyr Gly Phe Ile Pro Gln Ser Tyr
           65                  70                  75                 80
          Tyr Asp Asp Glu Asp Pro Phe Asp Val Leu Val Leu Val Glu Asp Gln
                          85                  90                 95
          Thr Phe Pro Gly Cys Val Ile Glu Ala Arg Pro Val Ala Leu Met Lys
                          100                 105                110
          Met Asp Asp Asp Gly Glu Gln Asp Lys Val Ile Ala Val Pro Ile
                          115                 120                125
          Glu Asp Pro Arg Tyr Asp His Ile Glu Asp Leu Asp Ile Pro Gln
                          130                 135                140
          Gln Thr Leu Asp Glu Ile Asp Glu Phe Phe Ser Thr Tyr Lys Asn Leu
           145                 150                 155                160
          Glu Glu Gly Lys Glu Val Glu Thr Leu Gly Trp Glu Asp Lys Glu Ala
                          165                 170                175
          Ala Lys Asp Ala Ile Val His Ala Gln Glu Leu Tyr Asp Glu Glu Phe
                          180                 185                190
          Asn
```

<210> SEQ ID NO 54
<211> LENGTH: 193
<212> TYPE: PRT
<213> ORGANISM: Haloarcula hispanica

<400> SEQUENCE: 54

Met Ala Ile Thr Lys Gly Phe Phe Asp Gly Val Ala Gln Ser Pro Val
1               5                   10                  15

Met Thr Asn Leu Trp Glu Asp Leu Glu Thr Gly Pro Asn Pro Pro Glu
            20                  25                  30

Glu Ile Tyr Ala Val Val Glu Cys Leu Lys Gly Glu Arg Asn Lys Tyr
        35                  40                  45

Glu Tyr Glu Lys Asp Ile Pro Gly Val Val Leu Asp Arg Val Leu His
    50                  55                  60

Ser Asn Val His Tyr Pro Ser Asp Tyr Gly Phe Ile Pro Gln Ser Tyr
65                  70                  75                  80

Tyr Asp Asp Glu Asp Pro Phe Asp Val Leu Val Leu Val Glu Asp Gln
                85                  90                  95

Thr Phe Pro Gly Cys Val Ile Glu Ala Arg Pro Val Ala Leu Met Lys
            100                 105                 110

Met Asp Asp Asp Gly Glu Gln Asp Lys Val Ile Ala Val Pro Ile
        115                 120                 125

Glu Asp Pro Arg Tyr Asp His Ile Glu Asp Leu Asp Ile Pro Gln
    130                 135                 140

Gln Thr Leu Asp Glu Ile Asp Glu Phe Phe Ser Thr Tyr Lys Asn Leu
145                 150                 155                 160

Glu Glu Gly Lys Glu Val Glu Thr Leu Gly Trp Glu Asp Lys Glu Ala
                165                 170                 175

Ala Lys Asp Ala Ile Val His Ala Gln Glu Leu Tyr Asp Glu Glu Phe
            180                 185                 190

Asn

<210> SEQ ID NO 55
<211> LENGTH: 177
<212> TYPE: PRT
<213> ORGANISM: Halorubrum coriense

<400> SEQUENCE: 55

Met Ala Asn Leu Trp Glu Glu Leu Glu Thr Gly Pro Asn Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Tyr Asp Tyr Gly Phe Ile Pro Gln Ser Tyr
    50                  55                  60

Tyr Asp Asp Glu Asp Pro Phe Asp Val Met Leu Val Glu Asp Gln
65                  70                  75                  80

Thr Phe Pro Gly Cys Val Val Glu Ala Arg Pro Val Ala Leu Met Lys
                85                  90                  95

Met Asp Asp Asp Gly Glu Gln Asp Lys Val Ile Ala Val Pro Thr
            100                 105                 110

Glu Asp Pro Arg Phe Asp His Ile Glu Asp Leu Glu Asp Ile Pro Gln
        115                 120                 125

Gln Thr Leu Asp Glu Ile Asp Glu Phe Phe Ser Thr Tyr Lys Asn Leu
            130                 135                 140

Glu Ala Gly Lys Glu Val Glu Thr Leu Gly Trp Glu Asp Lys Ala Ala
145                 150                 155                 160

Ala Lys Glu Ala Ile Glu His Ala Gln Glu Leu Tyr Asp Glu Gln Phe
                165                 170                 175

Ala

<210> SEQ ID NO 56
<211> LENGTH: 177
<212> TYPE: PRT
<213> ORGANISM: Halorubrum kocurii

<400> SEQUENCE: 56

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Phe Asp His Ile Asp Leu Asp Asp Ile Pro Lys
            115                 120                 125

Gln Ile Arg Asp Glu Ile Asp Glu Phe Phe Ser Thr Tyr Lys Asn Leu
            130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Glu Phe
                165                 170                 175

Gln

<210> SEQ ID NO 57
<211> LENGTH: 176
<212> TYPE: PRT
<213> ORGANISM: Natrinema sp.

<400> SEQUENCE: 57

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

```
Met Asp Asp Gly Glu Gln Asp Lys Val Ile Ala Val Pro Ser
            100                 105                 110

Glu Asp Pro Arg Tyr Asp His Ile Glu Asp Leu Asp Ile Pro Gln
        115                 120                 125

Gln Gln Leu Asp Glu Ile Asp Glu Phe Phe Ala Thr Tyr Lys Asn Leu
130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Asp Glu His Phe
                165                 170                 175

<210> SEQ ID NO 58
<211> LENGTH: 176
<212> TYPE: PRT
<213> ORGANISM: Natrinema gari

<400> SEQUENCE: 58

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Gly Glu Gln Asp Lys Val Ile Ala Val Pro Ser
            100                 105                 110

Glu Asp Pro Arg Tyr Asp His Ile Glu Asp Leu Asp Ile Pro Gln
        115                 120                 125

Gln Gln Leu Asp Glu Ile Asp Glu Phe Phe Ala Thr Tyr Lys Asn Leu
130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Asp Glu His Phe
                165                 170                 175

<210> SEQ ID NO 59
<211> LENGTH: 176
<212> TYPE: PRT
<213> ORGANISM: Natrinema pallidum

<400> SEQUENCE: 59

Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80
```

```
Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ser
            100                 105                 110

Glu Asp Pro Arg Tyr Asp His Ile Glu Asp Leu Asp Asp Ile Pro Gln
            115                 120                 125

Gln Gln Leu Asp Glu Ile Asp Glu Phe Phe Ala Thr Tyr Lys Asn Leu
        130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Asp Glu His Phe
                165                 170                 175

<210> SEQ ID NO 60
<211> LENGTH: 176
<212> TYPE: PRT
<213> ORGANISM: Natrinema altunense

<400> SEQUENCE: 60

Met Val Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ser
            100                 105                 110

Glu Asp Pro Arg Tyr Asp His Ile Glu Asp Leu Asp Asp Ile Pro Gln
            115                 120                 125

Gln Gln Leu Asp Glu Ile Asp Glu Phe Phe Ala Thr Tyr Lys Asn Leu
        130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Asp Glu His Phe
                165                 170                 175

<210> SEQ ID NO 61
<211> LENGTH: 177
<212> TYPE: PRT
<213> ORGANISM: Haloarcula californiae

<400> SEQUENCE: 61

Met Thr Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
            20                  25                  30

Glu Tyr Glu Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60
```

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Gly Glu Gln Asp Asp Lys Val Ile Ala Val Pro Thr
            100                 105                 110

Glu Asp Pro Arg Tyr Asp His Ile Glu Asp Leu Asp Asp Ile Pro Gln
            115                 120                 125

Gln Thr Leu Asp Glu Ile Asp Glu Phe Phe Ser Thr Tyr Lys Asn Leu
        130                 135                 140

Glu Glu Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Glu Phe
                165                 170                 175

Asn

<210> SEQ ID NO 62
<211> LENGTH: 177
<212> TYPE: PRT
<213> ORGANISM: Halorubrum saccharovorum

<400> SEQUENCE: 62

Met Ala Asn Leu Trp Glu Asp Leu Glu Thr Gly Pro Asn Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Glu Asp Pro Phe Asp Val Met Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
            100                 105                 110

Glu Asp Pro Arg Phe Asp His Ile Asp Asp Leu Glu Asp Ile Pro Glu
            115                 120                 125

Gln Ile Arg Asp Glu Ile Asp Glu Phe Phe Ser Thr Tyr Lys Asn Leu
        130                 135                 140

Glu Ala Gly Lys Glu Val Glu Thr Leu Gly Trp Glu Asp Lys Gln Ala
145                 150                 155                 160

Ala Lys Asp Ala Ile Glu His Ala Gln Asp Leu Tyr Asp Glu Glu Phe
                165                 170                 175

Gln

<210> SEQ ID NO 63
<211> LENGTH: 177
<212> TYPE: PRT
<213> ORGANISM: Haloarcula marismortui

<400> SEQUENCE: 63

Met Thr Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr

```
                20              25              30
Glu Tyr Glu Lys Asp Ile Pro Gly Val Val Leu Asp Arg Val Leu His
            35                  40                      45

Ser Asn Val His Tyr Pro Ser Asp Tyr Gly Phe Ile Pro Gln Ser Tyr
 50                      55                  60

Tyr Asp Asp Glu Asp Pro Phe Asp Val Leu Val Leu Val Glu Asp Gln
65                   70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
                100                 105                 110

Glu Asp Pro Arg Tyr Asp His Ile Glu Asp Leu Asp Asp Met Pro Gln
            115                 120                 125

Gln Thr Leu Asp Glu Ile Asp Glu Phe Phe Ser Thr Tyr Lys Asn Leu
            130                 135                 140

Glu Glu Gly Lys Glu Val Glu Thr Leu Gly Trp Glu Asp Lys Glu Ala
145                 150                 155                 160

Ala Lys Asp Ala Ile Val His Ala Gln Glu Leu Tyr Asp Glu Glu Phe
                165                 170                 175

Asn

<210> SEQ ID NO 64
<211> LENGTH: 177
<212> TYPE: PRT
<213> ORGANISM: Halovivax ruber

<400> SEQUENCE: 64

Met Pro Asn Leu Trp Glu Glu Leu Glu Thr Gly Pro Asn Pro Pro Glu
1               5                   10                  15

Thr Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                      45

Ser Asn Val His Tyr Pro Ser Asp Tyr Gly Phe Ile Pro Gln Thr Tyr
 50                      55                  60

Tyr Asp Asp Glu Asp Pro Phe Asp Val Leu Val Leu Val Glu Asp Gln
65                   70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Thr
                100                 105                 110

Glu Asp Pro Arg Phe Asp His Ile Glu Asp Leu Ala Asp Ile Pro Gln
            115                 120                 125

Gln Gln Leu Asp Glu Ile Asp Glu Phe Phe Ala Thr Tyr Lys Asn Leu
            130                 135                 140

Glu Ala Gly Lys Glu Val Glu Thr Leu Gly Trp Glu Asp Lys Gln Ala
145                 150                 155                 160

Ala Met Asp Ala Ile Glu His Ala Gln Asp Leu Tyr Glu Glu His Phe
                165                 170                 175

Gly

<210> SEQ ID NO 65
<211> LENGTH: 176
<212> TYPE: PRT
<213> ORGANISM: Natronococcus jeotgali
```

<400> SEQUENCE: 65

```
Met Val Asn Leu Trp Glu Glu Leu Glu Thr Gly Pro Asn Ala Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ala Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Asp Lys Val Ile Ala Val Pro Ser
                100                 105                 110

Glu Asp Pro Arg Tyr Asp His Ile Glu Asp Leu Glu Asp Ile Pro Gln
            115                 120                 125

Gln Gln Leu Asp Glu Ile Asp Glu Phe Phe Ala Thr Tyr Lys Asn Leu
        130                 135                 140

Glu Glu Gly Lys Glu Val Glu Thr Gln Gly Trp Glu Asp Lys Gln Ala
145                 150                 155                 160

Ala Tyr Asp Ala Ile Glu His Ala Gln Glu Leu Tyr Glu Glu His Phe
                165                 170                 175
```

<210> SEQ ID NO 66
<211> LENGTH: 177
<212> TYPE: PRT
<213> ORGANISM: Natronobacterium gregoryi

<400> SEQUENCE: 66

```
Met Val Asn Leu Trp Glu Asp Leu Glu Thr Gly Pro Asn Pro Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Ser
                100                 105                 110

Glu Asp Pro Arg Tyr Asp His Ile Glu Asp Leu Glu Asp Ile Pro Gln
            115                 120                 125

Gln Gln Arg Asp Glu Ile Asp Glu Phe Phe Thr Thr Tyr Lys Asn Leu
        130                 135                 140

Glu Glu Gly Lys Glu Val Glu Thr Leu Gly Trp Glu Asp Arg Gln Ala
145                 150                 155                 160

Ala Tyr Asp Ala Ile Glu His Ala Gln Asp Leu Tyr Glu Glu His Phe
                165                 170                 175

Glu
```

<210> SEQ ID NO 67
<211> LENGTH: 177
<212> TYPE: PRT
<213> ORGANISM: Halovivax asiaticus

<400> SEQUENCE: 67

Met Pro Asn Leu Trp Glu Glu Leu Glu Thr Gly Pro Asn Pro Pro Glu
1               5                   10                  15

Thr Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Thr Tyr
    50                  55                  60

Tyr Asp Asp Glu Asp Pro Phe Asp Val Leu Val Leu Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Ala Asp Ile Pro Gln
        115                 120                 125

Gln Gln Leu Asp Glu Ile Asp Glu Phe Ala Thr Tyr Lys Asn Leu
    130                 135                 140

Glu Ala Gly Lys Glu Val Glu Thr Leu Gly Trp Glu Asp Lys Gln Ala
145                 150                 155                 160

Ala Ile Asp Ala Ile Glu His Ala Gln Asp Leu Tyr Glu Glu His Phe
                165                 170                 175

Gly

<210> SEQ ID NO 68
<211> LENGTH: 179
<212> TYPE: PRT
<213> ORGANISM: Natronomonas pharaonis

<400> SEQUENCE: 68

Met Ala Gly Ala Asn Leu Trp Glu Asp Leu Glu Thr Gly Pro Asn Ala
1               5                   10                  15

Pro Glu Glu Ile Tyr Ala Val Val Glu Cys Leu Lys Gly Glu Arg Asn
            20                  25                  30

Lys Tyr Glu Tyr Asp Lys Asp Ile Pro Gly Val Met Leu Asp Arg Val
        35                  40                  45

Leu His Ser Asn Val His Tyr Pro Gly Asp Tyr Gly Phe Ile Pro Gln
    50                  55                  60

Ser Tyr Tyr Asp Asp Glu Asp Pro Phe Asp Val Leu Val Leu Val Glu
65                  70                  75                  80

Asp Gln Thr Phe Pro Gly Cys Ile Ile Glu Ala Arg Pro Val Ala Leu
                85                  90                  95

Met Lys Met Asp Asp Asp Gly Glu Gln Asp Asp Lys Val Ile Ala Val
            100                 105                 110

Pro Ser Glu Asp Pro Arg Tyr Asp His Ile Glu Asp Leu Glu Asp Ile
        115                 120                 125

Pro Gln Gln Thr Leu Asp Glu Ile Asp Glu Phe Phe Glu Thr Tyr Lys
    130                 135                 140

Asn Leu Glu Glu Gly Lys Glu Val Glu Thr Gln Gly Trp Glu Asp Lys

```
                        145                 150                 155                 160
Gln Ala Ala Phe Asp Ala Ile Glu His Ala Gln Asp Leu Tyr Glu Glu
                165                 170                 175

His Phe Gly

<210> SEQ ID NO 69
<211> LENGTH: 176
<212> TYPE: PRT
<213> ORGANISM: Natronococcus occultus

<400> SEQUENCE: 69

Met Val Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Asp Gly Glu Gln Asp Lys Val Ile Ala Val Pro Ser
                100                 105                 110

Glu Asp Pro Arg Tyr Asp His Ile Glu Asp Leu Glu Asp Ile Pro Gln
            115                 120                 125

Gln Gln Leu Asp Glu Ile Asp Glu Phe Phe Ala Thr Tyr Lys Asn Leu
    130                 135                 140

Glu Glu Gly Lys Glu Val Ala Thr Glu Gly Trp Glu Asp Arg Gln Ala
145                 150                 155                 160

Ala Tyr Asp Ala Ile Glu His Ala Gln Glu Leu Tyr Asp Glu Asn Phe
                165                 170                 175

<210> SEQ ID NO 70
<211> LENGTH: 179
<212> TYPE: PRT
<213> ORGANISM: Natronomonas moolapensis

<400> SEQUENCE: 70

Met Ala Gly Ala Asn Leu Trp Glu Asp Leu Glu Thr Gly Pro Asn Ala
1               5                   10                  15

Pro Glu Glu Ile Tyr Ala Val Val Glu Cys Leu Lys Gly Glu Arg Asn
                20                  25                  30

Lys Tyr Glu Tyr Asp Lys Asp Ile Pro Gly Val Val Leu Asp Arg Val
            35                  40                  45

Leu His Ser Asn Val His Tyr Pro Ser Asp Tyr Gly Phe Ile Pro Gln
    50                  55                  60

Ser Tyr Tyr Asp Asp Glu Asp Pro Phe Asp Val Leu Val Leu Val Glu
65                  70                  75                  80

Asp Gln Thr Phe Pro Gly Cys Val Val Glu Ala Arg Pro Val Ala Leu
                85                  90                  95

Met Lys Met Asp Asp Asp Gly Glu Gln Asp Lys Val Ile Ala Val
                100                 105                 110

Pro Thr Glu Asp Pro Arg Tyr Asp His Ile Glu Asp Leu Ala Asp Ile
            115                 120                 125
```

Pro Gln Gln Gln Leu Asp Glu Ile Asp Glu Phe Phe Asn Thr Tyr Lys
            130                 135                 140

Asn Leu Glu Ala Gly Lys Glu Val Glu Thr Gln Gly Trp Glu Asp Arg
145                 150                 155                 160

Gln Ala Ala Met Asp Ala Ile Glu His Ala Gln Glu Leu Tyr Glu Glu
                165                 170                 175

His Phe Asp

<210> SEQ ID NO 71
<211> LENGTH: 177
<212> TYPE: PRT
<213> ORGANISM: Haladaptatus paucihalophilus

<400> SEQUENCE: 71

Met Thr Asn Leu Trp Glu Asp Leu Glu Thr Gly Pro Asn Ala Pro Glu
1               5                   10                  15

Glu Ile Tyr Ala Val Val Glu Cys Leu Lys Gly Asp Arg Asn Lys Tyr
            20                  25                  30

Glu Tyr Asp Lys Asp Ile Pro Gly Val Met Leu Asp Arg Val Leu His
        35                  40                  45

Ser Asn Val His Tyr Pro Gly Asp Tyr Gly Phe Ile Pro Gln Ser Tyr
    50                  55                  60

Tyr Asp Asp Glu Asp Pro Phe Asp Val Leu Val Leu Val Glu Asp Ser
65                  70                  75                  80

Thr Phe Pro Gly Cys Val Ile Glu Ala Arg Pro Val Ala Met Met Lys
                85                  90                  95

Met Asp Asp Asp Gly Glu Gln Asp Asp Lys Val Ile Ala Val Pro Ile
            100                 105                 110

Glu Asp Pro Arg Phe Asp His Ile Glu Asp Val Glu Asp Ile Pro Gln
        115                 120                 125

Gln Thr Lys Asp Glu Ile Asp Glu Phe Phe Ser Thr Tyr Lys Asn Leu
    130                 135                 140

Glu Ala Gly Lys Glu Val Glu Thr Leu Gly Trp Glu Asp Lys Gln Ala
145                 150                 155                 160

Ala Tyr Asp Ala Ile Glu His Ser Gln Glu Leu Tyr Asp Glu Asn Phe
                165                 170                 175

Asn

<210> SEQ ID NO 72
<211> LENGTH: 177
<212> TYPE: PRT
<213> ORGANISM: Halogranum salarium

<400> SEQUENCE: 72

Met Thr Asn Leu Trp Glu Asp Leu Glu Thr Gly Pro Asn Ala Pro Glu
1               5                   10                  15

Thr Ile Tyr Ala Val Val Glu Cys Leu Lys Gly Glu Arg Asn Lys Tyr
            20                  25                  30

Glu Tyr Asp Lys Asp Ile Pro Ala Val Val Leu Asp Arg Val Leu His
        35                  40                  45

Ser Asn Val His Tyr Pro Ser Asp Tyr Gly Phe Ile Pro Gln Ser Phe
    50                  55                  60

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys

```
                      85                  90                  95
Met Asp Asp Gly Glu Gln Asp Lys Val Ile Ala Val Pro Thr
            100                 105                 110
Glu Asp Pro Arg Tyr Asp His Ile Glu Asp Leu Glu Asp Ile Pro Gln
            115                 120                 125
Gln Gln Leu Asp Glu Ile Asp Glu Phe Phe Lys Thr Tyr Lys Asn Leu
        130                 135                 140
Glu Lys Gly Lys Glu Val Glu Thr Leu Gly Trp Glu Asp Lys Gln Ala
145                 150                 155                 160
Ala Met Asp Ala Ile Glu His Ala Gln Asp Leu Tyr Ala Glu His Phe
                165                 170                 175
Gly

<210> SEQ ID NO 73
<211> LENGTH: 176
<212> TYPE: PRT
<213> ORGANISM: Natronococcus amylolyticus

<400> SEQUENCE: 73

Met Val Asn Leu Trp Glu Asp Leu Glu Thr Gly Pro Asn Pro Pro Glu
1               5                   10                  15
Glu Ile Tyr Ala Val Val Glu Cys Leu Lys Gly Glu Arg Asn Lys Tyr
                20                  25                  30
Glu Tyr Asp Lys Asp Val Pro Gly Val Val Leu Asp Arg Val Leu His
            35                  40                  45
Ser Asn Val His Tyr Pro Ser Asp Tyr Gly Phe Ile Pro Gln Ser Tyr
        50                  55                  60
Tyr Asp Glu Asp Pro Phe Asp Val Met Val Leu Val Glu Asp Gln
65                  70                  75                  80
Thr Phe Pro Gly Cys Ile Ile Glu Ala Arg Pro Val Ala Leu Met Lys
                85                  90                  95
Met Asp Asp Gly Glu Gln Asp Lys Val Ile Ala Val Pro Ser
            100                 105                 110
Glu Asp Pro Arg Tyr Asp His Ile Glu Asp Leu Glu Asp Ile Thr Gln
            115                 120                 125
Gln Gln Leu Asp Glu Ile Asp Glu Phe Phe Gln Thr Tyr Lys Asn Leu
        130                 135                 140
Glu Glu Gly Lys Glu Val Glu Thr Gln Gly Trp Glu Asp Arg Gln Ala
145                 150                 155                 160
Ala Tyr Asp Ala Ile Glu His Ala Gln Asp Leu Tyr Asp Glu Asn Phe
                165                 170                 175

<210> SEQ ID NO 74
<211> LENGTH: 177
<212> TYPE: PRT
<213> ORGANISM: Halosimplex carlsbadense

<400> SEQUENCE: 74

Met Ser Asn Leu Trp Gln Asp Leu Glu Thr Gly Pro Asn Pro Pro Glu
1               5                   10                  15
Glu Ile Tyr Ala Val Val Glu Cys Leu Lys Gly Glu Arg Asn Lys Tyr
                20                  25                  30
Glu Tyr Asp Lys Asp Ile Pro Gly Val Val Leu Asp Arg Val Leu His
            35                  40                  45
Ser Asn Val His Tyr Pro Ser Asp Tyr Gly Phe Ile Pro Gln Ser Tyr
        50                  55                  60
```

Tyr Asp Asp Glu Asp Pro Phe Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Gly Glu Gln Asp Lys Val Ile Ala Val Pro Ser
            100                 105                 110

Glu Asp Pro Arg Tyr Asp His Ile Glu Asp Leu Glu Asp Ile Thr Gln
            115                 120                 125

Gln Gln Leu Asp Glu Ile Asp Glu Phe Phe Ala Thr Tyr Lys Asn Leu
    130                 135                 140

Glu Glu Gly Lys Glu Val Glu Thr Leu Gly Trp Glu Lys Gln Ser
145                 150                 155                 160

Ala Tyr Asp Ala Ile Glu His Ala Gln Asp Leu Tyr Glu Gln Glu Phe
                165                 170                 175

Gln

<210> SEQ ID NO 75
<211> LENGTH: 176
<212> TYPE: PRT
<213> ORGANISM: Natronorubrum tibetense

<400> SEQUENCE: 75

Met Val Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Lys Val Ile Ala Val Pro Ser
            100                 105                 110

Glu Asp Pro Arg Tyr Asp His Ile Glu Asp Leu Glu Asp Ile Thr Gln
            115                 120                 125

Gln Gln Leu Asp Glu Ile Asp Glu Phe Phe Ser Ser Tyr Lys Asn Leu
    130                 135                 140

Glu Glu Gly Lys Gln Val Glu Thr Gln Gly Trp Glu Lys Gln Ala
145                 150                 155                 160

Ala Tyr Asp Ala Ile Glu His Ala Gln Glu Leu Tyr Glu Glu Asn Phe
                165                 170                 175

<210> SEQ ID NO 76
<211> LENGTH: 177
<212> TYPE: PRT
<213> ORGANISM: Halalkalicoccus jeotgali

<400> SEQUENCE: 76

Met Thr Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
                20                  25                  30

```
Glu Tyr Asp Lys Asp Val Pro Gly Val Val Leu Asp Arg Val Leu His
             35                  40                  45

Ser Asn Val His Tyr Pro Ser Asp Tyr Gly Phe Ile Pro Gln Ser Tyr
 50                  55                  60

Tyr Asp Asp Glu Asp Pro Phe Asp Val Leu Val Leu Val Glu Asp Gln
 65                  70                  75                  80

Thr Phe Pro Gly Cys Ile Val Glu Ala Arg Pro Val Ala Leu Met Lys
                 85                  90                  95

Met Asp Asp Gly Glu Gln Asp Lys Val Ile Ala Val Pro Val
                100                 105                 110

Glu Asp Pro Arg Tyr Asp His Ile Glu Asp Val Glu Asp Leu Thr Gln
            115                 120                 125

Gln Thr Lys Asp Glu Ile Asp Glu Phe Phe Ser Thr Tyr Lys Asn Leu
130                 135                 140

Glu Glu Gly Lys Glu Val Glu Thr Leu Gly Trp Glu Asp Arg Gln Thr
145                 150                 155                 160

Ala Tyr Asp Ala Ile Glu His Ser Gln Glu Leu Tyr Glu Glu Gln Phe
                165                 170                 175

Gly
```

<210> SEQ ID NO 77
<211> LENGTH: 177
<212> TYPE: PRT
<213> ORGANISM: Halococcus thailandensis

<400> SEQUENCE: 77

```
Met Thr Asn Leu Trp Glu Asp Leu Glu Thr Gly Pro Asn Ala Pro Glu
 1               5                  10                  15

Thr Ile His Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
             35                  40                  45

Ser Asn Val His Tyr Pro Asn Asp Tyr Gly Phe Ile Pro Gln Ser Tyr
 50                  55                  60

Tyr Asp Asp Glu Asp Pro Phe Asp Val Met Val Leu Val Glu Asp Ala
 65                  70                  75                  80

Thr Phe Pro Gly Cys Ile Ile Glu Ala Arg Pro Val Ala Leu Met Arg
                 85                  90                  95

Met Asp Asp Gly Glu Gln Asp Lys Val Ile Ala Val Pro Ala
                100                 105                 110

Glu Asp Pro Arg Phe Asp His Ile Glu Asp Leu Asp Ile Pro Gln
            115                 120                 125

Gln Glu Leu Asp Glu Ile Asp Glu Phe Phe Glu Thr Tyr Lys Asn Leu
130                 135                 140

Glu Ala Gly Lys Glu Val Glu Thr Gln Gly Trp Glu Asp Arg Gln Thr
145                 150                 155                 160

Ala Tyr Asp Ala Ile Glu His Ala Gln Asp Leu Tyr Asp Glu Gln Phe
                165                 170                 175

Ala
```

<210> SEQ ID NO 78
<211> LENGTH: 177
<212> TYPE: PRT
<213> ORGANISM: Halococcus salifodinae

<400> SEQUENCE: 78

```
Met Thr Asn Leu Trp Glu Asp Leu Glu Thr Gly Pro Asp Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
50                  55                  60

Tyr Asp Asp Glu Asp Pro Phe Asp Val Met Val Leu Val Glu Asp Gln
65                  70                  75                  80

Thr Phe Pro Gly Cys Ile Val Glu Ala Arg Pro Val Ala Leu Met Arg
            85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Glu Asp Ile Pro Gln
            115                 120                 125

Gln Gln Leu Asp Glu Ile Asp Glu Phe Phe Glu Thr Tyr Lys Asn Leu
            130                 135                 140

Glu Glu Gly Lys Glu Val Glu Thr Gln Gly Trp Glu Asp Arg Gln Ala
145                 150                 155                 160

Ala Tyr Asp Ala Ile Glu His Ala Gln Asp Leu Tyr Ala Glu Gln Phe
            165                 170                 175

Gly
```

<210> SEQ ID NO 79
<211> LENGTH: 177
<212> TYPE: PRT
<213> ORGANISM: Halorubrum aidingense

<400> SEQUENCE: 79

```
Met Val Asn Leu Trp Glu Asp Leu Glu Thr Gly Pro Asp Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Ala Val Val Leu Asp Arg Val Leu His
            35                  40                  45

Ser Asn Val His Tyr Pro Tyr Asp Tyr Gly Phe Ile Pro Gln Ser Tyr
50                  55                  60

Tyr Asp Asp Gly Asp Pro Phe Asp Val Met Val Leu Val Glu Asp Gln
65                  70                  75                  80

Thr Phe Pro Gly Cys Val Ile Glu Ala Arg Pro Val Ala Leu Met Lys
            85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Glu Asp Ile Pro Lys
            115                 120                 125

Gln Ile Arg Asp Glu Ile Asp Glu Phe Phe Ser Thr Tyr Lys Asn Leu
            130                 135                 140

Glu Ala Gly Lys Glu Val Glu Thr Leu Gly Trp Glu Asp Lys Glu Thr
145                 150                 155                 160

Ala Lys Glu Ala Ile Glu His Ala Gln Asp Leu Tyr Ala Glu Glu Phe
            165                 170                 175

Gln
```

<210> SEQ ID NO 80
<211> LENGTH: 177
<212> TYPE: PRT
<213> ORGANISM: Halococcus morrhuae

<400> SEQUENCE: 80

Met Thr Asn Leu Trp Glu Asp Leu Glu Thr Gly Pro Asn Ala Pro Glu
1               5                   10                  15

Thr Ile His Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Asn Asp Tyr Gly Phe Ile Pro Gln Ser Tyr
    50                  55                  60

Tyr Asp Asp Glu Asp Pro Phe Asp Val Met Val Leu Val Glu Asp Ala
65                  70                  75                  80

Thr Phe Pro Gly Cys Ile Ile Glu Ala Arg Pro Val Ala Leu Met Arg
                85                  90                  95

Met Asp Asp Asp Gly Glu Gln Asp Asp Lys Val Ile Ala Val Pro Ala
            100                 105                 110

Glu Asp Pro Arg Phe Asp His Ile Glu Asp Leu Gly Asp Ile Pro Gln
        115                 120                 125

Gln Glu Leu Asp Glu Ile Asp Glu Phe Phe Glu Thr Tyr Lys Asn Leu
    130                 135                 140

Glu Ala Gly Lys Glu Val Glu Thr Gln Gly Trp Glu Asp Arg Gln Ala
145                 150                 155                 160

Ala Tyr Asp Ala Ile Glu His Ala Gln Asp Leu Tyr Asp Glu Gln Phe
                165                 170                 175

Ala

<210> SEQ ID NO 81
<211> LENGTH: 177
<212> TYPE: PRT
<213> ORGANISM: Halococcus saccharolyticus

<400> SEQUENCE: 81

Met Thr Asn Leu Trp Glu Asp Leu Glu Thr Gly Pro Asp Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Glu Asp Ile Thr Gln
        115                 120                 125

Gln Gln Leu Asp Glu Ile Asp Glu Phe Phe Glu Thr Tyr Lys Asn Leu
    130                 135                 140

Glu Glu Gly Lys Glu Val Glu Thr Gln Gly Trp Glu Asp Arg Gln Ala

```
                145                 150                 155                 160
Ala Tyr Asp Ala Ile Glu His Ala Gln Asp Leu Tyr Ala Glu Gln Phe
                    165                 170                 175

Gly

<210> SEQ ID NO 82
<211> LENGTH: 177
<212> TYPE: PRT
<213> ORGANISM: Halobacterium sp.

<400> SEQUENCE: 82

Met Thr Asn Leu Trp Glu Asp Leu Glu Thr Gly Pro Asp Ala Pro Asp
1               5                   10                  15

Val Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Ile Pro Gln Ser Tyr
        50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Lys
                85                  90                  95

Met Asp Asp Asp Gly Glu Gln Asp Lys Val Ile Ala Val Pro Asp
                    100                 105                 110

Glu Asp Pro Arg Tyr Asp His Val Asn Asp Leu Ala Asp Ile Pro Gln
            115                 120                 125

Gln Thr Leu Asp Glu Ile Glu Glu Phe Phe Glu Thr Tyr Lys Asn Leu
        130                 135                 140

Glu Ala Gly Lys Glu Val Glu Thr Gln Gly Phe Glu Asp Ala Ala Ala
145                 150                 155                 160

Ala Lys Asp Ala Ile Glu His Ala Gln Asp Leu Tyr Ser Glu His Phe
                    165                 170                 175

Glu

<210> SEQ ID NO 83
<211> LENGTH: 177
<212> TYPE: PRT
<213> ORGANISM: Halogeometricum borinquense

<400> SEQUENCE: 83

Met Thr Asn Leu Trp Glu Asp Met Glu Thr Gly Pro Asp Ala Pro Asp
1               5                   10                  15

Val Val Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Met Pro Gln Thr Tyr
        50                  55                  60

Tyr Asp Asp Glu Asp Pro Phe Asp Ile Leu Val Leu Val Glu Asp Gln
65                  70                  75                  80

Thr Phe Pro Gly Cys Val Ile Glu Ala Arg Pro Val Ala Leu Met Gly
                85                  90                  95

Met Asp Asp Asp Gly Glu Lys Asp Lys Val Ile Ala Val Pro Thr
                    100                 105                 110
```

-continued

Glu Asp Pro Arg Tyr Asp His Val Gln Asp Val Asp Leu Thr Asp
            115                 120                 125

Gln Gln Lys Asp Glu Ile Ala Glu Phe Phe Glu Thr Tyr Lys Asn Leu
130                 135                 140

Glu Ala Gly Lys Glu Val Glu Thr Leu Gly Trp Glu Gly Ala Asp Ala
145                 150                 155                 160

Ala Lys Asp Ala Ile Glu His Ala Met Asp Leu Tyr Asp Glu Asn Phe
                165                 170                 175

Ala

<210> SEQ ID NO 84
<211> LENGTH: 178
<212> TYPE: PRT
<213> ORGANISM: uncultured archaeon

<400> SEQUENCE: 84

Met Val Asn Leu Trp Ala Asp Leu Glu Thr Gly Pro Asp Ala Pro Asp
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Ile Val Leu Asp Arg Val Leu His
            35                  40                  45

Ser Asn Val His Tyr Pro Tyr Asp Tyr Gly Phe Ile Pro Arg Ser Tyr
    50                  55                  60

Tyr Asp Asp Gly Asp Pro Phe Asp Val Met Val Leu Val Glu Asp Ala
65                  70                  75                  80

Thr Phe Pro Gly Cys Val Val Glu Ala Arg Pro Val Ala Leu Met Arg
                85                  90                  95

Met Asp Asp Asp Gly Glu Gln Asp Asp Lys Val Ile Ala Val Pro Thr
            100                 105                 110

Glu Asp Pro Arg Phe Asp His Ile Glu Asp Leu Glu Asp Ile Pro Gln
        115                 120                 125

Gln Ile Arg Asp Glu Ile Asp Glu Phe Phe Ala Thr Tyr Lys Asn Leu
130                 135                 140

Glu Ala Gly Lys Glu Val Glu Thr Leu Gly Trp Glu Asp Lys Thr Ala
145                 150                 155                 160

Ala Lys Glu Ala Val Glu His Ala Gln Glu Leu Tyr Asp Glu Glu Phe
                165                 170                 175

Gly Ala

<210> SEQ ID NO 85
<211> LENGTH: 176
<212> TYPE: PRT
<213> ORGANISM: Halorubrum sp

<400> SEQUENCE: 85

Met Val Asp Leu Trp Gln Glu Leu Glu Thr Gly Pro Asn Pro Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Ile Pro Gly Val Val Leu Asp Arg Val Leu His
            35                  40                  45

Ser Asn Val His Tyr Pro Ser Asp Tyr Gly Phe Ile Pro Gln Ser Tyr
    50                  55                  60

Tyr Asp Asp Glu Asp Pro Phe Asp Val Leu Val Leu Val Glu Asp Gln
65                  70                  75                  80

```
Thr Phe Pro Gly Cys Val Val Glu Ala Arg Pro Ile Ala Leu Met Lys
                85                  90                  95
Met Asp Asp Asp Gly Glu Gln Asp Lys Val Ile Ala Val Pro Thr
               100                 105                 110
Glu Asp Pro Arg Phe Asp His Met Gln Asp Leu Asp Asp Ile Pro Gln
            115                 120                 125
Gln Gln Leu Asp Glu Ile Asp Glu Phe Phe Ala Thr Tyr Lys Asn Leu
        130                 135                 140
Glu Glu Gly Lys Glu Val Ala Thr Leu Gly Phe Gly Asp Arg Ser Ala
145                 150                 155                 160
Ala His Asp Ala Ile Glu His Ala Gln Gln Leu Tyr Glu Asp Glu Phe
                165                 170                 175
```

<210> SEQ ID NO 86
<211> LENGTH: 176
<212> TYPE: PRT
<213> ORGANISM: uncultured archaeon

<400> SEQUENCE: 86

```
Met Val Asp Leu Trp Gln Glu Leu Glu Thr Gly Pro Asn Pro Pro Glu
1               5                   10                  15
Glu Ile Tyr Ala Val Val Glu Cys Leu Lys Gly Glu Arg Asn Lys Tyr
            20                  25                  30
Glu Tyr Asp Lys Asp Ile Pro Gly Val Val Leu Asp Arg Val Leu His
        35                  40                  45
Ser Asn Val His Tyr Pro Ser Asp Tyr Gly Phe Ile Pro Gln Ser Tyr
50                  55                  60
Tyr Asp Asp Glu Asp Pro Phe Asp Val Leu Val Leu Val Glu Asp Gln
65                  70                  75                  80
Thr Phe Pro Gly Cys Val Val Glu Ala Arg Pro Ile Ala Leu Met Lys
                85                  90                  95
Met Asp Asp Asp Gly Glu Gln Asp Lys Val Ile Ala Val Pro Thr
               100                 105                 110
Glu Asp Pro Arg Phe Asp His Met Gln Asp Leu Asp Asp Ile Pro Gln
            115                 120                 125
Gln Gln Leu Asp Glu Ile Asp Glu Phe Phe Ala Thr Tyr Lys Asn Leu
        130                 135                 140
Glu Glu Gly Lys Glu Val Ala Thr Leu Gly Phe Gly Asp Arg Ser Ala
145                 150                 155                 160
Ala His Asp Ala Ile Glu His Ala Gln Gln Leu Tyr Glu Asp Glu Phe
                165                 170                 175
```

<210> SEQ ID NO 87
<211> LENGTH: 177
<212> TYPE: PRT
<213> ORGANISM: halophilic archaeon

<400> SEQUENCE: 87

```
Met Thr Asn Leu Trp Glu Asp Leu Glu Thr Gly Pro Asn Ala Pro Glu
1               5                   10                  15
Glu Ile Tyr Ala Val Val Glu Cys Leu Lys Gly Glu Arg Asn Lys Tyr
            20                  25                  30
Glu Tyr Glu Lys Asp Ile Pro Gly Val Val Leu Asp Arg Val Leu His
        35                  40                  45
Ser Asn Val His Tyr Pro Ser Asp Tyr Gly Phe Ile Pro Gln Ser Tyr
50                  55                  60
```

Tyr Asp Asp Glu Asp Pro Phe Asp Val Leu Val Leu Val Glu Asp Ala
65                  70                  75                  80

Thr Phe Pro Gly Cys Val Ile Glu Ala Arg Pro Val Ala Leu Met Arg
                85                  90                  95

Met Asp Asp Gly Glu Lys Asp Lys Val Ile Ala Val Pro Ser
            100                 105                 110

Glu Asp Pro Arg Tyr Asp His Ile Gln Asp Leu Glu Asp Ile Pro Gln
            115                 120                 125

Gln Gln Val Asp Glu Ile Asp Glu Phe Phe Ser Thr Tyr Lys Asn Leu
        130                 135                 140

Glu Glu Gly Lys Glu Val Thr Thr Leu Gly Trp Glu Asp Lys Ala Ser
145                 150                 155                 160

Ala His Glu Ala Ile Glu His Ala Gln Glu Leu Phe Asp Glu Phe
                165                 170                 175

Asn

<210> SEQ ID NO 88
<211> LENGTH: 177
<212> TYPE: PRT
<213> ORGANISM: Halogeometricum pallidum

<400> SEQUENCE: 88

Met Thr Asn Leu Trp Glu Asp Ile Glu Thr Gly Pro Asp Ala Pro Asp
1               5                   10                  15

Val Val Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Gln Thr Tyr
    50                  55                  60

Tyr Asp Asp Glu Asp Pro Phe Asp Val Leu Val Leu Val Glu Asp Gln
65                  70                  75                  80

Thr Phe Pro Gly Cys Ile Ile Glu Ala Arg Pro Val Ala Leu Met Gly
                85                  90                  95

Met Asp Asp Asp Gly Glu Lys Asp Lys Val Ile Ala Val Pro Thr
            100                 105                 110

Glu Asp Pro Arg Tyr Asp Asp Val Gln Asp Leu Asp Asp Leu Ser Glu
            115                 120                 125

Gln Gln Lys Arg Glu Ile Ala Glu Phe Phe Glu Thr Tyr Lys Asn Leu
        130                 135                 140

Glu Lys Gly Lys Glu Val Glu Thr Leu Gly Trp Glu Asp Ala Asp Ala
145                 150                 155                 160

Ala Lys Asp Ala Ile Glu His Ala Met Asp Leu Tyr Glu Glu Asn Phe
                165                 170                 175

Ala

<210> SEQ ID NO 89
<211> LENGTH: 178
<212> TYPE: PRT
<213> ORGANISM: Halorhabdus utahensis

<400> SEQUENCE: 89

Met Val Asn Leu Phe Glu Ala Leu Glu Ala Gly Pro Asn Pro Pro Glu
1               5                   10                  15

Glu Ile Tyr Ala Val Val Glu Cys Leu Lys Gly Glu Arg Asn Lys Tyr

```
            20                  25                  30
Glu Tyr Asp Lys Asp Leu Pro Gly Val Val Leu Asp Arg Val Leu His
            35                  40                  45

Ser Asn Val His Tyr Pro Ser Asp Tyr Gly Phe Ile Pro Gln Ser His
    50                  55                  60

Tyr Asp Asp Asp Pro Leu Asp Val Leu Val Leu Val Glu Asp Gln
65                  70                  75                  80

Thr Phe Pro Gly Cys Val Ile Glu Ala Arg Pro Val Ala Leu Met Lys
                85                  90                  95

Met Asp Asp Gly Glu Gln Asp Asp Lys Val Ile Ala Val Pro Thr
            100                 105                 110

Glu Asp Pro Arg Tyr Asp His Ile Glu Asp Leu Glu Asp Ile Pro Ser
            115                 120                 125

Gln Gln Leu Asp Glu Ile Asp Glu Phe Phe Glu Thr Tyr Lys Asn Leu
            130                 135                 140

Glu Glu Gly Lys Glu Val Glu Thr Leu Gly Trp Glu Asp Ala Ala Ala
145                 150                 155                 160

Ala Arg Asp Ala Ile Glu His Ser Arg Glu Leu Tyr Glu Glu Lys Ile
                165                 170                 175

Ala Glu

<210> SEQ ID NO 90
<211> LENGTH: 177
<212> TYPE: PRT
<213> ORGANISM: Halococcus hamelinensis

<400> SEQUENCE: 90

Met Val Asn Leu Trp Thr Asp Leu Glu Thr Gly Pro Asp Ala Pro Glu
1               5                   10                  15

Thr Ile His Ala Val Val Glu Cys Leu Lys Gly Asp Arg Asn Lys Tyr
            20                  25                  30

Glu Tyr Asp Lys Asp Ile Pro Gly Met Val Leu Asp Arg Val Leu His
            35                  40                  45

Ser Asn Val His Tyr Pro His Asp Tyr Gly Phe Ile Pro Gln Cys Tyr
    50                  55                  60

Tyr Asp Asp Gly Asp Pro Phe Asp Val Leu Val Leu Val Glu Asp Gly
65                  70                  75                  80

Thr Phe Pro Gly Cys Val Ile Glu Val Arg Pro Val Ala Leu Met Gly
                85                  90                  95

Met Asp Asp Asp Gly Glu Gln Asp Asp Lys Val Ile Ala Val Pro Val
            100                 105                 110

Glu Asp Pro Arg Phe Asp His Ile Glu Asp Leu Glu Asp Ile Pro Gln
            115                 120                 125

Gln Glu Arg Asp Glu Ile Thr Glu Phe Phe Glu Thr Tyr Lys Asn Leu
            130                 135                 140

Glu Ala Gly Lys Glu Val Glu Thr Leu Gly Trp Glu Asp Lys Gln Ala
145                 150                 155                 160

Ala His Asp Ala Ile Glu His Ala Gln Glu Leu Tyr Glu Glu Gln Phe
                165                 170                 175

Gly

<210> SEQ ID NO 91
<211> LENGTH: 178
<212> TYPE: PRT
<213> ORGANISM: Halorhabdus tiamatea
```

<400> SEQUENCE: 91

Met Val Asn Leu Phe Glu Ala Leu Glu Ala Gly Pro Asn Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Leu Pro Gly Val Val Leu Asp Arg Val Leu His
                35                  40                  45

Ser Asn Val His Tyr Pro Ser Asp Tyr Gly Phe Ile Pro Gln Ser His
        50                  55                  60

Tyr Asp Asp Asp Pro Leu Asp Val Leu Val Leu Glu Asp Gln
65                  70                  75                  80

Thr Phe Pro Gly Cys Val Val Glu Ala Arg Pro Val Ala Leu Met Lys
                85                  90                  95

Met Asp Asp Asp Gly Glu Ala Asp Asp Lys Val Ile Ala Val Pro Thr
                100                 105                 110

Glu Asp Pro Arg Tyr Asp His Ile Glu Asp Leu Glu Asp Ile Pro Ser
            115                 120                 125

Gln Gln Arg Asp Glu Ile Asp Glu Phe Phe Ala Thr Tyr Lys Asn Leu
        130                 135                 140

Glu Glu Gly Lys Glu Val Glu Thr Leu Gly Trp Asp Ala Ala Ala
145                 150                 155                 160

Ala Lys Glu Ala Ile Glu His Ser Gln Asp Leu Tyr Glu Glu Lys Ile
                165                 170                 175

Ala Lys

<210> SEQ ID NO 92
<211> LENGTH: 181
<212> TYPE: PRT
<213> ORGANISM: Salinarchaeum sp

<400> SEQUENCE: 92

Met Val Asn Leu Trp Glu Asp Leu Glu Thr Gly Pro Asn Pro Glu
1               5                   10                  15

Glu Ile Tyr Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
                35                  40                  45

Ser Asn Val His Tyr Pro Ser Asp Tyr Gly Phe Leu Pro Arg Ser Tyr
        50                  55                  60

Tyr Asp Asp Glu Asp Pro Phe Asp Val Leu Val Leu Glu Asp Gln
65                  70                  75                  80

Thr Phe Pro Gly Cys Val Ile Glu Ala Arg Pro Val Ala Leu Met Gly
                85                  90                  95

Met Asp Asp Asp Gly Glu Gln Asp Asp Lys Val Ile Ala Val Pro Thr
                100                 105                 110

Glu Asp Pro Arg Tyr Asp His Val Gln Asp Val Glu Asp Leu Thr Asp
            115                 120                 125

Gln Gln Lys Ala Glu Ile Ala Glu Phe Phe Glu Thr Tyr Lys Asn Leu
        130                 135                 140

Glu Glu Gly Lys Glu Val Glu Thr Leu Gly Trp Asp Ala Asp Ala
145                 150                 155                 160

Ala Lys Asp Ala Ile Glu His Ser Met Glu Leu Tyr Asp Glu His Phe
                165                 170                 175

Asp Ser Pro Arg Asn
            180

<210> SEQ ID NO 93
<211> LENGTH: 177
<212> TYPE: PRT
<213> ORGANISM: Candidatus Halobonum tyrrellensis

<400> SEQUENCE: 93

Met Thr Asn Leu Trp Glu Asp Leu Glu Thr Gly Pro Asp Ala Pro Asp
1               5                   10                  15

Glu Ile Tyr Ala Val Val Glu Cys Leu Lys Gly Glu Arg Asn Lys Tyr
            20                  25                  30

Glu Tyr Asp Lys Asp Ile Pro Gly Val Val Leu Asp Arg Val Leu His
        35                  40                  45

Ser Asn Val His Tyr Pro Ser Asp Tyr Gly Phe Met Pro Arg Thr Tyr
    50                  55                  60

Tyr Asp Asp Gly Asp Pro Phe Asp Val Leu Val Leu Val Lys Asp Gln
65                  70                  75                  80

Thr Phe Pro Gly Cys Ile Val Glu Ala Arg Pro Val Ala Met Met Lys
                85                  90                  95

Met Asp Asp Asp Gly Glu Gln Asp Asp Lys Val Val Ala Val Pro Val
            100                 105                 110

Glu Asp Pro Arg Tyr Asp His Val His Asp Val Gly Asp Leu Thr Asp
        115                 120                 125

Gln Thr Lys Ala Glu Ile Glu Glu Phe Phe Glu Thr Tyr Lys Asn Leu
    130                 135                 140

Glu Glu Gly Lys Glu Val Ala Thr Glu Gly Trp Glu Asp Ala Gln Ser
145                 150                 155                 160

Ala Lys Asp Ala Ile Glu His Ala Gln Gln Leu Tyr Asp Glu Glu Phe
                165                 170                 175

Ala

<210> SEQ ID NO 94
<211> LENGTH: 177
<212> TYPE: PRT
<213> ORGANISM: Haloquadratum walsbyi

<400> SEQUENCE: 94

Met Ser Asn Leu Trp Thr Asp Leu Glu Thr Gly Pro Asp Ala Pro Asp
1               5                   10                  15

Val Val Tyr Ala Val Ile Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Leu Pro Gln Thr Tyr
    50                  55                  60

Tyr Asp Asp Glu Asp Pro Phe Asp Ile Met Val Leu Val Glu Asp Gln
65                  70                  75                  80

Thr Phe Pro Gly Cys Ile Ile Glu Ala Arg Pro Val Ala Leu Met Arg
                85                  90                  95

Met Asp Asp Asp Gly Glu Lys Asp Lys Val Ile Ala Val Pro Asp
            100                 105                 110

Glu Asp Pro Arg Tyr Asp His Val Glu Asp Leu Asp Asp Leu Thr Asp
        115                 120                 125

Gln Thr Thr Ala Glu Ile Ala Glu Phe Phe Glu Thr Tyr Lys Asn Leu

```
                130               135               140
Glu Ala Gly Lys Gln Thr Glu Thr Leu Gly Trp Glu Gly Val Asp Ala
145               150               155               160

Ala Arg Asp Ala Ile Glu His Ala Met Asp Leu Tyr Glu Lys Gln Ile
                165               170               175

Asn

<210> SEQ ID NO 95
<211> LENGTH: 176
<212> TYPE: PRT
<213> ORGANISM: halophilic archaeon

<400> SEQUENCE: 95

Met Met Thr Asn Leu Trp Glu Asp Leu Glu Thr Gly Pro Asp Pro Pro
1               5                   10                  15

Glu Glu Ile Tyr Ala Val Val Glu Cys Leu Lys Gly Glu Arg Asn Lys
                20                  25                  30

Tyr Glu Tyr Glu Lys Glu Ile Pro Gly Met Val Leu Asp Arg Val Leu
            35                  40                  45

His Ser Asn Val His Tyr Pro Ser Asp Tyr Gly Phe Ile Pro Gln Ser
        50                  55                  60

Tyr Tyr Asp Asp Gly Asp Pro Phe Asp Val Leu Val Leu Val Glu Asp
65                  70                  75                  80

Gln Thr Phe Pro Gly Cys Val Ile Glu Ala Arg Pro Val Ala Leu Met
                85                  90                  95

Gly Met Asp Asp Asp Gly Glu Lys Asp Lys Val Ile Ala Val Pro
                100                 105                 110

Ala Glu Asp Pro Arg Tyr Asp His Ile Thr Asp Leu Ala Asp Ile Pro
            115                 120                 125

Gln Gln Thr Leu Asp Glu Ile Ala Glu Phe Phe Glu Thr Tyr Lys Asn
130                 135                 140

Leu Glu Ser Gly Lys Glu Thr Glu Thr Leu Gly Phe Glu Asp Arg Gln
145                 150                 155                 160

Ala Ala Phe Asp Ala Ile Glu His Ala Gln Arg Leu Tyr Glu Glu Arg
                165                 170                 175

<210> SEQ ID NO 96
<211> LENGTH: 177
<212> TYPE: PRT
<213> ORGANISM: Halanaeroarchaeum sulfurireducens

<400> SEQUENCE: 96

Met Thr Asn Leu Trp Ala Asp Leu Glu Thr Gly Pro Asp Ala Pro Glu
1               5                   10                  15

Thr Ile Tyr Ala Val Ile Glu Cys Leu Lys Gly Glu Arg Asn Lys Tyr
                20                  25                  30

Glu Tyr Asp Lys Asp Val Pro Ala Val Val Leu Asp Arg Val Leu His
            35                  40                  45

Ser Asn Val His Tyr Pro Tyr Asp Tyr Gly Phe Ile Pro Gln Ser Tyr
        50                  55                  60

Tyr Asp Asp Asp Pro Phe Asp Val Met Val Leu Val Glu Asp Gln
65                  70                  75                  80

Thr Phe Pro Gly Cys Ile Ile Glu Ala Arg Pro Ile Ala Leu Met Arg
                85                  90                  95

Met Asp Asp Asp Gly Glu Lys Asp Lys Val Ile Ala Val Pro Lys
                100                 105                 110
```

Glu Asp Pro Arg Phe Asp His Met Glu Asp Leu Asp Ile Ser Glu
            115                 120                 125

Gln Thr Lys Ala Glu Ile Ala Glu Phe Phe Glu Thr Tyr Lys Asn Leu
        130                 135                 140

Glu Glu Gly Lys Gln Thr Glu Thr Leu Gly Trp Glu Asp Lys Gln Ala
145                 150                 155                 160

Ala Leu Asp Ala Ile Glu His Ala Gln Asp Leu Tyr Asp Glu Gln Phe
                165                 170                 175

Ala

<210> SEQ ID NO 97
<211> LENGTH: 177
<212> TYPE: PRT
<213> ORGANISM: Haloquadratum walsbyi

<400> SEQUENCE: 97

Met Ser Asn Leu Trp Thr Asp Leu Glu Thr Gly Pro Asp Ala Pro Asp
1               5                   10                  15

Val Val Tyr Ala Val Ile Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Leu Pro Gln Thr Tyr
        50                  55                  60

Tyr Asp Asp Glu Asp Pro Phe Asp Ile Met Val Leu Val Glu Asp Gln
65                  70                  75                  80

Thr Phe Pro Gly Cys Ile Ile Glu Ala Arg Pro Val Ala Leu Met Arg
                85                  90                  95

Met Asp Asp Asp Gly Glu Lys Asp Lys Val Ile Ala Val Pro Asp
            100                 105                 110

Glu Asp Pro Arg Tyr Asp His Val Glu Asp Leu Asp Asp Leu Thr Asp
        115                 120                 125

Gln Thr Thr Ala Glu Ile Ala Glu Phe Phe Glu Thr Tyr Lys Asn Leu
    130                 135                 140

Glu Thr Gly Lys Gln Thr Glu Thr Leu Gly Trp Glu Ser Ala Asp Ala
145                 150                 155                 160

Ala Thr Asp Ala Ile Glu His Ala Met Glu Leu Tyr Glu Glu Gln Ile
                165                 170                 175

Asp

<210> SEQ ID NO 98
<211> LENGTH: 177
<212> TYPE: PRT
<213> ORGANISM: Haloquadratum walsbyi

<400> SEQUENCE: 98

Met Ser Asn Leu Trp Thr Asp Leu Glu Thr Gly Pro Asp Ala Pro Asp
1               5                   10                  15

Val Val Tyr Ala Val Ile Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ser Asn Val His Tyr Pro Ser Asp Tyr Gly Phe Leu Pro Gln Thr Tyr
        50                  55                  60

Tyr Asp Asp Glu Asp Pro Phe Asp Ile Met Val Leu Val Glu Asp Gln

```
              65                  70                  75                  80
         Thr Phe Pro Gly Cys Ile Ile Glu Ala Arg Pro Val Ala Leu Met Arg
                          85                  90                  95
         Met Asp Asp Asp Gly Glu Lys Asp Asp Lys Val Ile Ala Val Pro Asp
                         100                 105                 110
         Glu Asp Pro Arg Tyr Asp His Val Glu Asp Leu Asp Leu Thr Asp
                         115                 120                 125
         Gln Thr Thr Ala Glu Ile Ala Glu Phe Phe Glu Thr Tyr Lys Asn Leu
                 130                 135                 140
         Glu Thr Gly Lys Gln Thr Glu Thr Leu Gly Trp Gly Gly Ala Asp Ala
         145                 150                 155                 160
         Ala Thr Asp Ala Ile Glu His Ala Met Glu Leu Tyr Glu Glu Gln Ile
                         165                 170                 175
         Asp

<210> SEQ ID NO 99
<211> LENGTH: 177
<212> TYPE: PRT
<213> ORGANISM: Halobacterium salinarum

<400> SEQUENCE: 99

Met Ala Asn Leu Trp Glu Asp Leu Glu Thr Gly Pro Asp Ala Pro Asp
         1                5                  10                  15
         Val Ile Tyr Ala Val Val Glu Cys Leu Lys Gly Glu Arg Asn Lys Tyr
                          20                  25                  30
         Glu Tyr Asp Lys Asp Ile Pro Gly Val Val Leu Asp Arg Val Leu His
                          35                  40                  45
         Ser Asn Val His Tyr Pro Ser Asp Tyr Gly Phe Ile Pro Gln Ser Tyr
                 50                  55                  60
         Tyr Asp Asp Gly Asp Pro Phe Asp Val Leu Val Leu Val Glu Asp Gln
         65                  70                  75                  80
         Thr Phe Pro Gly Cys Val Ile Glu Ala Arg Pro Val Ala Leu Met Glu
                          85                  90                  95
         Met Asp Asp Asp Gly Glu Gln Asp Asp Lys Val Ile Ala Val Pro Glu
                         100                 105                 110
         Glu Asp Pro Arg Tyr Asp Asp Val Glu Asp Val Asp Leu Thr Asp
                         115                 120                 125
         Gln Gln Lys Ala Glu Ile Ala Glu Phe Phe Glu Thr Tyr Lys Asn Leu
                 130                 135                 140
         Glu Ala Asp Lys Glu Thr Ala Val Leu Gly Trp Gly Asp Ala Gln Ala
         145                 150                 155                 160
         Ala Lys Asp Ala Ile Glu His Ala Gln Asp Leu Tyr Asp Glu Gln Phe
                         165                 170                 175
         Ala

<210> SEQ ID NO 100
<211> LENGTH: 177
<212> TYPE: PRT
<213> ORGANISM: Halobacterium salinarum

<400> SEQUENCE: 100

Met Ala Asn Leu Trp Glu Asp Leu Glu Thr Gly Pro Asp Ala Pro Asp
         1                5                  10                  15
         Val Ile Tyr Ala Val Val Glu Cys Leu Lys Gly Glu Arg Asn Lys Tyr
                          20                  25                  30
```

-continued

Glu Tyr Asp Lys Asp Ile Pro Gly Val Val Leu Asp Arg Val Leu His
        35                  40                  45

Ser Asn Val His Tyr Pro Ser Asp Tyr Gly Phe Ile Pro Gln Ser Tyr
 50                  55                  60

Tyr Asp Asp Gly Asp Pro Phe Asp Val Leu Val Leu Val Glu Asp Gln
 65                  70                  75                  80

Thr Phe Pro Gly Cys Val Ile Glu Ala Arg Pro Val Ala Leu Met Glu
                 85                  90                  95

Met Asp Asp Gly Glu Gln Asp Lys Val Ile Ala Val Pro Glu
                100                 105                 110

Glu Asp Pro Arg Tyr Asp Asp Val Glu Asp Val Asp Leu Thr Asp
            115                 120                 125

Gln Gln Lys Ala Glu Ile Ala Glu Phe Phe Glu Thr Tyr Lys Asn Leu
    130                 135                 140

Glu Ala Asp Lys Glu Thr Ala Val Leu Gly Trp Gly Asp Ala Gln Ala
145                 150                 155                 160

Ala Lys Asp Ala Ile Glu His Ala Gln Asp Leu Tyr Asp Glu Gln Phe
                165                 170                 175

Ala

<210> SEQ ID NO 101
<211> LENGTH: 177
<212> TYPE: PRT
<213> ORGANISM: Haloquadratum walsbyi

<400> SEQUENCE: 101

Met Ser Asn Leu Trp Thr Asp Leu Glu Thr Gly Pro Asp Ala Pro Asn
 1               5                  10                  15

Val Val His Ala Val Val Glu Cys Leu Lys Gly Glu Arg Asn Lys Tyr
                 20                  25                  30

Glu Tyr Asp Lys Asp Val Pro Gly Val Val Leu Asp Arg Val Leu His
        35                  40                  45

Ser Asn Val His Tyr Pro Ser Asp Tyr Gly Phe Leu Pro Gln Thr Tyr
 50                  55                  60

Tyr Asp Asp Asn Asp Pro Phe Asp Ile Met Val Leu Val Glu Asp Gln
 65                  70                  75                  80

Thr Phe Pro Gly Cys Val Ile Glu Ala Arg Pro Val Ala Leu Met Arg
                 85                  90                  95

Met Asp Asp Asp Gly Glu Lys Asp Asp Lys Val Ile Ala Val Pro Thr
                100                 105                 110

Glu Asp Pro Arg Tyr Asp His Val Glu Asp Leu Asp Asp Leu Thr Asp
            115                 120                 125

Gln Thr Thr Ala Glu Ile Ala Glu Phe Phe Glu Thr Tyr Lys Asn Leu
    130                 135                 140

Glu Ser Asn Lys Gln Thr Glu Thr Leu Gly Trp Glu Asp Ala Asp Ala
145                 150                 155                 160

Ala Lys Asn Ala Ile Glu His Ala Met Glu Leu Tyr Glu Glu Gln Val
                165                 170                 175

Ile

<210> SEQ ID NO 102
<211> LENGTH: 177
<212> TYPE: PRT
<213> ORGANISM: Haloquadratum sp.

<400> SEQUENCE: 102

Met Thr Asn Leu Trp Thr Glu Leu Glu Thr Gly Pro Asn Pro Asp
1               5                   10                  15

Val Val Asn Ala Val Val Glu Cys Leu Lys Gly Glu Arg Asn Lys Tyr
                20                  25                  30

Glu Tyr Asp Lys Asp Val Pro Gly Val Val Leu Asp Arg Val Leu His
            35                  40                  45

Ala Asn Val His Tyr Pro Ser Asp Tyr Gly Phe Leu Pro Arg Thr Tyr
50                      55                      60

Tyr Asp Asp Glu Asp Pro Phe Asp Ile Leu Val Leu Val Glu Asp Gln
65                      70                      75                  80

Thr Phe Pro Gly Cys Ile Val Glu Thr Arg Pro Val Ala Leu Met Glu
                85                  90                  95

Met Asp Asp Asp Gly Glu Lys Asp Lys Val Ile Gly Val Pro Val
                100                 105                 110

Glu Asp Pro Arg Tyr Asp His Val Arg Asp Val Ser Asp Leu Thr Glu
            115                 120                 125

Gln Thr Arg Ala Glu Ile Ala Glu Phe Phe Glu Thr Tyr Lys Asn Leu
        130                 135                 140

Glu Ala Gly Lys Gln Thr Glu Thr Leu Gly Trp Ser Asp Ala Gln Ala
145                 150                 155                 160

Ala Lys Asp Ala Ile Glu His Ala Met Asn Leu Tyr Ser Asp Thr Phe
                165                 170                 175

Glu

<210> SEQ ID NO 103
<211> LENGTH: 176
<212> TYPE: PRT
<213> ORGANISM: Halonotius sp

<400> SEQUENCE: 103

Met Thr Asn Leu Trp Lys Asp Ile Glu Ala Gly Pro Asp Ala Pro Glu
1               5                   10                  15

Thr Ile His Ala Val Val Glu Cys Leu Lys Gly Glu Arg Asn Lys Tyr
                20                  25                  30

Glu Tyr Asp Lys Asp Ile Pro Ala Val Val Leu Asp Arg Val Leu His
            35                  40                  45

Ser Asn Val His Tyr Pro Ser Asp Tyr Gly Phe Ile Pro Arg Thr Trp
50                      55                      60

Tyr Asp Asp Asp Pro Leu Asp Val Leu Val Leu Val Glu Asp Gln
65                      70                      75                  80

Thr Phe Pro Gly Cys Val Ile Glu Ala Arg Pro Val Ala Leu Met Gly
                85                  90                  95

Met Asp Asp Gly Gly Glu Lys Asp Lys Ile Ile Ala Val Pro Ala
                100                 105                 110

Glu Asp Pro Arg Tyr Asp His Ile Asp Leu Asp Asp Ile Thr Glu
            115                 120                 125

Gln Thr Lys Ala Glu Ile Gly Glu Phe Phe Asp Thr Tyr Lys Asn Leu
        130                 135                 140

Glu Glu Gly Lys Ala Ala Glu Thr Leu Gly Trp Glu Asp Lys Gln Ala
145                 150                 155                 160

Ala Leu Asp Ala Ile Glu His Ser Gln Asp Leu Tyr Asp Glu Lys Phe
                165                 170                 175

<210> SEQ ID NO 104

```
<211> LENGTH: 176
<212> TYPE: PRT
<213> ORGANISM: uncultured archaeon

<400> SEQUENCE: 104

Met Thr Asn Leu Trp Lys Asp Ile Glu Ala Gly Pro Asp Ala Pro Glu
1               5                   10                  15

Thr Ile His Ala Val Val Glu Cys Leu Lys Gly Glu Arg Asn Lys Tyr
            20                  25                  30

Glu Tyr Asp Lys Asp Ile Pro Ala Val Val Leu Asp Arg Val Leu His
        35                  40                  45

Ser Asn Val His Tyr Pro Ser Asp Tyr Gly Phe Ile Pro Arg Thr Trp
    50                  55                  60

Tyr Asp Asp Asp Pro Leu Asp Val Leu Val Leu Val Glu Asp Gln
65                  70                  75                  80

Thr Phe Pro Gly Cys Val Ile Glu Ala Arg Pro Val Ala Leu Met Gly
                85                  90                  95

Met Asp Asp Gly Gly Glu Lys Asp Lys Val Ile Ala Val Pro Asp
            100                 105                 110

Glu Asp Pro Arg Tyr Asp His Ile Asp Asp Leu Asp Asp Ile Thr Glu
        115                 120                 125

Gln Thr Lys Ala Glu Ile Gly Glu Phe Phe Asp Thr Tyr Lys Asn Leu
    130                 135                 140

Glu Glu Gly Lys Ala Ala Glu Thr Leu Gly Trp Glu Lys Gln Ala
145                 150                 155                 160

Ala Leu Asp Ala Ile Glu His Ser Gln Asp Leu Tyr Asp Glu Lys Phe
                165                 170                 175

<210> SEQ ID NO 105
<211> LENGTH: 247
<212> TYPE: PRT
<213> ORGANISM: Halarchaeum acidiphilum

<400> SEQUENCE: 105

Met Val Asn Leu Trp Glu Asp Leu Glu Thr Gly Pro Asp Ala Pro Asp
1               5                   10                  15

Thr Val Tyr Ala Val Val Glu Cys Leu Lys Gly Glu Arg Asn Lys Tyr
            20                  25                  30

Glu Tyr Asp Lys Asp Ile Pro Gly Thr Val Leu Asp Arg Val Leu His
        35                  40                  45

Ser Asn Val His Tyr Pro Ser Asp Tyr Gly Phe Met Pro Gln Thr Tyr
    50                  55                  60

Tyr Asp Asp Gly Asp Pro Phe Asp Val Leu Val Leu Val Lys Asp Gln
65                  70                  75                  80

Thr Phe Pro Glu Cys Val Ile Glu Ala Arg Pro Val Ala Leu Met Arg
                85                  90                  95

Met Asp Asp Asp Gly Glu Gln Asp Lys Val Ile Ala Val Pro Glu
            100                 105                 110

Glu Asp Pro Arg Tyr Asp His Ile Glu Asp Val Asp Asp Leu Thr Glu
        115                 120                 125

Gln Lys Lys Ala Glu Ile Ala Glu Phe Phe Glu Thr Tyr Lys Asn Leu
    130                 135                 140

Glu Ala Gly Lys Glu Val Ser Val Gly Asp Trp Glu Asp Ala Gln Ser
145                 150                 155                 160

Ala Lys Asp Ala Ile Glu His Ala Gln Asp Ser Thr Arg Arg Thr Ser
                165                 170                 175
```

```
Ser Ala Pro Thr Pro Phe Ser Arg Arg Asp Ala Gly Asn Tyr His Arg
        180                 185                 190

Val Ser Arg Pro Thr Ile Pro Cys Ala Met Arg Met Gly Asn Ile Leu
        195                 200                 205

Ser Val Ala Ala Leu Arg Ser Arg Met Ser Thr Asp Gln Pro Glu Ala
        210                 215                 220

Gly Leu Asp His Leu Thr Val Val Pro Thr Asn Leu Asp Glu Ser Asp
225                 230                 235                 240

Gly Asp Asp Asp Arg Asp Ala
                245

<210> SEQ ID NO 106
<211> LENGTH: 158
<212> TYPE: PRT
<213> ORGANISM: halophilic archaeon

<400> SEQUENCE: 106

Met Thr Asn Leu Trp Glu Asp Leu Glu Thr Gly Pro Asp Ala Pro Glu
1               5                   10                  15

Glu Ile Tyr Ala Val Val Glu Cys Leu Lys Gly Glu Arg Asn Lys Tyr
            20                  25                  30

Glu Tyr Asp Lys Asp Val Pro Gly Val Val Leu Asp Arg Val Leu His
        35                  40                  45

Ser Asn Val His Tyr Pro Ala Asp Tyr Gly Phe Ile Pro Gln Ser Tyr
    50                  55                  60

Tyr Asp Asp Gly Asp Pro Phe Asp Val Leu Ala Leu Val Glu Asp Gln
65                  70                  75                  80

Thr Phe Pro Gly Cys Val Ile Glu Ala Arg Pro Val Ala Leu Met Gly
                85                  90                  95

Met Asp Asp Asp Gly Glu Gln Asp Asp Lys Val Ile Ala Val Pro Ser
            100                 105                 110

Glu Asp Pro Arg Tyr Asp His Ile Glu Asp Leu Ala Asp Val Pro Gln
        115                 120                 125

Gln Thr Leu Asp Glu Ile Glu Glu Phe Phe Ala Thr Tyr Lys Asn Leu
    130                 135                 140

Glu Glu Gly Lys Glu Val Glu Thr Leu Gly Phe Glu Asp Arg
145                 150                 155

<210> SEQ ID NO 107
<211> LENGTH: 177
<212> TYPE: PRT
<213> ORGANISM: uncultured archaeon

<400> SEQUENCE: 107

Met Ala Asp Leu Trp Asn Asp Leu Glu Thr Gly Pro Asp Pro Pro Glu
1               5                   10                  15

Thr Val His Ala Val Val Glu Cys Leu Lys Gly Glu Arg Asn Lys Tyr
            20                  25                  30

Glu Tyr Asp Lys Ser Val Pro Gly Ile Val Leu Asp Arg Val Leu His
        35                  40                  45

Ala Asn Val His Tyr Pro Ser Asp Tyr Gly Phe Ile Pro Arg Ser Tyr
    50                  55                  60

Tyr Asp Asp Asp Asp Pro Leu Asp Val Leu Val Leu Val Glu Asp Ala
65                  70                  75                  80

Thr Phe Pro Gly Cys Val Val Glu Ala Arg Pro Val Ala Leu Met Arg
                85                  90                  95
```

Met Glu Asp Asp Gly Glu Gln Asp Lys Val Ile Ala Val Pro Thr
                    100                 105                 110

Glu Asp Pro Arg Tyr Asp His Val Glu Asp Val Asp Leu Thr Ala
                115                 120                 125

Gln Arg Lys Ala Glu Ile Ala Glu Phe Phe Glu Thr Tyr Lys Asn Leu
    130                 135                 140

Glu Ala Gly Lys Glu Thr Asp Thr Leu Gly Phe Glu Asp Arg Gln Ala
145                 150                 155                 160

Ala Met Asp Ala Val Glu His Ala Gln Glu Leu Tyr Glu Gln Phe
                165                 170                 175

Gly

<210> SEQ ID NO 108
<211> LENGTH: 178
<212> TYPE: PRT
<213> ORGANISM: halophilic archaeon

<400> SEQUENCE: 108

Met Thr Asp Leu Trp Arg Asp Leu Glu Thr Gly Pro Asn Pro Pro Glu
1               5                   10                  15

Thr Ile His Ala Val Val Glu Cys Leu Lys Gly Glu Arg Asn Lys Tyr
                20                  25                  30

Glu Tyr Asp Lys Ser Val Pro Gly Val Val Leu Asp Arg Val Leu His
            35                  40                  45

Ser Thr Val His Tyr Pro Ser Asp Tyr Gly Phe Ile Pro Arg Thr Tyr
        50                  55                  60

Tyr Asp Asp Asp Asp Pro Phe Asp Val Leu Val Leu Val Ala Asp Ala
65                  70                  75                  80

Thr Phe Pro Gly Cys Val Ile Glu Ala Arg Pro Leu Ala Leu Met Arg
                85                  90                  95

Met Asp Asp Asp Gly Glu Gln Asp Lys Val Ile Ala Val Pro Thr
                    100                 105                 110

Glu Asp Pro Arg Tyr Asp His Met Thr Asp Leu Ala Asp Leu Pro Glu
                115                 120                 125

Gln Arg Arg Asp Glu Ile Ala Glu Phe Phe Glu Thr Tyr Lys Asn Leu
    130                 135                 140

Glu Pro Gly Lys Glu Thr Asp Thr Leu Gly Trp Asp Asp Arg Gln Ala
145                 150                 155                 160

Ala Leu Glu Ala Ile Glu His Ala Gln Glu Gln Tyr Gln Arg Glu Phe
                165                 170                 175

Gly Asn

<210> SEQ ID NO 109
<211> LENGTH: 8
<212> TYPE: PRT
<213> ORGANISM: Artificial sequence
<220> FEATURE:
<223> OTHER INFORMATION: FLAG-tag

<400> SEQUENCE: 109

Asp Tyr Lys Asp Asp Asp Asp Lys
1               5

<210> SEQ ID NO 110
<211> LENGTH: 32
<212> TYPE: DNA
<213> ORGANISM: Artificial sequence

```
<220> FEATURE:
<223> OTHER INFORMATION: Primer 1: PPA NdeI forward

<400> SEQUENCE: 110
tacatatggt gaacctctgg gaagatatgg ag                                32

<210> SEQ ID NO 111
<211> LENGTH: 35
<212> TYPE: DNA
<213> ORGANISM: Artificial sequence
<220> FEATURE:
<223> OTHER INFORMATION: Primer 2: PPA BlpI reverse

<400> SEQUENCE: 111
ctacgaagag aacttcgcgt aagcgagctg agcta                             35
```